US012797365B2

(12) United States Patent
Rawls et al.

(10) Patent No.: US 12,797,365 B2
(45) Date of Patent: Nov. 17, 2026

(54) COMPOSITIONS AND METHODS FOR MODULATING TRP CHANNEL ACTIVITY

(71) Applicant: DUKE UNIVERSITY, Durham, NC (US)

(72) Inventors: John Rawls, Durham, NC (US); Lihua Ye, Durham, NC (US); Rodger Liddle, Durham, NC (US); Sven-Eric Jordt, Durham, NC (US); Venkata Jabba, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 731 days.

(21) Appl. No.: 17/920,465

(22) PCT Filed: Apr. 22, 2021

(86) PCT No.: PCT/US2021/028602
§ 371 (c)(1),
(2) Date: Oct. 21, 2022

(87) PCT Pub. No.: WO2021/216841
PCT Pub. Date: Oct. 28, 2021

(65) Prior Publication Data

US 2023/0149355 A1 May 18, 2023

Related U.S. Application Data

(60) Provisional application No. 63/014,186, filed on Apr. 23, 2020.

(51) Int. Cl.
*A61K 31/405* (2006.01)
*A61K 31/404* (2006.01)
*A61K 31/4045* (2006.01)

(52) U.S. Cl.
CPC .......... *A61K 31/405* (2013.01); *A61K 31/404* (2013.01); *A61K 31/4045* (2013.01)

(58) Field of Classification Search
None
See application file for complete search history.

(56) References Cited

U.S. PATENT DOCUMENTS

| | | | |
|---|---|---|---|
| 2011/0098265 | A1 | 4/2011 | Bull et al. |
| 2015/0258151 | A1 | 9/2015 | Mani et al. |
| 2018/0250350 | A1 | 9/2018 | Sokol et al. |

FOREIGN PATENT DOCUMENTS

| | | |
|---|---|---|
| WO | WO 2010/005965 | 1/2010 |
| WO | WO 2017/136795 | 8/2017 |
| WO | WO 2018/136884 | 7/2018 |
| WO | WO 2019/070913 | 4/2019 |

OTHER PUBLICATIONS

Lacy BE. Diagnosis and treatment of diarrhea-predominant irritable bowel syndrome. Int J Gen Med. Feb. 11, 2016;9:7-17. (Year: 2016).*

PubChem. 3-(Indol-3-yl)propionic acid. Retrieved from the internet on May 13, 2025, https://pubchem.ncbi.nlm.nih.gov/compound/92904#section=Depositor-Supplied-Synonyms. (Year: 2025).*

PubChem. Indole-3-lactic acid. Retrieved from the Internet on May 13, 2025, https://pubchem.ncbi.nlm.nih.gov/compound/3744#section=Depositor-Supplied-Synonyms&fullscreen=true. (Year: 2025).*

Roager, H.M., Licht, T.R. Microbial tryptophan catabolites in health and disease. Nat Commun 9, 3294 (2018). (Year: 2018).*

Mcquaid, Kenneth R. "Drugs used in the treatment of gastrointestinal diseases." Basic & clinical pharmacology 12 (2018). (Year: 2018).*

Hu et al. Update of Indoles: Promising molecules for ameliorating metabolic diseases, Biomedicine & Pharmacotherapy, vol. 150, 2022. (Year: 2022).*

PubChem. Indole-3-Carboxaldehyde. Retrieved from the Internet on May 30, 2025, https://pubchem.ncbi.nlm.nih.gov/compound/10256#section=Depositor-Supplied-Synonyms&fullscreen=true (Year: 2025).*

Translation of CN1931200 to Liu. Retrieved from the Espacenet on Mar. 25, 2026, https://worldwide.espacenet.com/patent/search/family/037877322/publication/CN1931200A?q=cn1931200. Published 2005. (Year: 2005).*

Extended European Search Report for EP 21793394.4, mailed Mar. 6, 2024, 8 pages.

International Search Report and Written Opinion for PCT/US2021/028602. Mailed Aug. 17, 2021. 11 pages.

Abayneh et al., *Edwardsiella piscicida* sp. nov., a novel species pathogenic to fish. J Appl Microbiol. Mar. 2013;114(3):644-54.

Alvers et al., Single continuous lumen formation in the zebrafish gut is mediated by smoothened-dependent tissue remodeling. Development. Mar. 2014;141(5):1110-9.

Avelar Rodriguez et al., Small Intestinal Bacterial Overgrowth in Children: A State-Of-The-Art Review. Front Pediatr. Sep. 4, 2019:7:363.

Bautista et al., TRPA1 mediates the inflammatory actions of environmental irritants and proalgesic agents. Cell. Mar. 24, 2006;124(6):1269-82.

Bellono et al., Enterochromaffin Cells Are Gut Chemosensors that Couple to Sensory Neural Pathways. Cell. Jun. 29, 2017;170(1):185-198.e16.

Bercik et al., The anxiolytic effect of Bifidobacterium longum NCC3001 involves vagal pathways for gut-brain communication. Neurogastroenterol Motil. Dec. 2011;23(12):1132-9.

Berthoud et al., Brainstem mechanisms integrating gut-derived satiety signals and descending forebrain information in the control of meal size. Physiol Behav. Nov. 30, 2006;89(4):517-24.

(Continued)

*Primary Examiner* — Lauren Wells
(74) *Attorney, Agent, or Firm* — Casimir Jones, S.C.; Rikki A. Hullinger

(57) ABSTRACT

Provided herein are compositions comprising tryptophan catabolites and methods of use thereof. In particular, provided herein are compositions comprising tryptophan catabolites and uses thereof in methods of treating gastrointestinal disorders, suppressing appetite, and promoting weight loss in a subject.

4 Claims, 49 Drawing Sheets

Specification includes a Sequence Listing.

(56) References Cited

OTHER PUBLICATIONS

Bhattarai et al., Gut Microbiota-Produced Tryptamine Activates an Epithelial G-Protein-Coupled Receptor to Increase Colonic Secretion. Cell Host Microbe. Jun. 13, 2018;23(6):775-785.e5.
Bohorquez et al., Neuroepithelial circuit formed by innervation of sensory enteroendocrine cells. J Clin Invest. Feb. 2015;125(2):782-6.
Bonaz et al., The Vagus Nerve at the Interface of the Microbiota-Gut-Brain Axis. Front Neurosci. Feb. 7, 2018:12:49. 9 pages.
Bondurand et al., The role of SOX10 during enteric nervous system development. Dev Biol. Oct. 1, 2013;382(1):330-43.
Bornstein. Intrinsic sensory neurons of mouse gut—toward a detailed knowledge of enteric neural circuitry across species. Focus on "characterization of myenteric sensory neurons in the mouse small intestine". J Neurophysiol. Sep. 2006;96(3):973-4.
Bravo et al., Ingestion of Lactobacillus strain regulates emotional behavior and central GABA receptor expression in a mouse via the vagus nerve. Proc Natl Acad Sci U S A. Sep. 20, 2011;108(38):16050-5.
Breit et al., Vagus Nerve as Modulator of the Brain-Gut Axis in Psychiatric and Inflammatory Disorders. Front Psychiatry. Mar. 13, 2018:9:44.
Brookes et al., Extrinsic primary afferent signalling in the gut. Nat Rev Gastroenterol Hepatol. May 2013;10(5):286-96.
Brown et al., The gut microbial endocrine organ: bacterially derived signals driving cardiometabolic diseases. Annu Rev Med. 2015:66:343-59.
Bujan et al., Genetic studies to re-affiliate Edwardsiella tarda fish isolates to *Edwardsiella piscicida* and *Edwardsiella anguillarum* species. Syst Appl Microbiol. Jan. 2018;41(1):30-37.
Caceres et al., Transient Receptor Potential Cation Channel Subfamily M Member 8 channels mediate the anti-inflammatory effects of eucalyptol. Br J Pharmacol. May 2017;174(9):867-879.
Chimerel et al., Bacterial metabolite indole modulates incretin secretion from intestinal enteroendocrine L cells. Cell Rep. Nov. 20, 2014;9(4):1202-8.
Choi et al., Development of novel CH223191-based antagonists of the aryl hydrocarbon receptor. Mol Pharmacol. Jan. 2012;81(1):3-11.
Cocchiaro et al., Microgavage of zebrafish larvae. J Vis Exp. Feb. 20, 2013:(72):e4434.
Coleman et al., Bacterial Signaling at the Intestinal Epithelial Interface in Inflammation and Cancer. Front Immunol. Jan. 5, 2018:8:1927.
Cornelissen et al., Electrophysiological features of morphological Dogiel type II neurons in the myenteric plexus of pig small intestine. J Neurophysiol. Jul. 2000;84(1):102-11.
Cronan et al., Macrophage Epithelial Reprogramming Underlies Mycobacterial Granuloma Formation and Promotes Infection. Immunity. Oct. 18, 2016;45(4):861-876.
Espenschied et al., Epithelial delamination is protective during pharmaceutical-induced enteropathy. Proc Natl Acad Sci U S A. Aug. 20, 2019;116(34):16961-16970.
Flores et al., The zebrafish as a model for gastrointestinal tract-microbe interactions. Cell Microbiol. Mar. 2020;22(3):e13152. 15 pages.
Foglia et al., Multicolor mapping of the cardiomyocyte proliferation dynamics that construct the atrium. Development. May 15, 2016;143(10):1688-96.
Fosque et al., Neural circuits. Labeling of active neural circuits in vivo with designed calcium integrators. Science. Feb. 13, 2015;347(6223):755-60.
Fulling et al., Gut Microbe to Brain Signaling: What Happens in Vagus . . . Neuron. Mar. 20, 2019;101(6):998-1002.
Furness et al., Nutrient tasting and signaling mechanisms in the gut. II. The intestine as a sensory organ: neural, endocrine, and immune responses. Am J Physiol. Nov. 1999;277(5):G922-8.
Furness et al., The enteric nervous system and gastrointestinal innervation: integrated local and central control. Adv Exp Med Biol. 2014:817:39-71.
Furness et al., The gut as a sensory organ. Nat Rev Gastroenterol Hepatol. Dec. 2013;10(12):729-40.
Ganz et al., Image velocimetry and spectral analysis enable quantitative characterization of larval zebrafish gut motility. Neurogastroenterol Motil. Sep. 2018;30(9):e13351. 12 pages.
Gershon. 5-Hydroxytryptamine (serotonin) in the gastrointestinal tract. Curr Opin Endocrinol Diabetes Obes. Feb. 2013;20(1):14-21.
Gershon. Review article: serotonin receptors and transporters—roles in normal and abnormal gastrointestinal motility. Aliment Pharmacol Ther. Nov. 2004:20 Suppl 7:3-14.
Ghoshal et al., Breath tests in the diagnosis of small intestinal bacterial overgrowth in patients with irritable bowel syndrome in comparison with quantitative upper gut aspirate culture. Eur J Gastroenterol Hepatol. Jul. 2014;26(7):753-60.
Ghoshal et al., Small Intestinal Bacterial Overgrowth and Irritable Bowel Syndrome: A Bridge between Functional Organic Dichotomy. Gut Liver. Mar. 15, 2017;11(2):196-208.
Grill et al., The nucleus tractus solitarius: a portal for visceral afferent signal processing, energy status assessment and integration of their combined effects on food intake. Int J Obes (Lond). Apr. 2009:33 Suppl 1:S11-5.
Guo et al., The Cellular Diversity and Transcription Factor Code of *Drosophila* Enteroendocrine Cells. Cell Rep. Dec. 17, 2019;29(12):4172-4185.e5.
Gupta et al., Clonally dominant cardiomyocytes direct heart morphogenesis. Nature. Apr. 25, 2012;484(7395):479-84.
Haber et al., A single-cell survey of the small intestinal epithelium. Nature. Nov. 16, 2017;551(7680):333-339.
Han et al., A Neural Circuit for Gut-Induced Reward. Cell. Oct. 18, 2018;175(3):665-678.e23.
Heath-Pagliuso et al., Activation of the Ah receptor by tryptophan and tryptophan metabolites. Biochemistry. Aug. 18, 1998;37(33):11508-15.
Holzer. TRP channels in the digestive system. Curr Pharm Biotechnol. Jan. 1, 2011;12(1):24-34.
Hubbard et al., Adaptation of the human aryl hydrocarbon receptor to sense microbiota-derived indoles. Sci Rep. Aug. 3, 2015:5:12689. 13 pages.
Jaglin et al., Indole, a Signaling Molecule Produced by the Gut Microbiota, Negatively Impacts Emotional Behaviors in Rats. Front Neurosci. Apr. 9, 2018:12:216. 19 pages.
Jin et al., Microbiome-derived tryptophan metabolites and their aryl hydrocarbon receptor-dependent agonist and antagonist activities. Mol Pharmacol. May 2014;85(5):777-88.
John Haynes et al., Indole and other aromatic compounds activate the yeast TRPY1 channel. FEBS Lett. Apr. 30, 2008;582(10):1514-8.
Johnson et al., Deletion of choline acetyltransferase in enteric neurons results in postnatal intestinal dysmotility and dysbiosis. Faseb J. Sep. 2018;32(9):4744-4752.
Kaelberer et al., A gut-brain neural circuit for nutrient sensory transduction. Science. Sep. 21, 2018;361(6408):eaat5236.
Kaiko et al., Host-microbe interactions shaping the gastrointestinal environment. Trends Immunol. Nov. 2014;35(11):538-48.
Kawakami et al., Tol2: a versatile gene transfer vector in vertebrates. Genome Biol. 2007;8 Suppl 1 (Suppl 1):S7. 10 pages.
Kim et al., Vitamin B12 and folic acid alleviate symptoms of nutritional deficiency by antagonizing aryl hydrocarbon receptor. Proc Natl Acad Sci U S A. Jul. 7, 2020;117(27):15837-15845.
Knight et al., Ret signalling integrates a craniofacial muscle module during development. Development. May 2011;138(10):2015-24.
Kokel et al., Photochemical activation of TRPA1 channels in neurons and animals. Nat Chem Biol. Apr. 2013;9(4):257-63.
Kunst et al., A Cellular-Resolution Atlas of the Larval Zebrafish Brain. Neuron. Jul. 3, 2019;103(1):21-38.e5.
Kwan et al., The Tol2kit: a multisite gateway-based construction kit for Tol2 transposon transgenesis constructs. Dev Dyn. Nov. 2007;236(11):3088-99.
Lapointe et al., The role of TRPA1 in visceral inflammation and pain. Channels (Austin). Nov.-Dec. 2011;5(6):525-9.

(56) References Cited

OTHER PUBLICATIONS

Leite et al., The duodenal microbiome is altered in small intestinal bacterial overgrowth. PLoS One. Jul. 9, 2020;15(7):e0234906. 17 pages.
Li et al., Essential roles of enteric neuronal serotonin in gastrointestinal motility and the development/survival of enteric dopaminergic neurons. J Neurosci. Jun. 15, 2011;31(24):8998-9009.
Liu et al., Gut Microbial Metabolites of Aromatic Amino Acids as Signals in Host-Microbe Interplay. Trends Endocrinol Metab. Nov. 2020;31(11):818-834.
Love et al., Moderated estimation of fold change and dispersion for RNA-seq data with DESeq2. Genome Biol. 2014;15(12):550.
Lu et al., Free Fatty Acid Receptors in Enteroendocrine Cells. Endocrinology. Jul. 1, 2018;159(7):2826-2835.
Macpherson et al., Noxious compounds activate TRPA1 ion channels through covalent modification of cysteines. Nature. Feb. 1, 2007;445(7127):541-5.
Mathias et al., Enhanced cell-specific ablation in zebrafish using a triple mutant of *Escherichia coli* nitroreductase. Zebrafish. Apr. 2014;11(2):85-97.
Mcgraw et al., Postembryonic neuronal addition in zebrafish dorsal root ganglia is regulated by Notch signaling. Neural Dev. Jun. 27, 2012:7:23.
Meijering et al., Methods for cell and particle tracking. Methods Enzymol. 2012:504:183-200.
Meseguer et al., TRPA1 channels mediate acute neurogenic inflammation and pain produced by bacterial endotoxins. Nat Commun. 2014:5:3125.
Murdoch et al., Intestinal Serum amyloid A suppresses systemic neutrophil activation and bactericidal activity in response to microbiota colonization. PLoS Pathog. Mar. 7, 2019;15(3):e1007381. 30 pages.
Nagel et al., Channelrhodopsin-2, a directly light-gated cation-selective membrane channel. Proc Natl Acad Sci U S A. Nov. 25, 2003;100(24):13940-5.
Nakamura et al., Comparative genomics reveals that a fish pathogenic bacterium Edwardsiella tarda has acquired the locus of enterocyte effacement (LEE) through horizontal gene transfer. BMC Genomics. Sep. 22, 2013:14:642. 14 pages.
Naumann et al., From Whole-Brain Data to Functional Circuit Models: The Zebrafish Optomotor Response. Cell. Nov. 3, 2016;167(4):947-960.e20.
Nilius et al., Irritating channels: the case of TRPA1. J Physiol. Apr. 1, 2011;589(Pt 7):1543-9.
Nozawa et al., TRPA1 regulates gastrointestinal motility through serotonin release from enterochromaffin cells. Proc Natl Acad Sci U S A. Mar. 3, 2009;106(9):3408-13.
Pan et al., Activation of intrinsic afferent pathways in submucosal ganglia of the guinea pig small intestine. J Neurosci. May 1, 2000;20(9):3295-309.
Park et al., Pathogenesis of and strategies for preventing Edwardsiella tarda infection in fish. Vet Res. Oct. 4, 2012;43(1):67. 11 pages.
Pham et al., Methods for generating and colonizing gnotobiotic zebrafish. Nat Protoc. 2008;3(12):1862-75.
Prober et al., Zebrafish TRPA1 channels are required for chemosensation but not for thermosensation or mechanosensory hair cell function J Neurosci. Oct. 1, 2008;28(40):10102-10.
Puyskens et al., Aryl Hydrocarbon Receptor Modulation by Tuberculosis Drugs Impairs Host Defense and Treatment Outcomes. Cell Host Microbe. Feb. 12, 2020;27(2):238-248.e7.
Qu et al., Immunohistochemical analysis of neuron types in the mouse small intestine. Cell Tissue Res. Nov. 2008;334(2):147-61.
Randlett et al., Whole-brain activity mapping onto a zebrafish brain atlas. Nat Methods. Nov. 2015;12(11):1039-46.
Rawls et al., Reciprocal gut microbiota transplants from zebrafish and mice to germ-free recipients reveal host habitat selection. Cell. Oct. 20, 2006;127(2):423-33.
Roach et al., Loss of ascl1a prevents secretory cell differentiation within the zebrafish intestinal epithelium resulting in a loss of distal intestinal motility. Dev Biol. Apr. 15, 2013;376(2):171-86.
Roberts et al., Comparison of Human and Murine Enteroendocrine Cells by Transcriptomic and Peptidomic Profiling. Diabetes. May 2019;68(5):1062-1072.
Rolig et al., The enteric nervous system promotes intestinal health by constraining microbiota composition. PLoS Biol. Feb. 16, 2017;15(2):e2000689. 22 pages.
Schindelin et al., Fiji: an open-source platform for biological-image analysis. Nat Methods. Jun. 28, 2012;9(7):676-82.
Smith. A modification of the method for determining the production of indol by bacteria. J Exp Med. Sep. 1, 1897;2(5):543-7.
Srinivasa Rao et al., Functional genomics approach to the identification of virulence genes involved in Edwardsiella tarda pathogenesis. Infect Immun. Mar. 2003;71(3):1343-51.
Stephens et al., The composition of the zebrafish intestinal microbial community varies across development. ISME J. Mar. 2016;10(3):644-54.
Sun et al., Activation of aryl hydrocarbon receptor by dioxin directly shifts gut microbiota in zebrafish. Environ Pollut. Dec. 2019;255(Pt 3):113357. 12 pages.
Sun et al., Metformin Triggers PYY Secretion in Human Gut Mucosa. J Clin Endocrinol Metab. Jul. 1, 2019;104(7):2668-2674.
Symonds et al., Mechanisms of activation of mouse and human enteroendocrine cells by nutrients. Gut. Apr. 2015;64(4):618-26.
Taraviras et al., Signalling by the RET receptor tyrosine kinase and its role in the development of the mammalian enteric nervous system. Development. Jun. 1999;126(12):2785-97.
Tornini et al., Live fate-mapping of joint-associated fibroblasts visualizes expansion of cell contributions during zebrafish fin regeneration. Development. Aug. 15, 2017;144(16):2889-2895.
Travagli et al., Brainstem circuits regulating gastric function. Annu Rev Physiol. 2006:68:279-305.
Travagli et al., Vagal neurocircuitry and its influence on gastric motility. Nat Rev Gastroenterol Hepatol. Jul. 2016; 13(7):389-401.
Tseng et al., Spatial organization of the extracellular matrix regulates cell-cell junction positioning. Proc Natl Acad Sci U S A. Jan. 31, 2012;109(5):1506-11.
Ulhaq et al., Brain Aromatase Modulates Serotonergic Neuron by Regulating Serotonin Levels in Zebrafish Embryos and Larvae. Front Endocrinol (Lausanne). May 9, 2018:9:230. 13 pages.
Venkatesh et al., Symbiotic bacterial metabolites regulate gastrointestinal barrier function via the xenobiotic sensor PXR and Toll-like receptor 4. Immunity. Aug. 21, 2014;41(2):296-310.
Yang et al., Edwardsiella comparative phylogenomics reveal the new intra/inter-species taxonomic relationships, virulence evolution and niche adaptation mechanisms. PLoS One. 2012;7(5):e36987. 15 pages.
Yang et al., TRPA1-expressing lamina propria mesenchymal cells regulate colonic motility. JCI Insight. May 2, 2019;4(9):e122402. 17 pages.
Yano et al., Indigenous bacteria from the gut microbiota regulate host serotonin biosynthesis. Cell. Apr. 9, 2015;161(2):264-76.
Ye et al., High fat diet induces microbiota-dependent silencing of enteroendocrine cells. Elife. Dec. 3, 2019:8:e48479. 39 pages.
Yue et al., Protective effects of folic acid on PM2.5-induced cardiac developmental toxicity in zebrafish embryos by targeting AhR and Wnt/β-catenin signal pathways. Environ Toxicol. Oct. 2017;32(10):2316-2322.
Zelante et al., Tryptophan catabolites from microbiota engage aryl hydrocarbon receptor and balance mucosal reactivity via interleukin-22. Immunity. Aug. 22, 2013;39(2):372-85.
Zelkas et al., Serotonin-secreting enteroendocrine cells respond via diverse mechanisms to acute and chronic changes in glucose availability. Nutr Metab (Lond). Dec. 15, 2015:12:55.

* cited by examiner

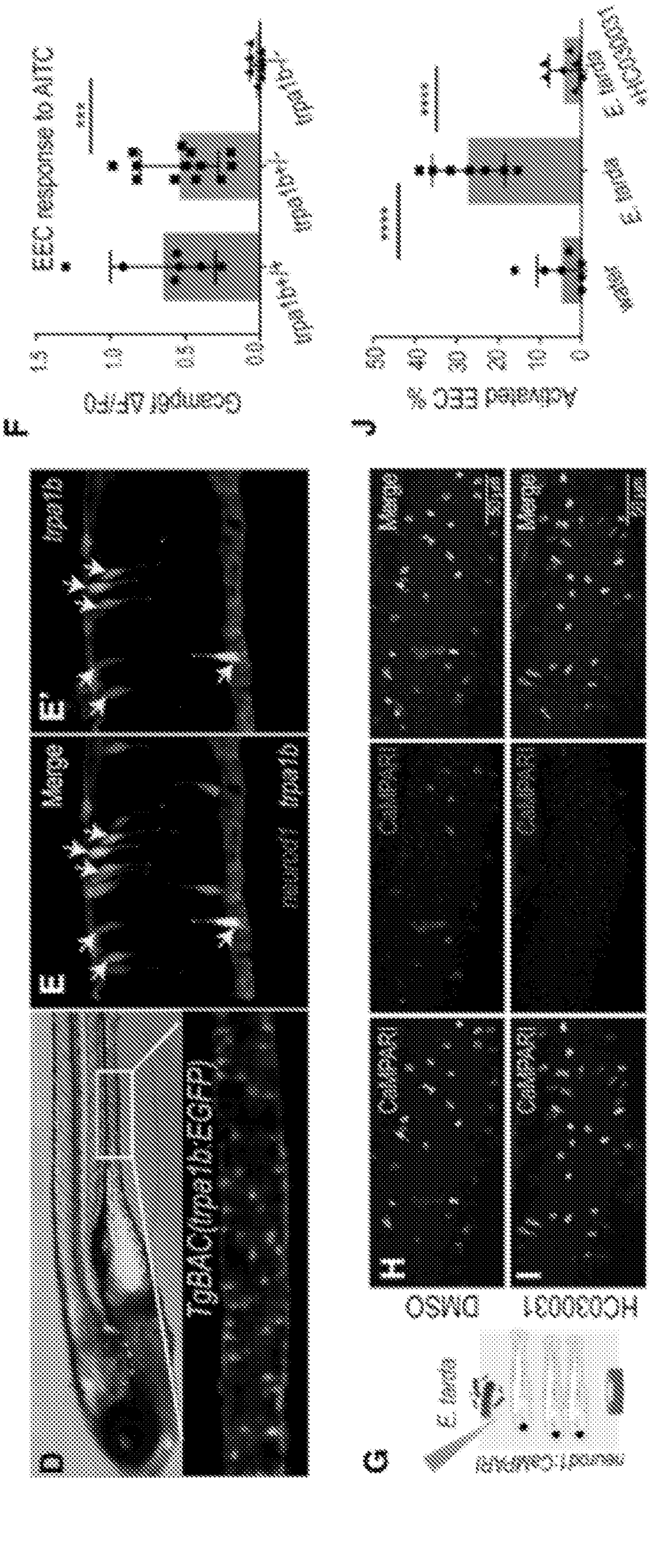
Fig. 3D-J

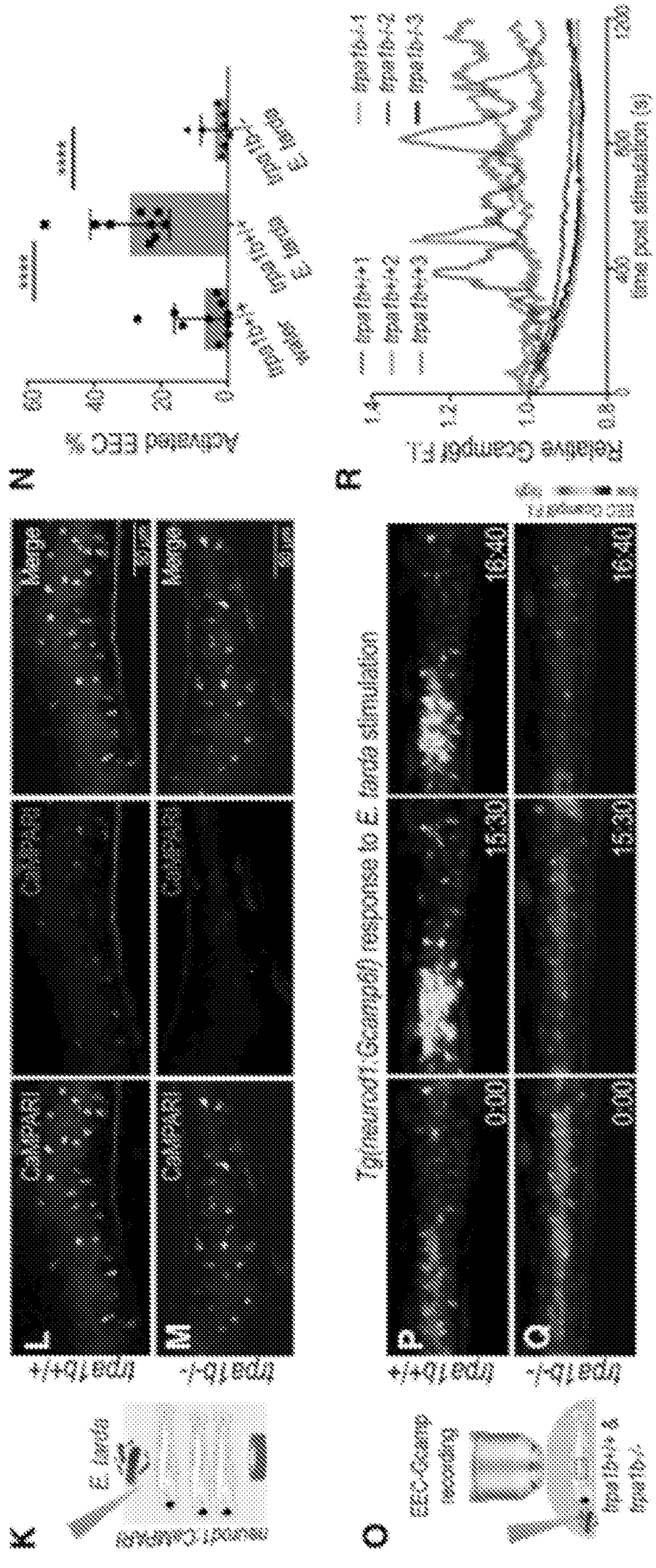
FIG. 3K-R

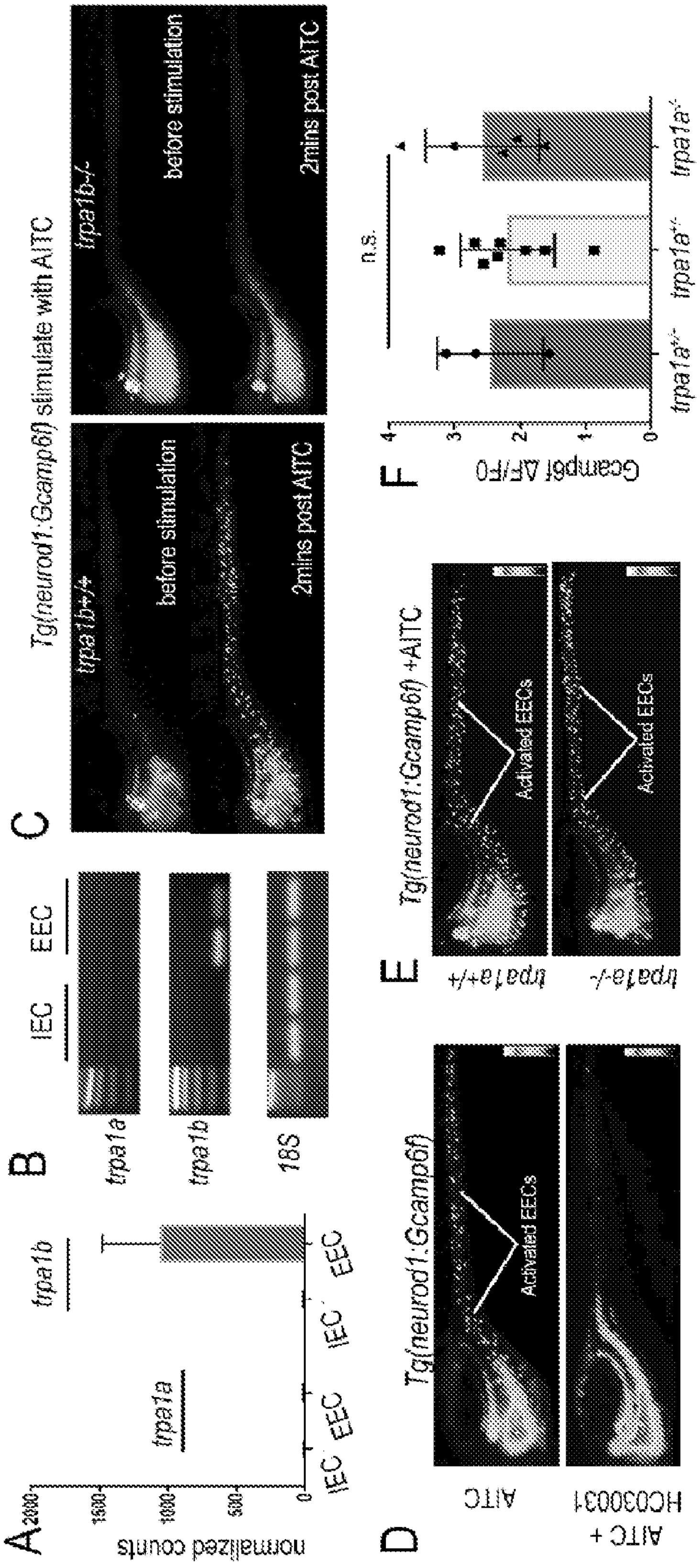
FIG. 4A-F

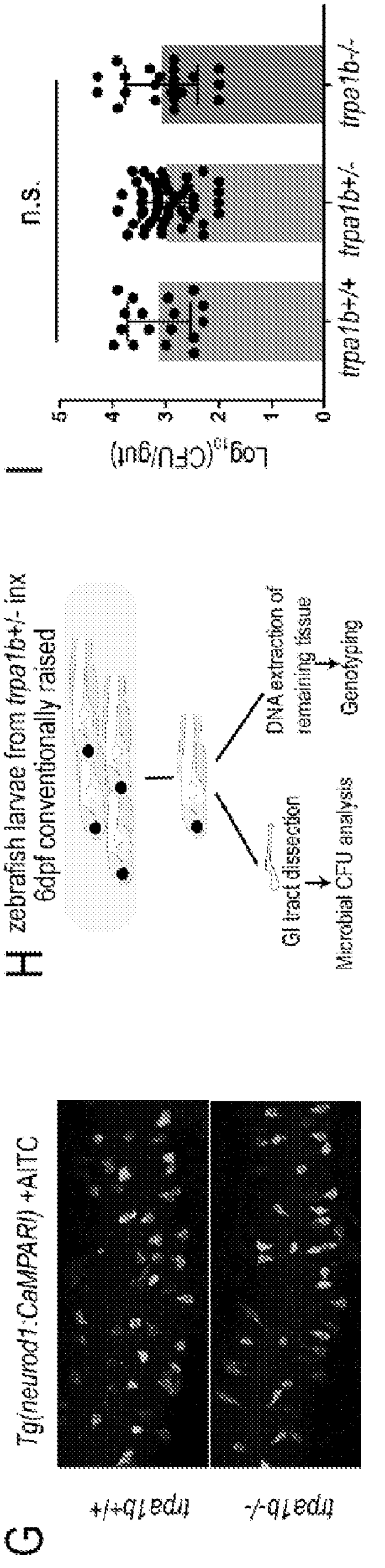
FIG. 4G-I

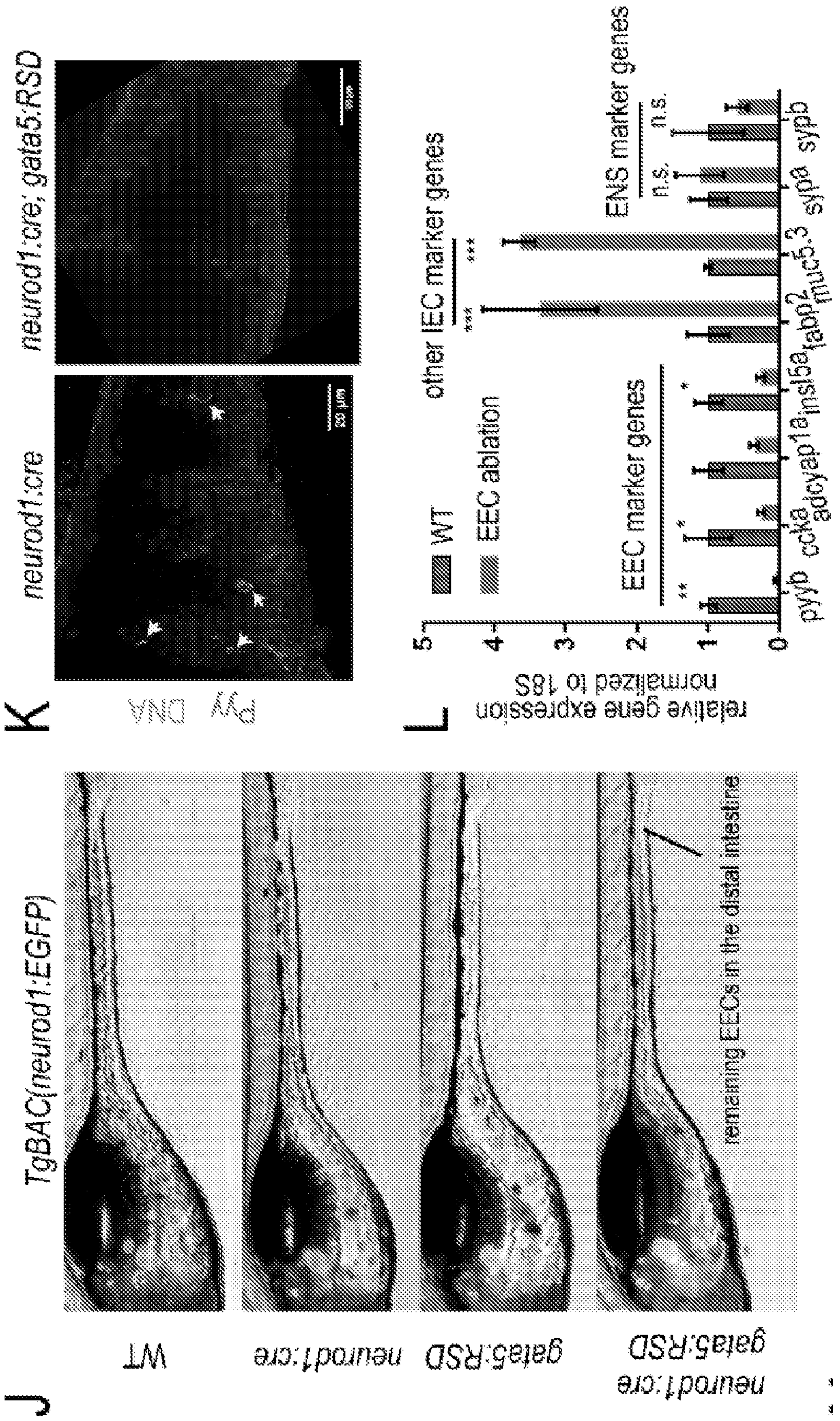
FIG. 4J-L

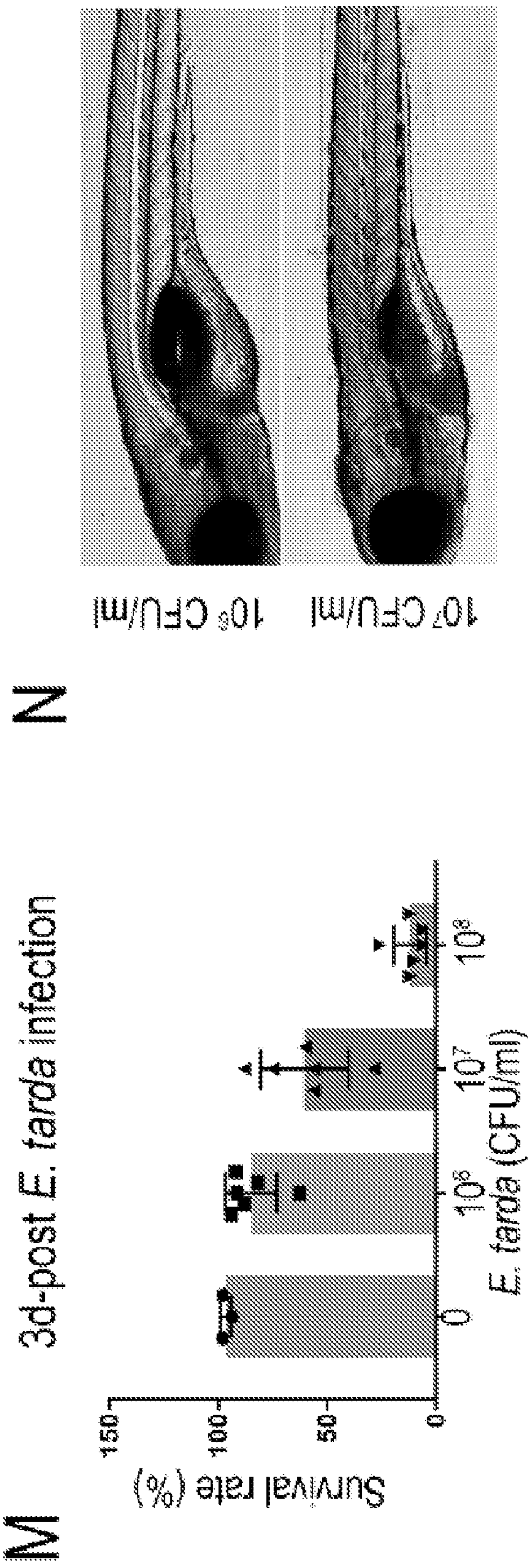
FIG. 4M-N

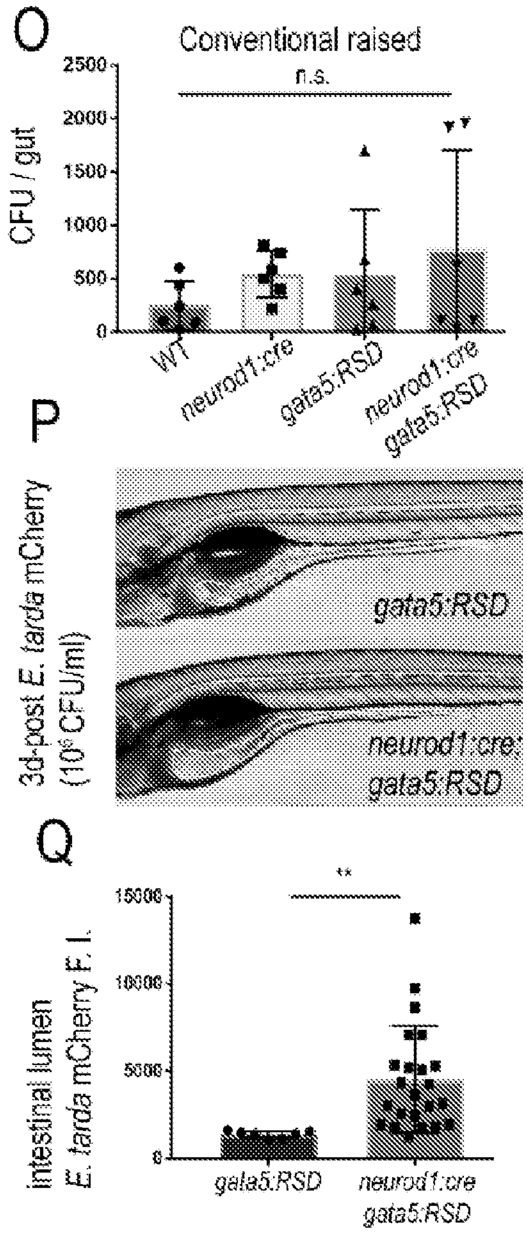
FIG. 4O-Q

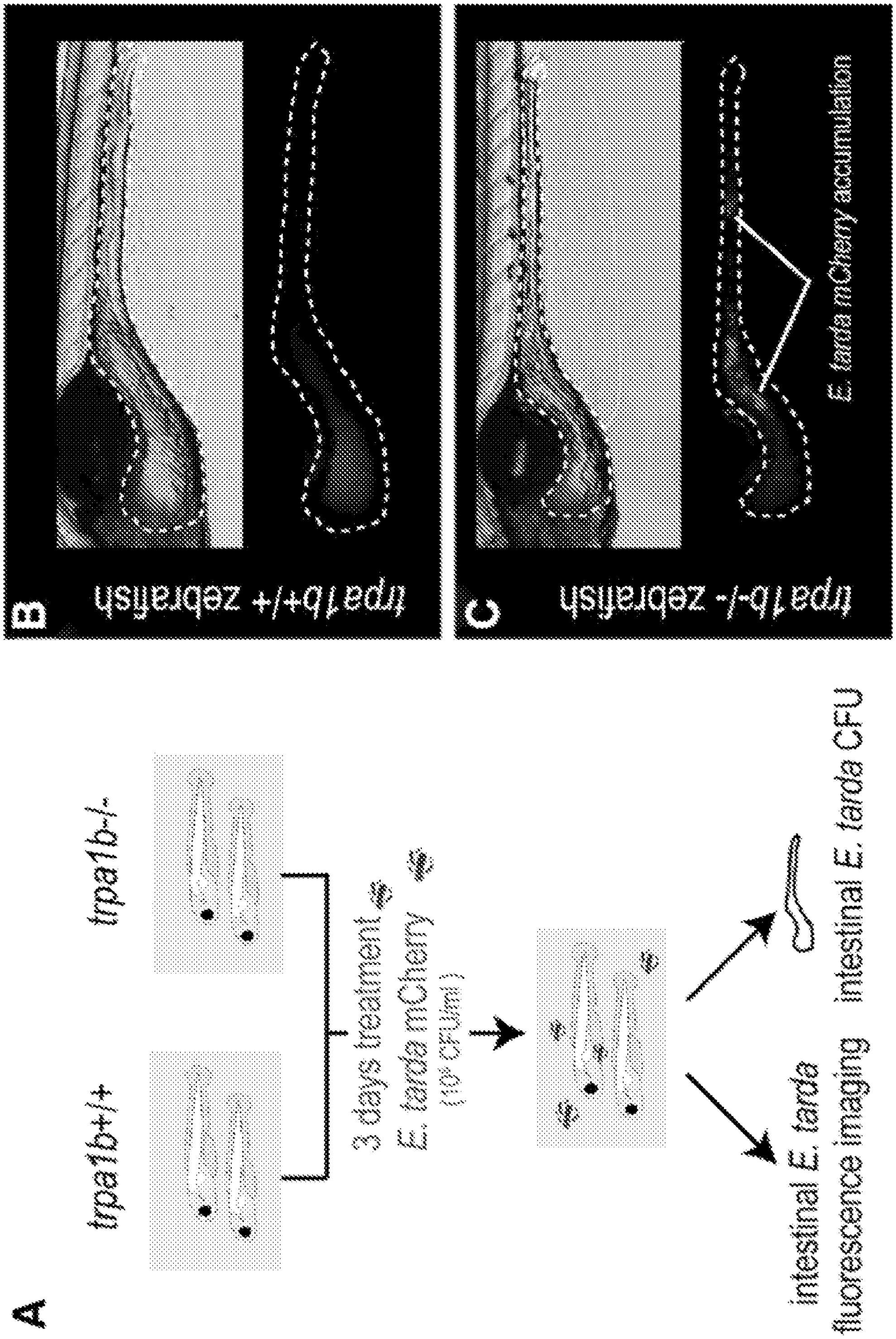
FIG. 5A-C

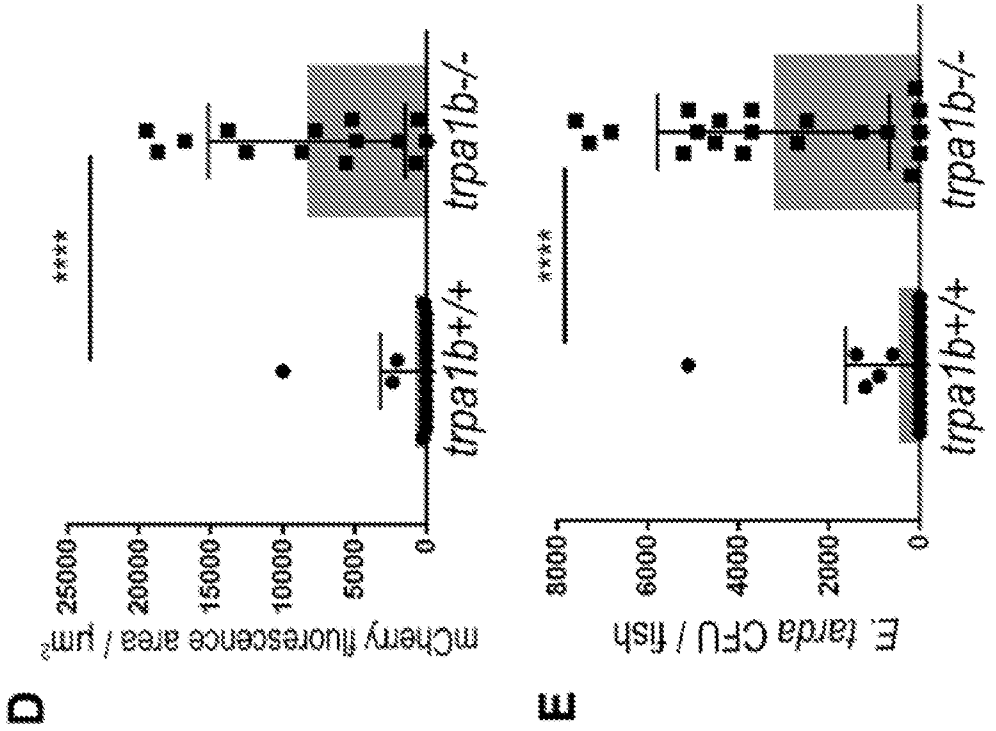
FIG. 5D-E

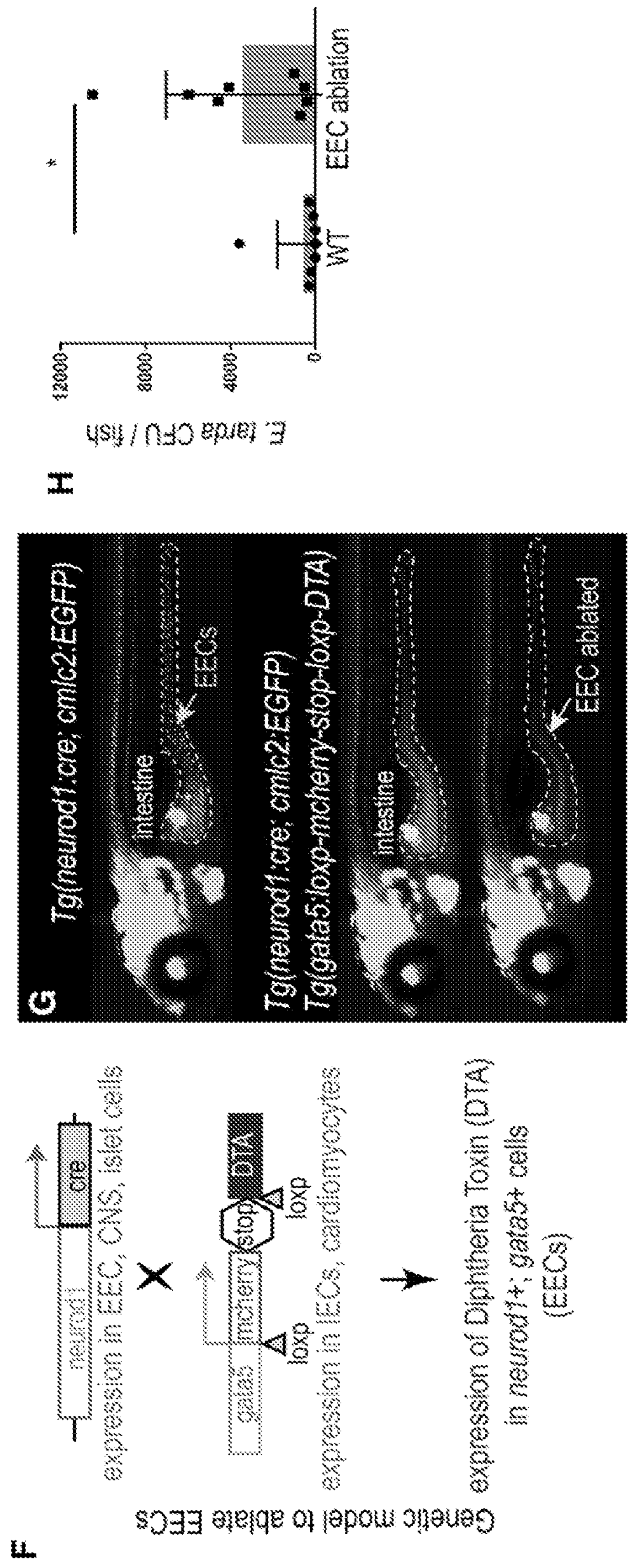
FIG. 5F-H

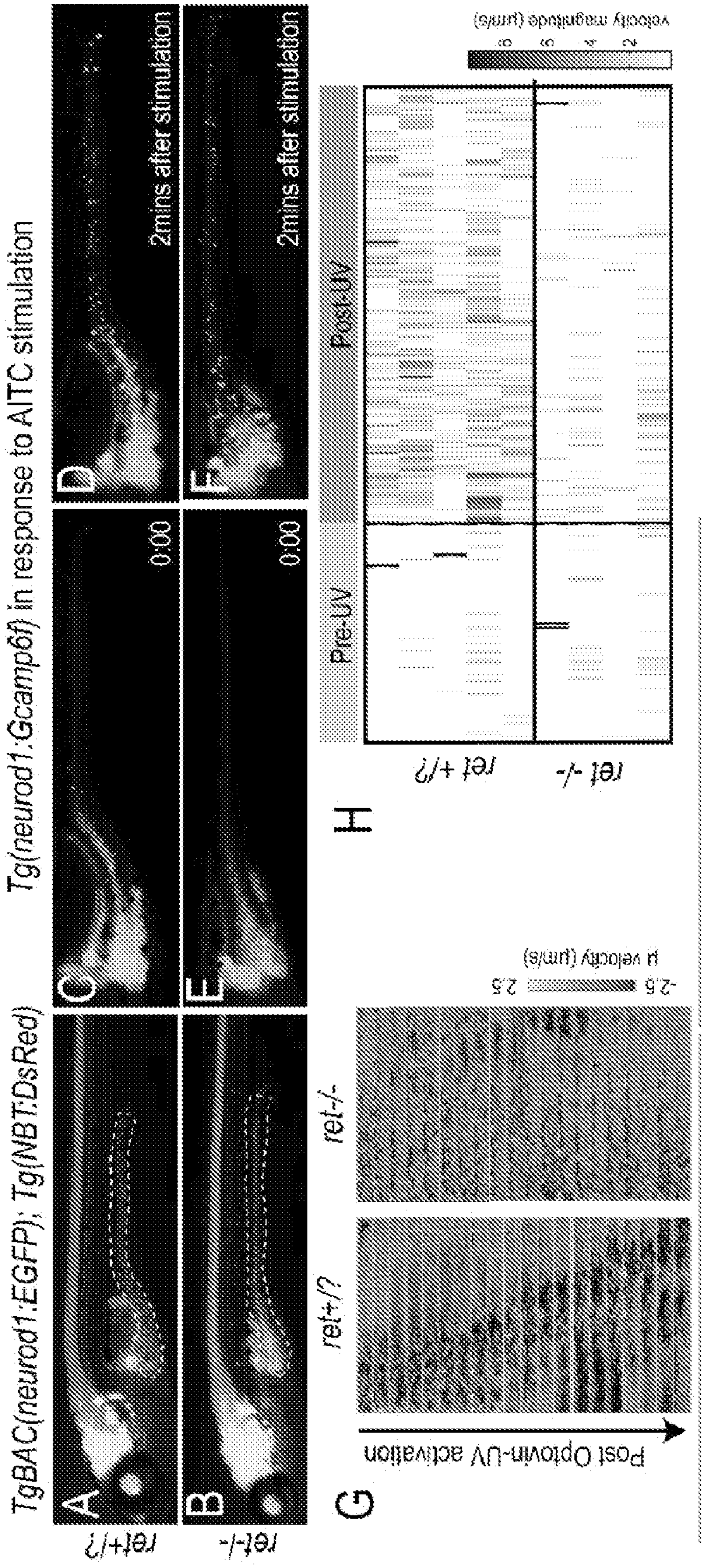
FIG. 6A-H

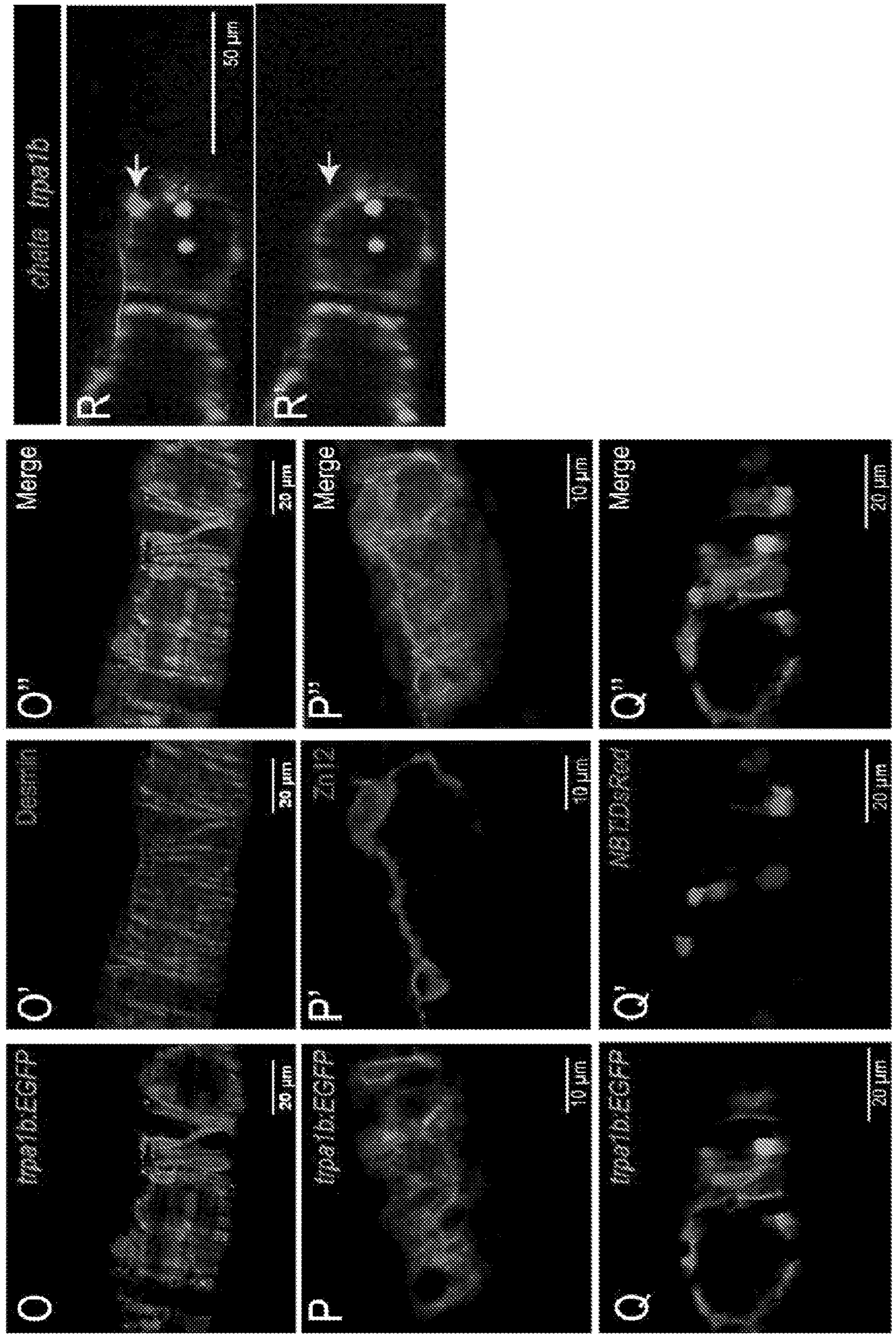
FIG. 6O-R

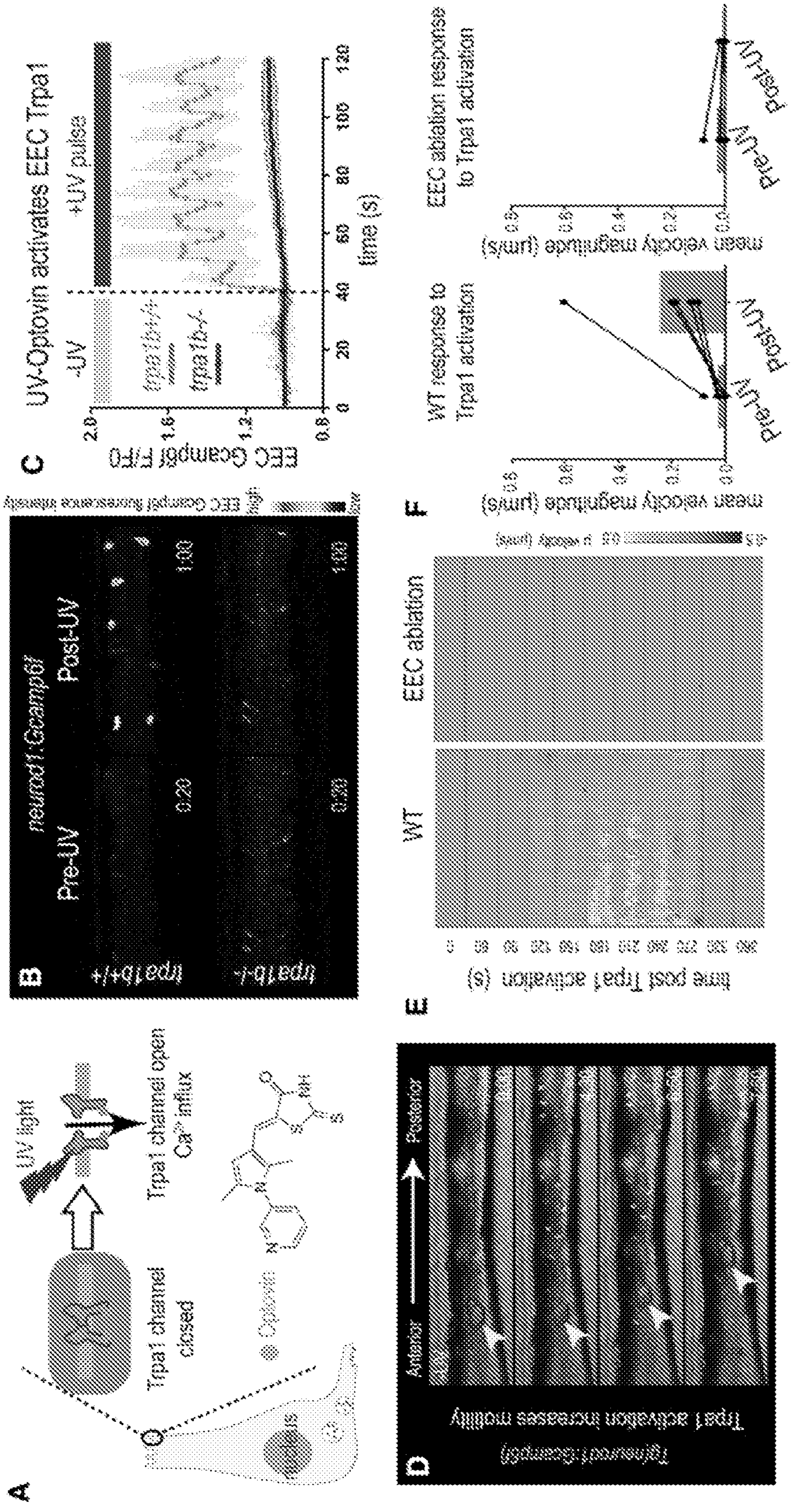
FIG. 7A-F

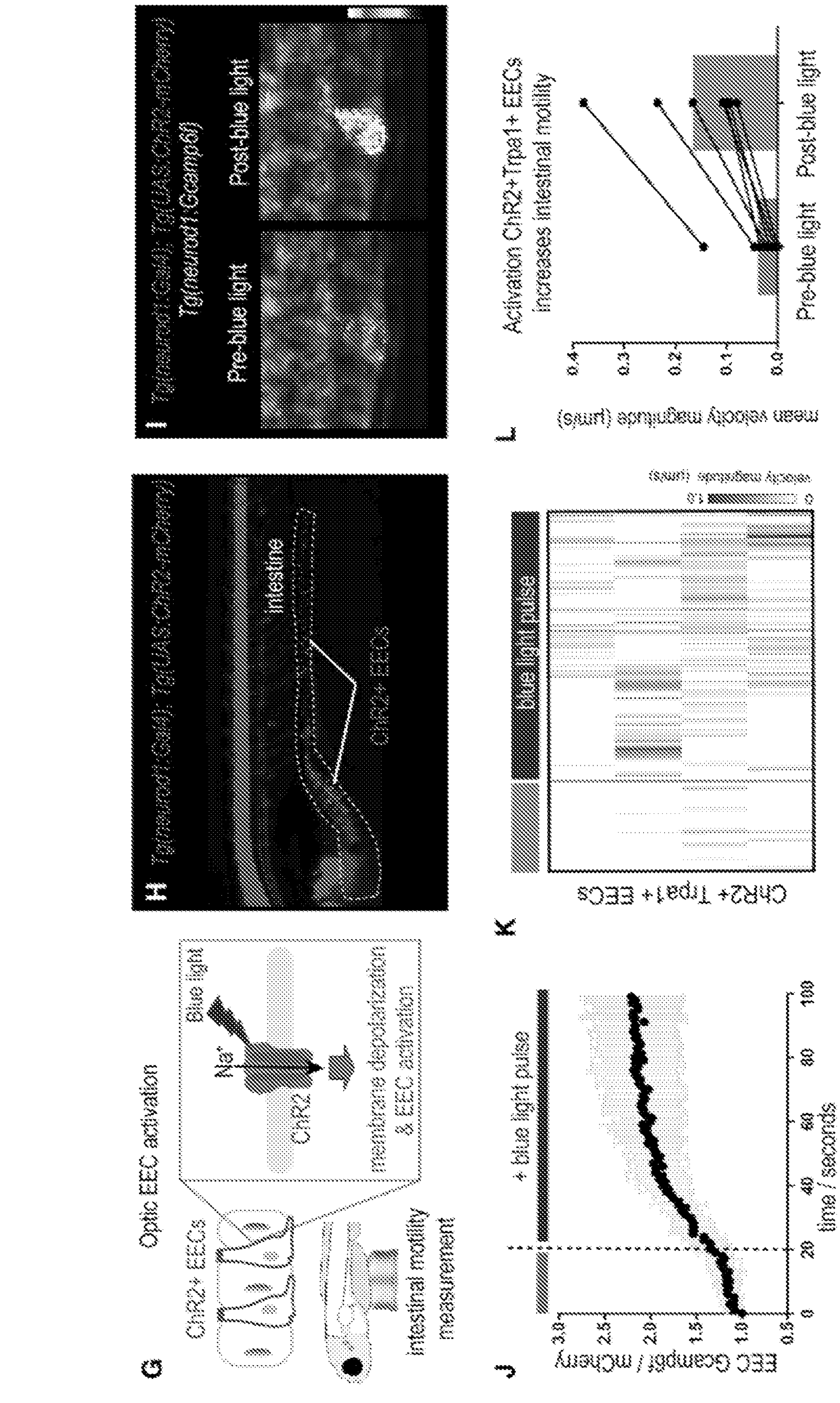
FIG. 7G-L

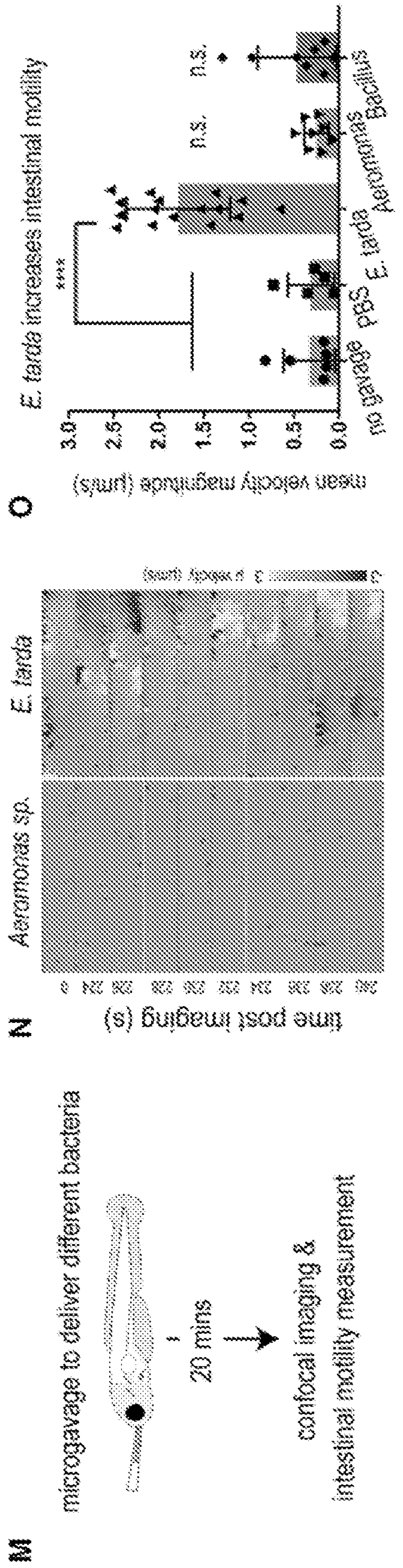
FIG. 7M-O

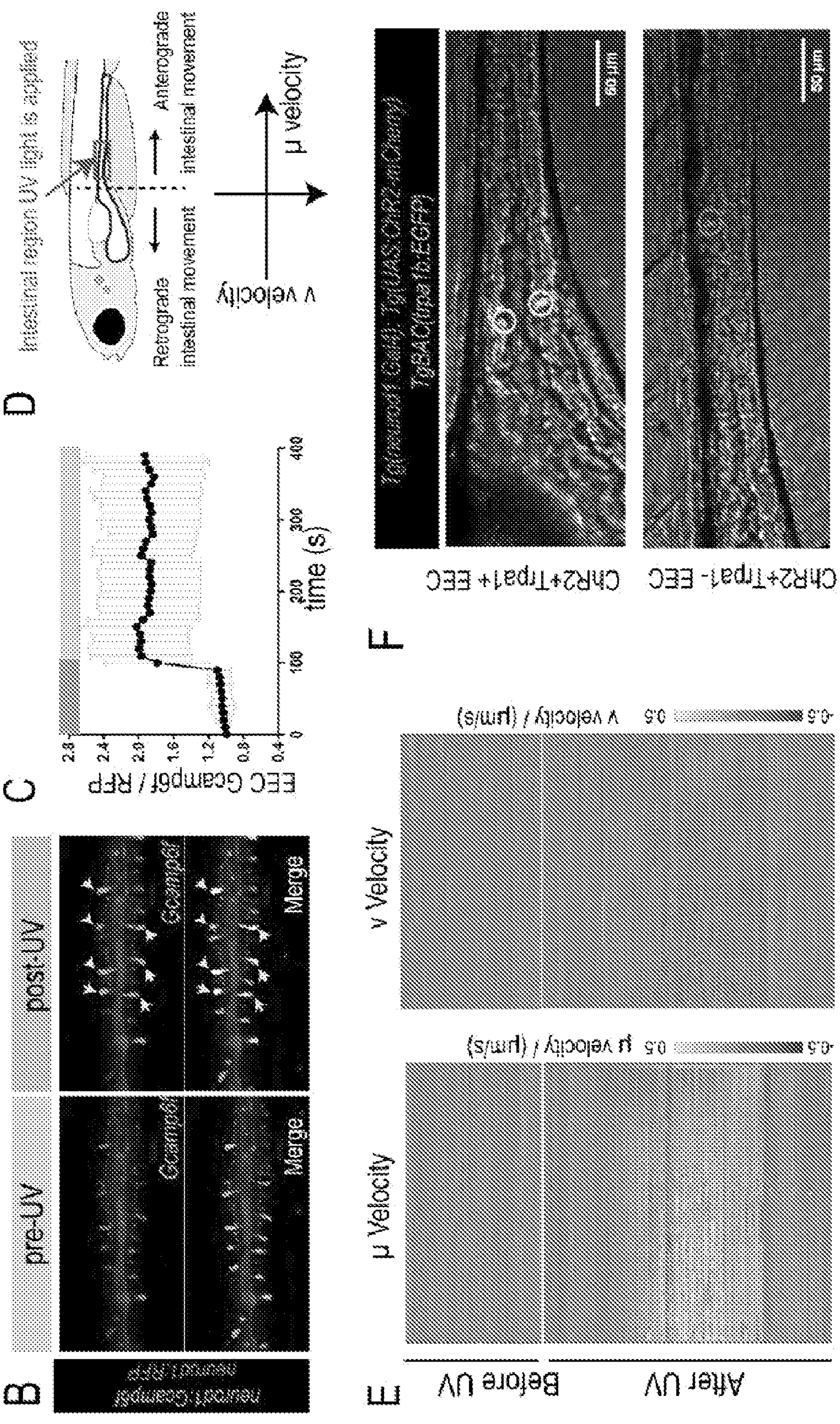
FIG. 8B-F

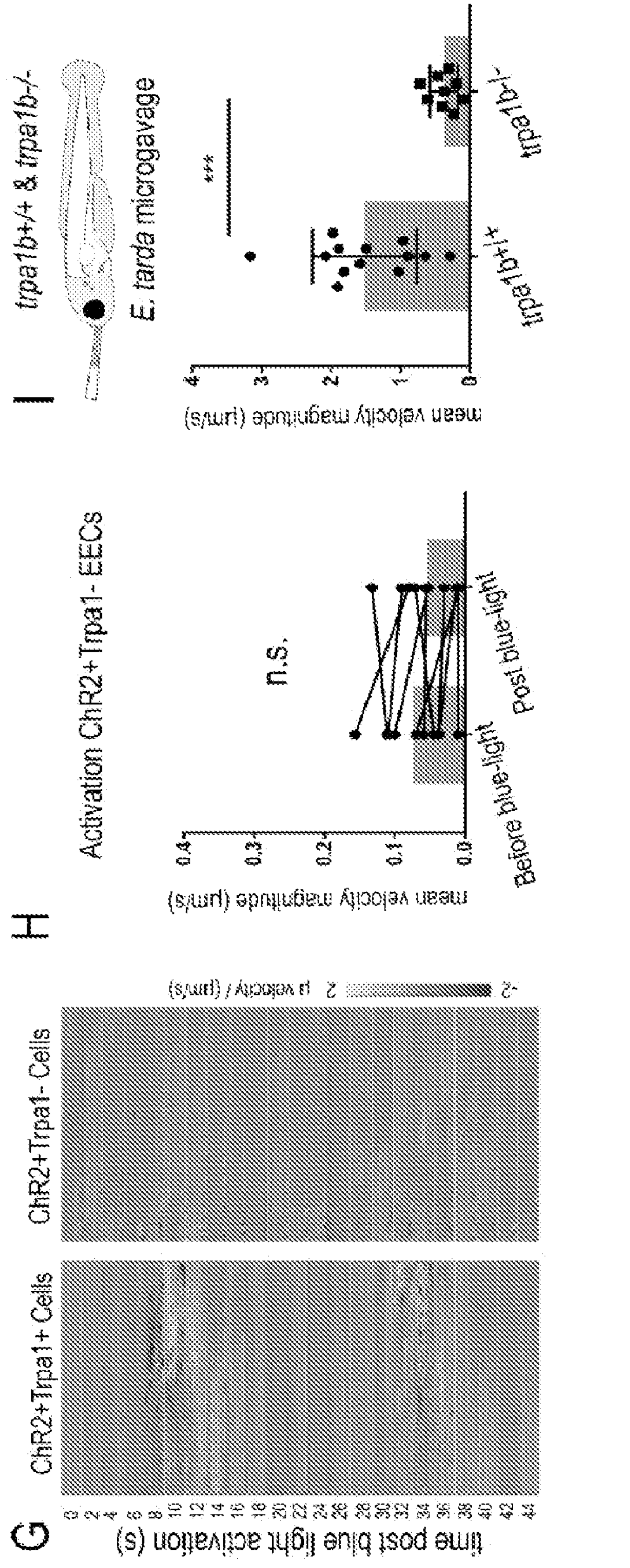
FIG. 8G-I

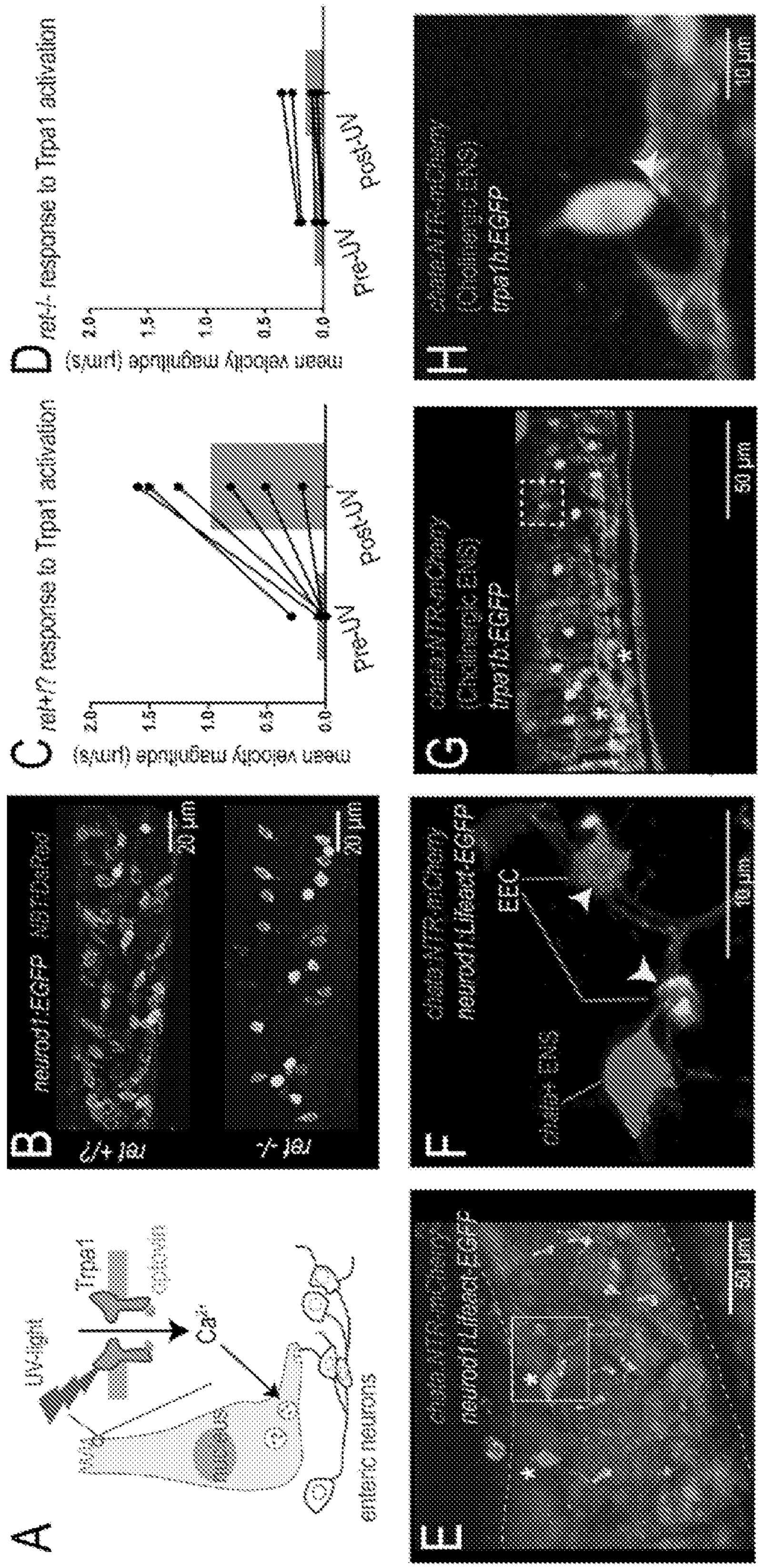
FIG. 9A-H

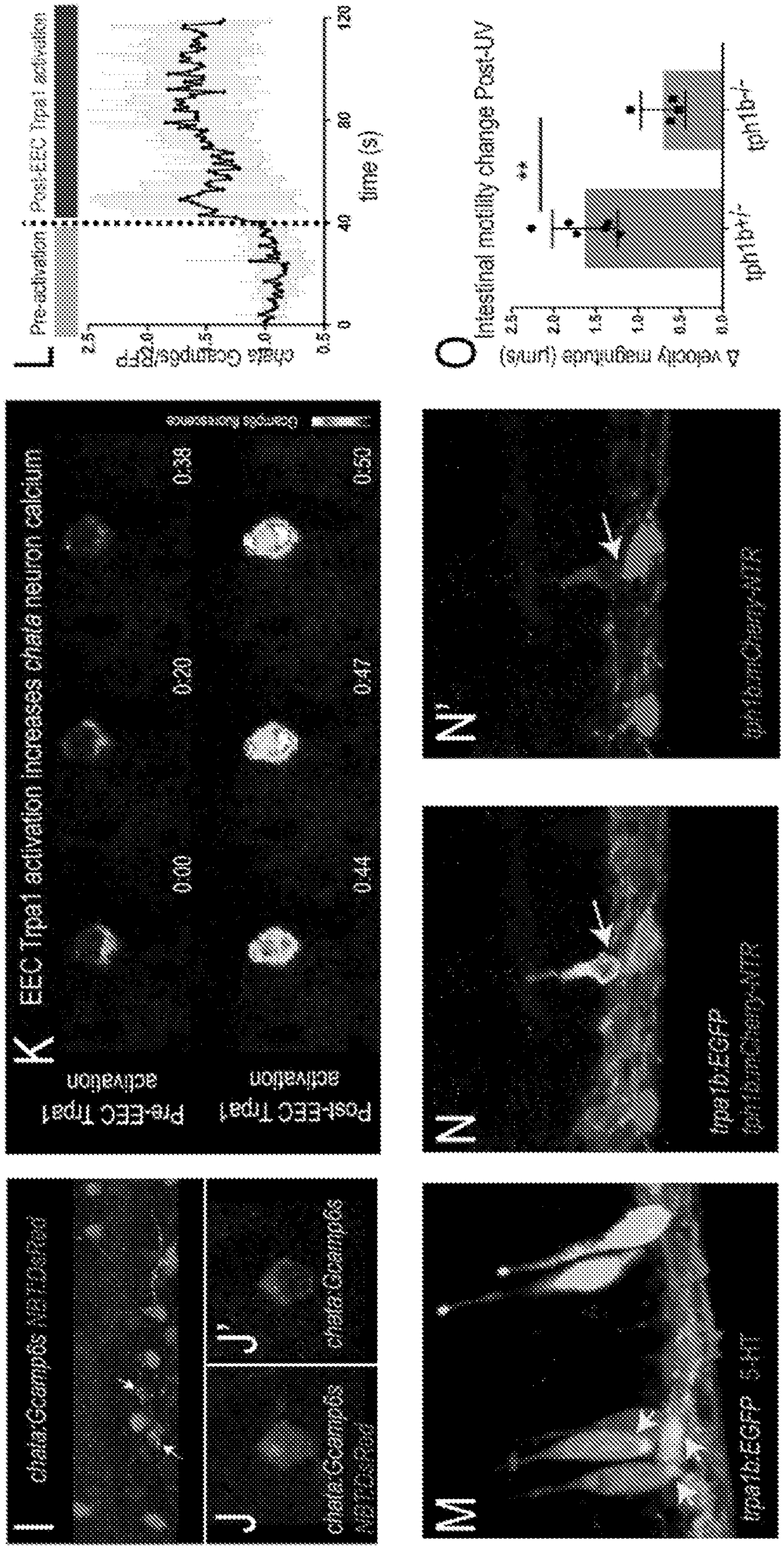
FIG. 9I-O

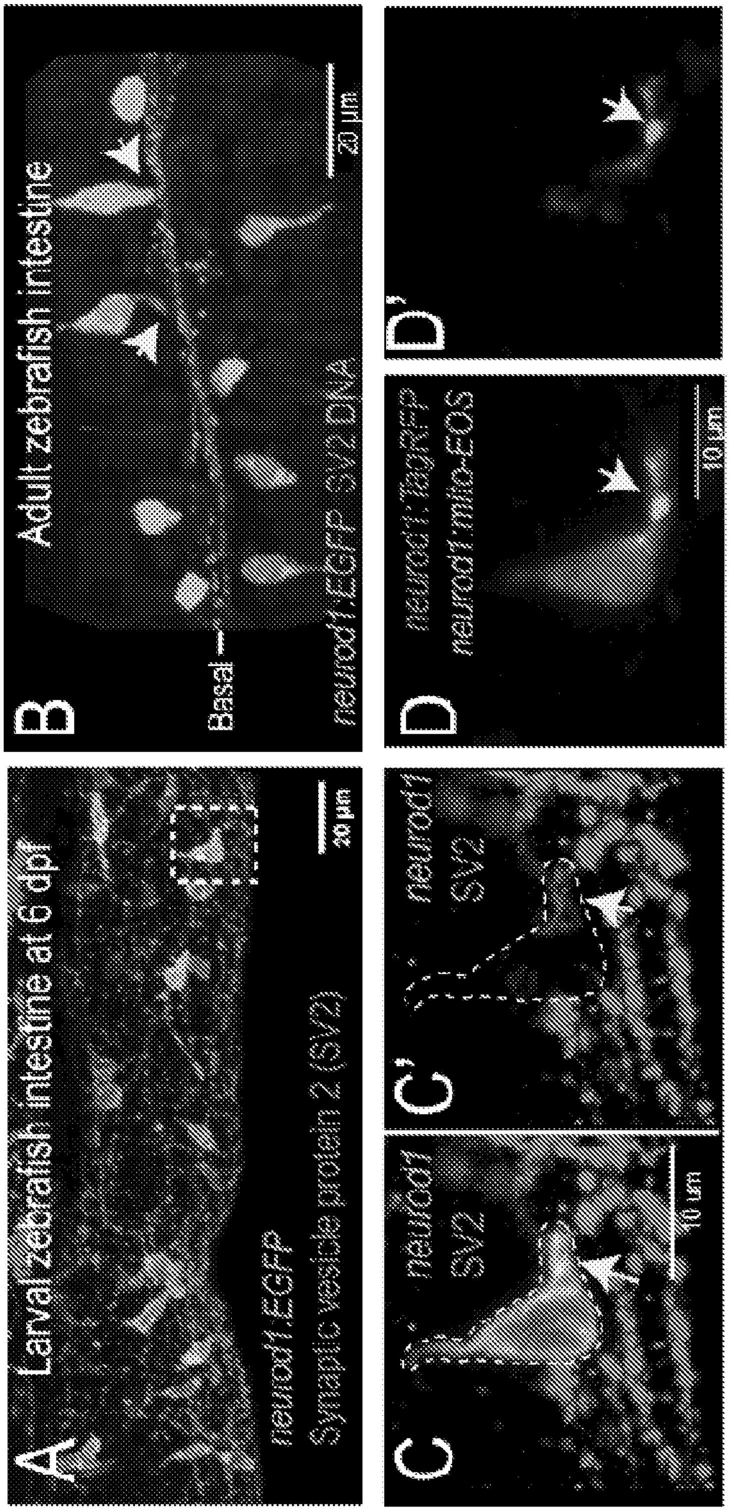
FIG. 10A-D

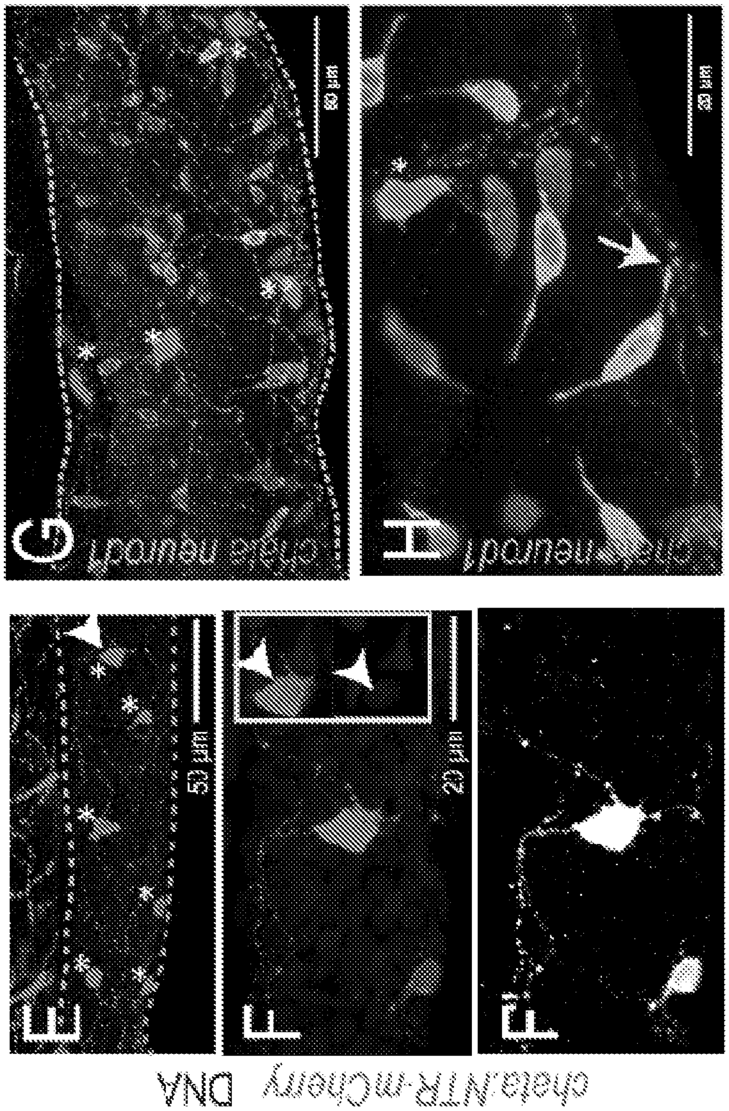
FIG. 10E-H

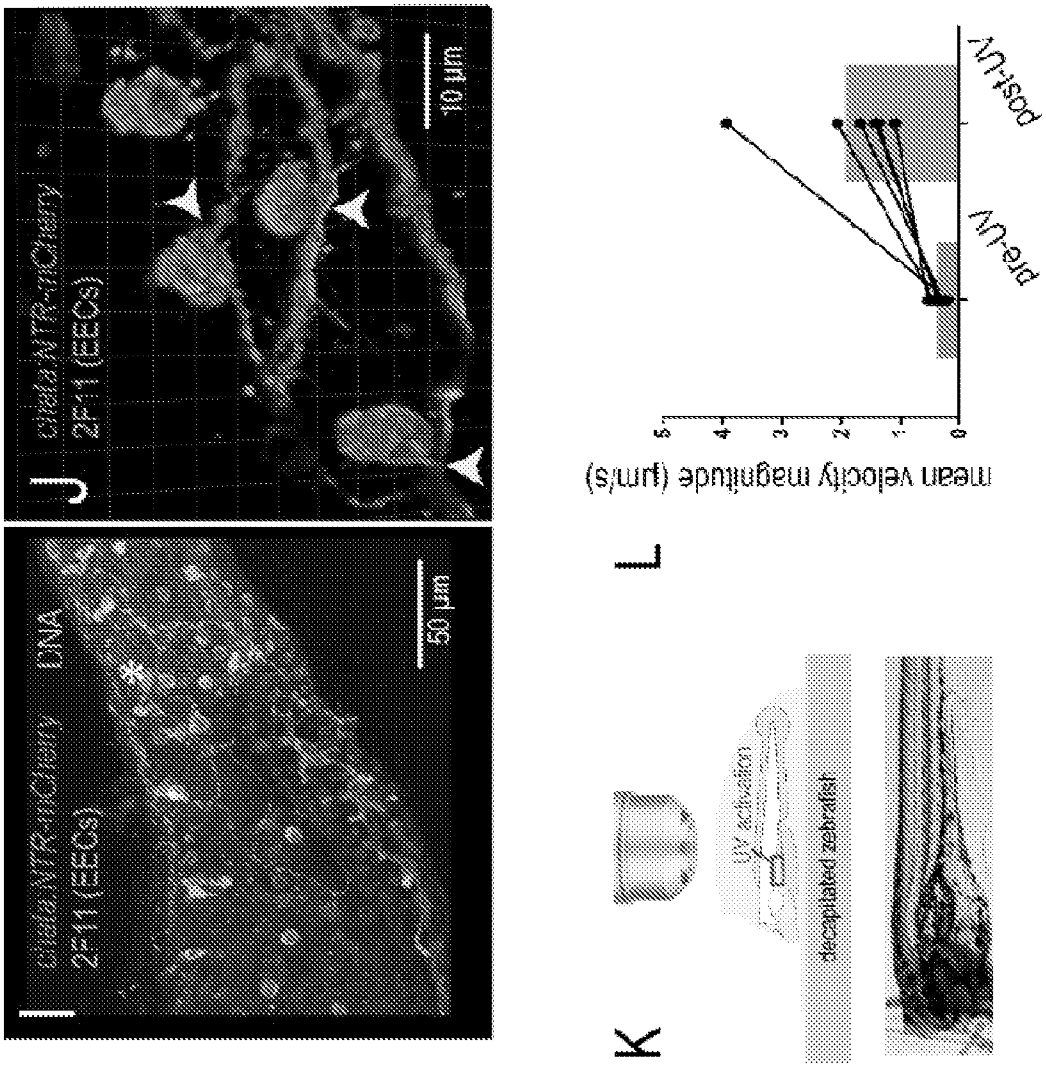
FIG. 10I-L

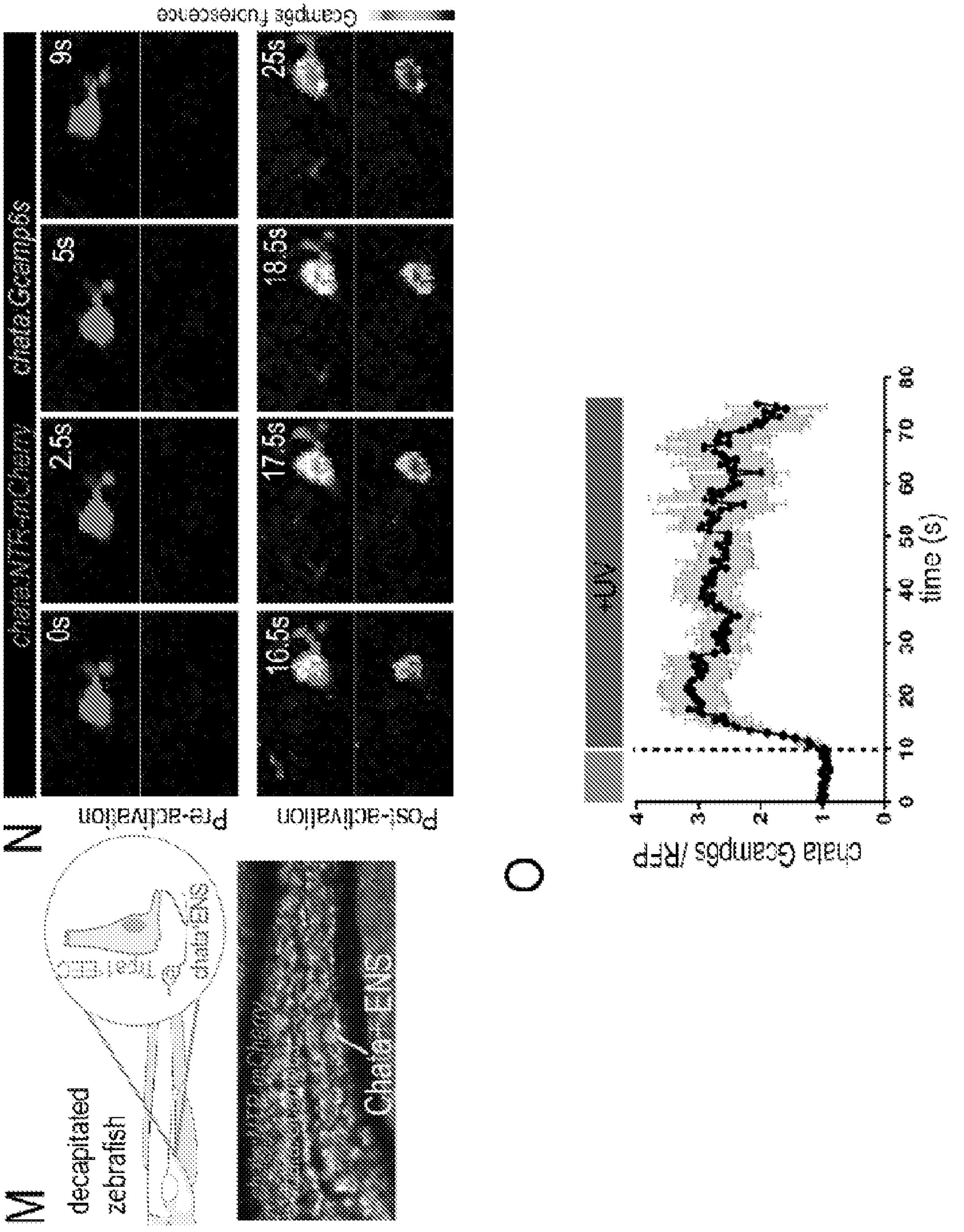
FIG. 10M-O

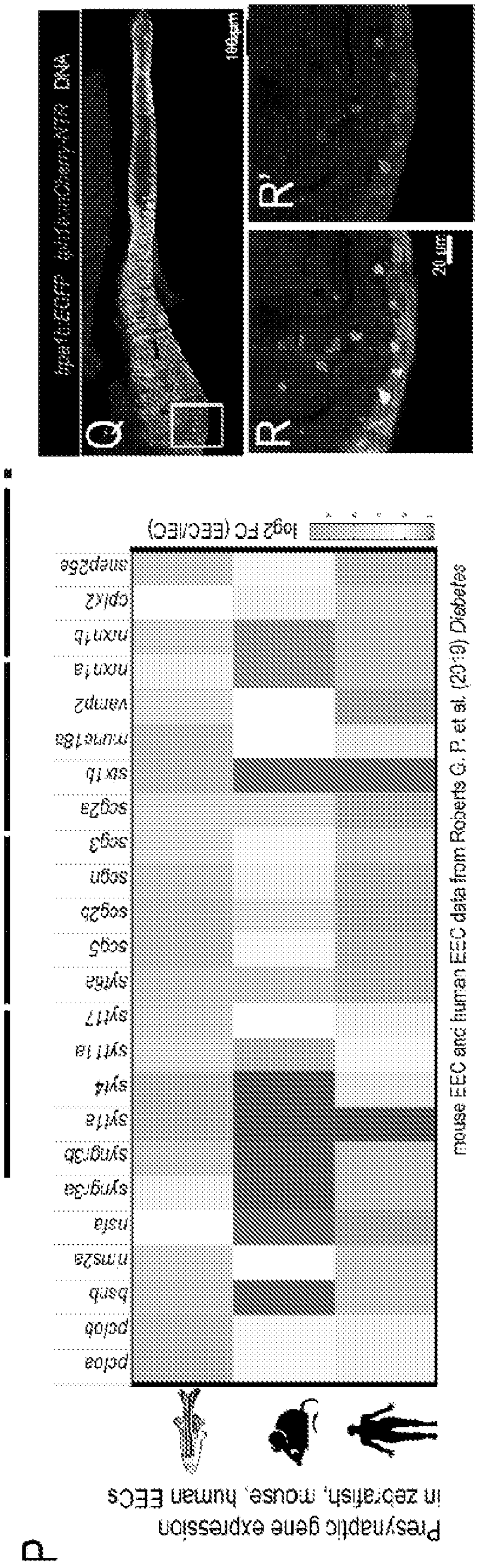
FIG. 10P-R

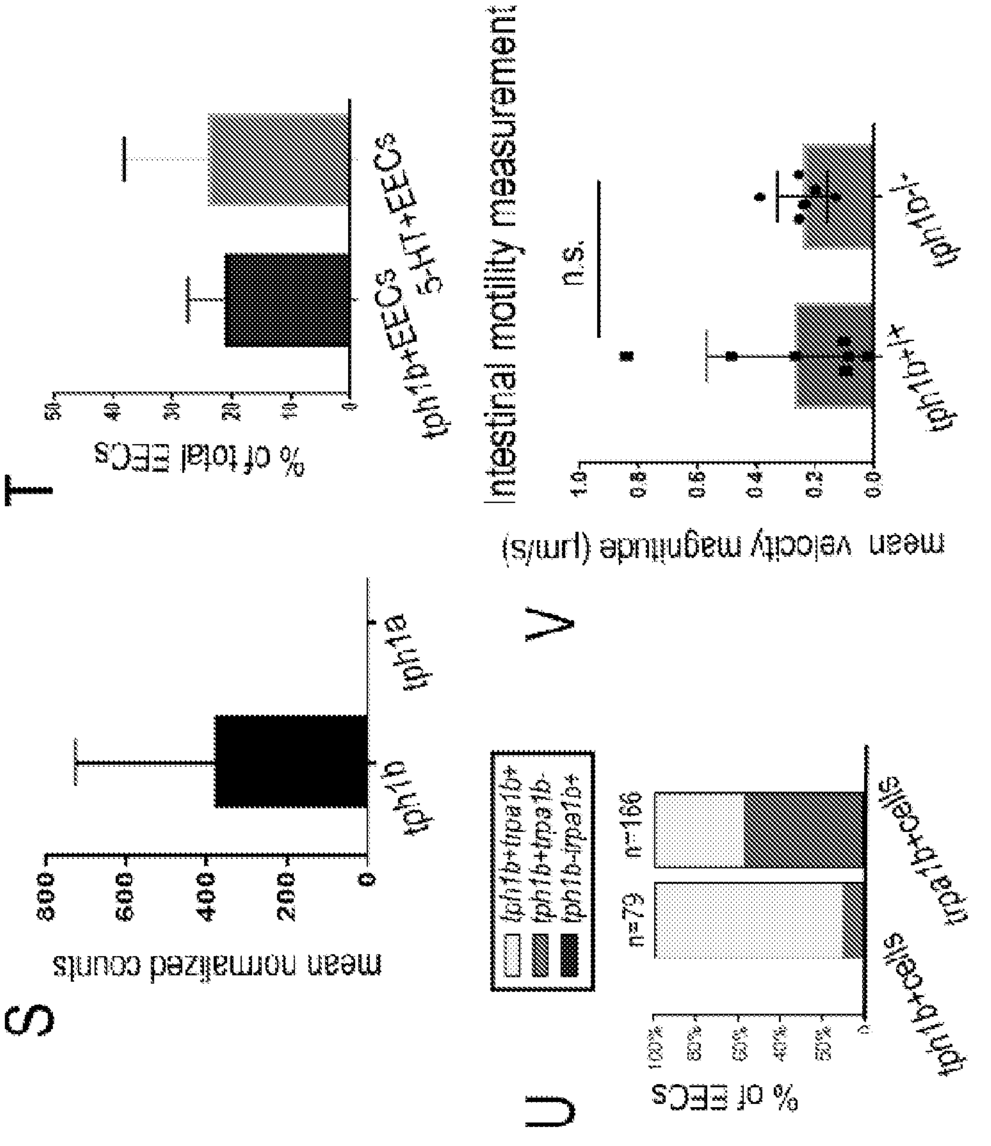
FIG. 10S-V

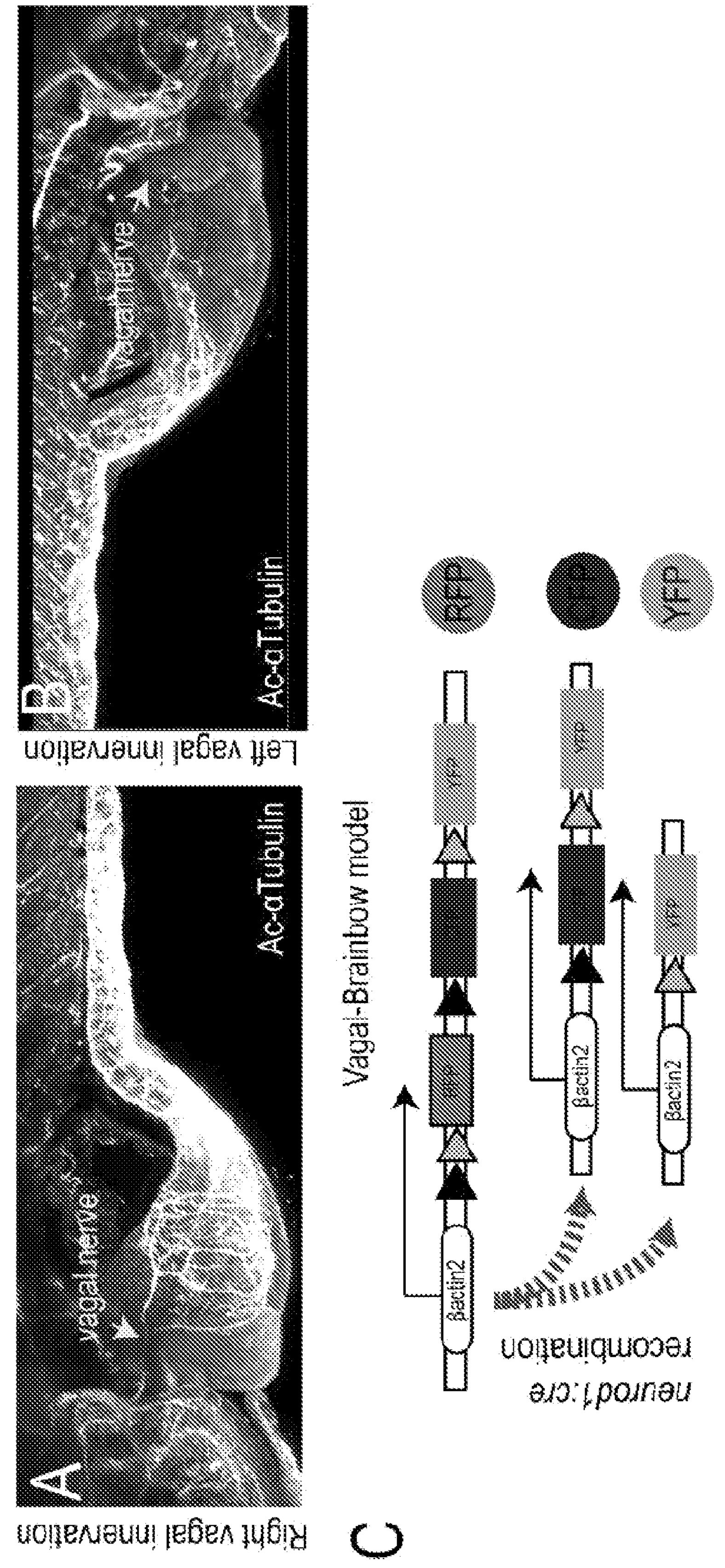
FIG. 11A-C

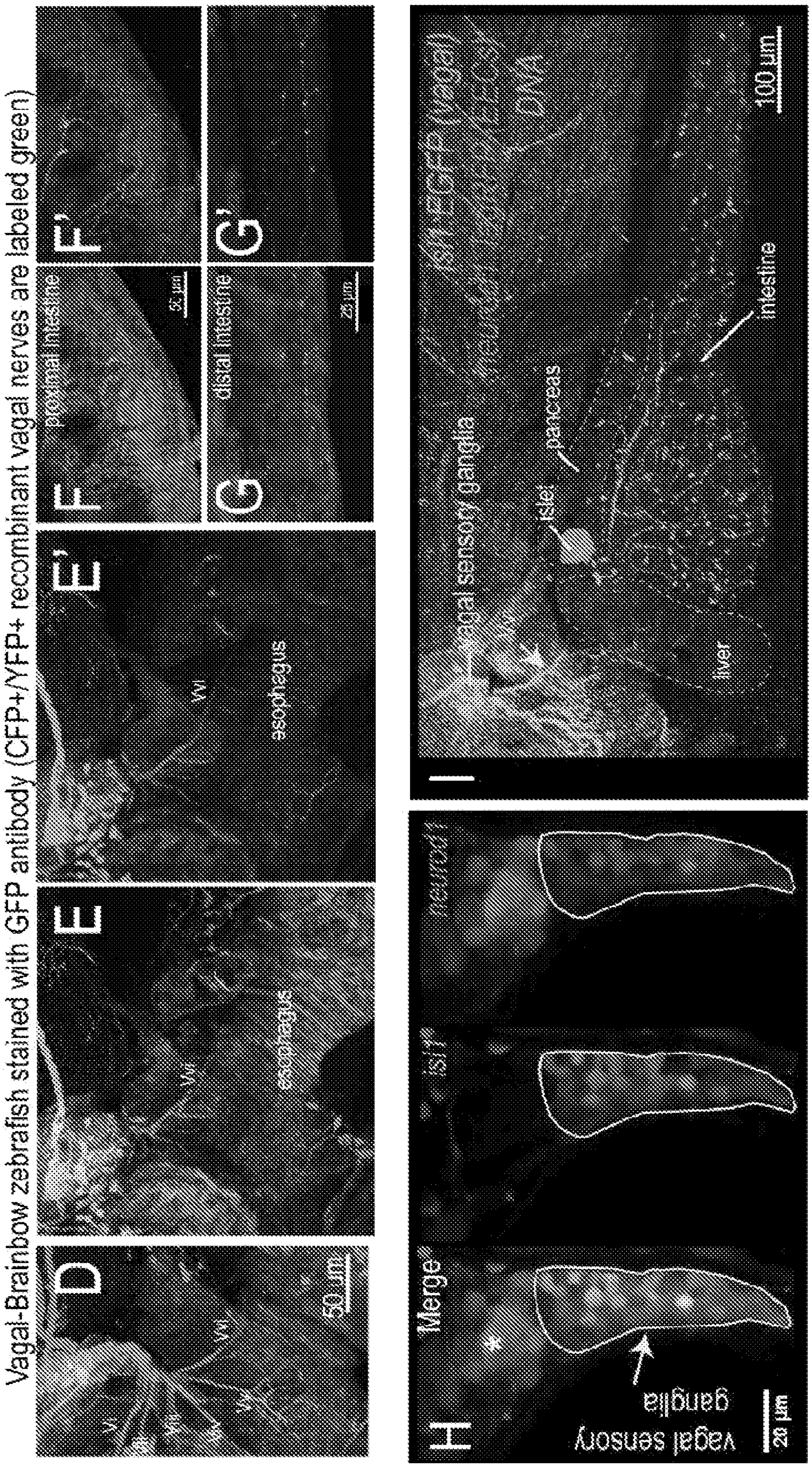
FIG. 11D-I

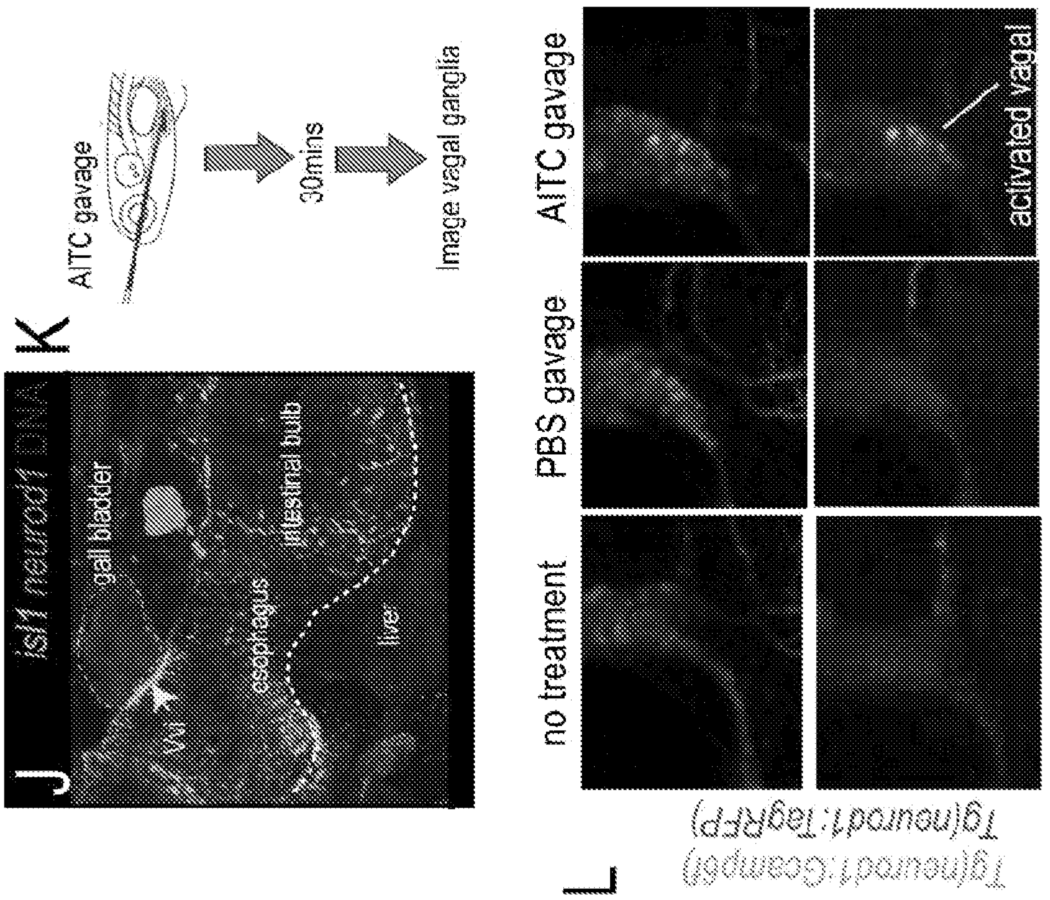
FIG. 11J-L

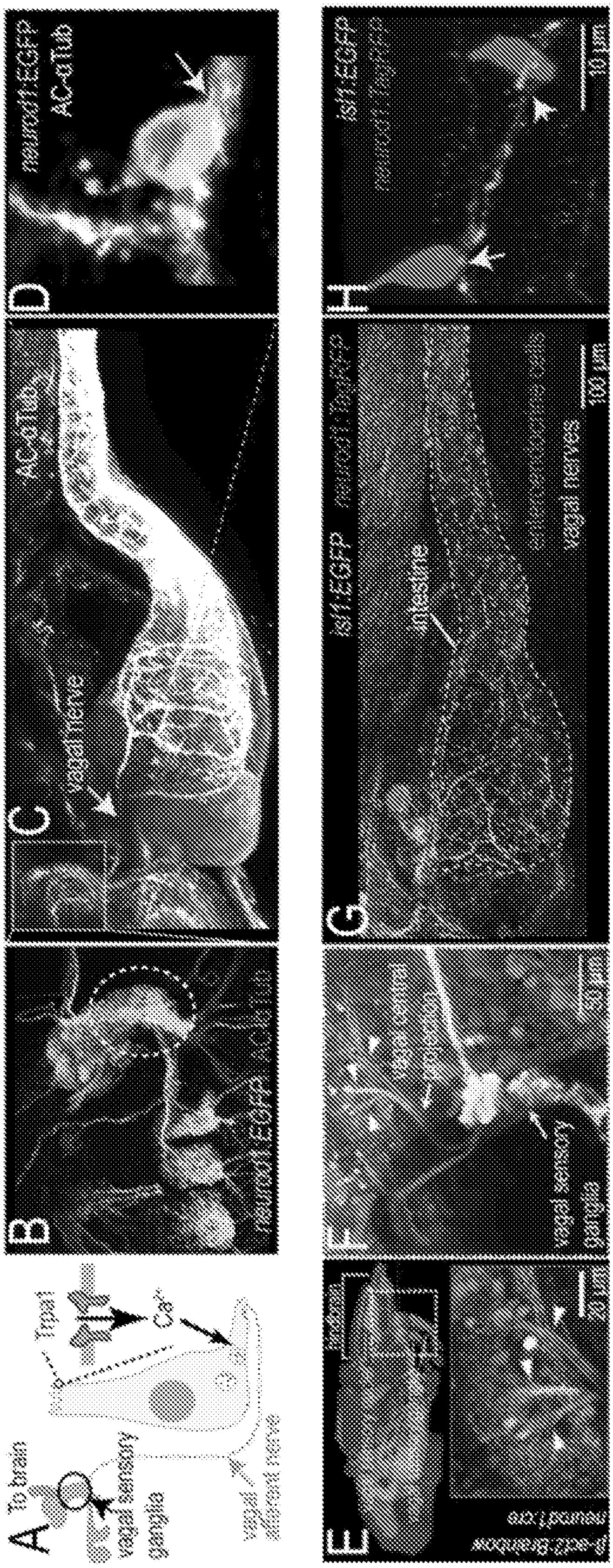
FIG. 12A-H

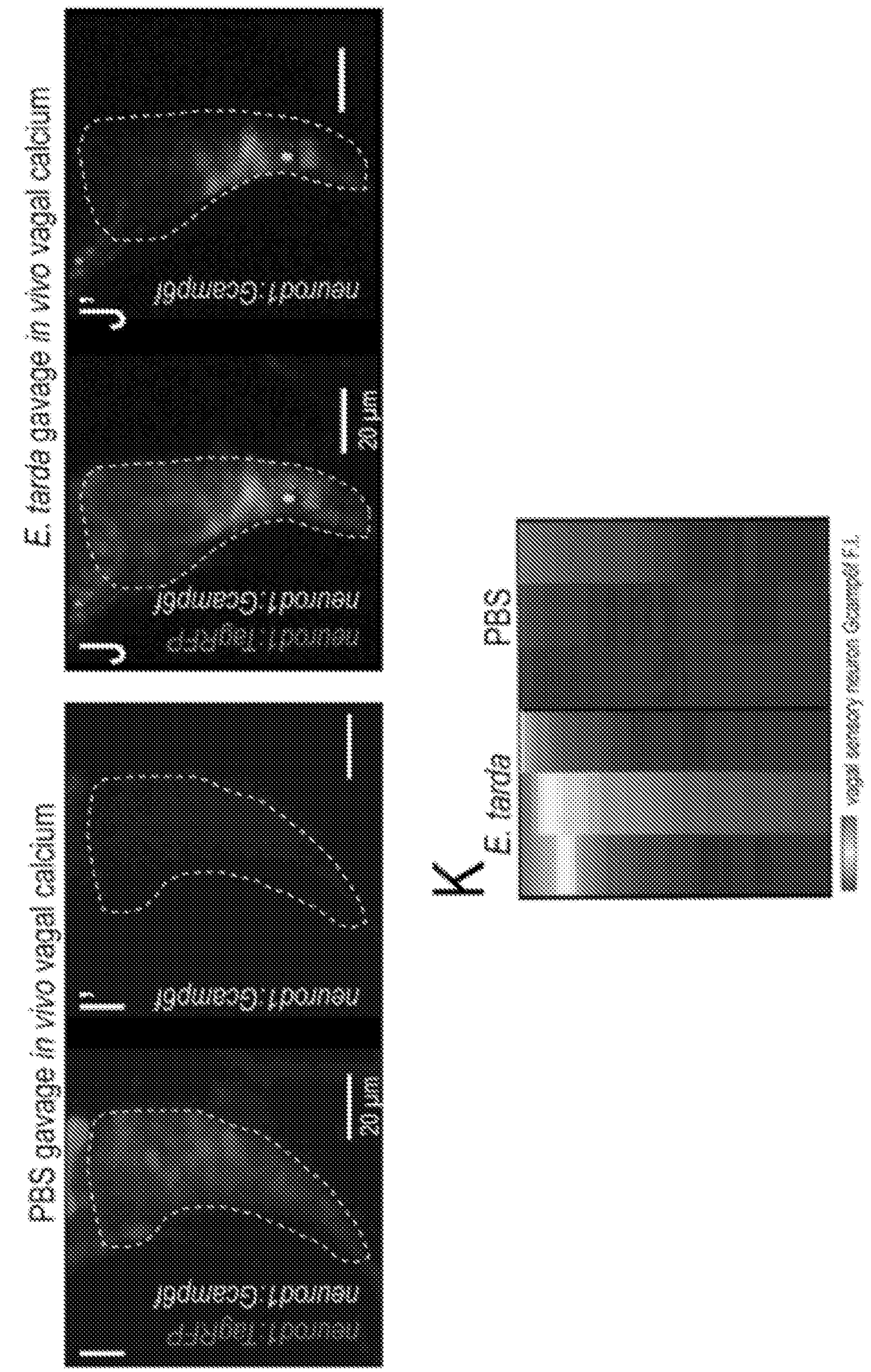
FIG. 12I-K

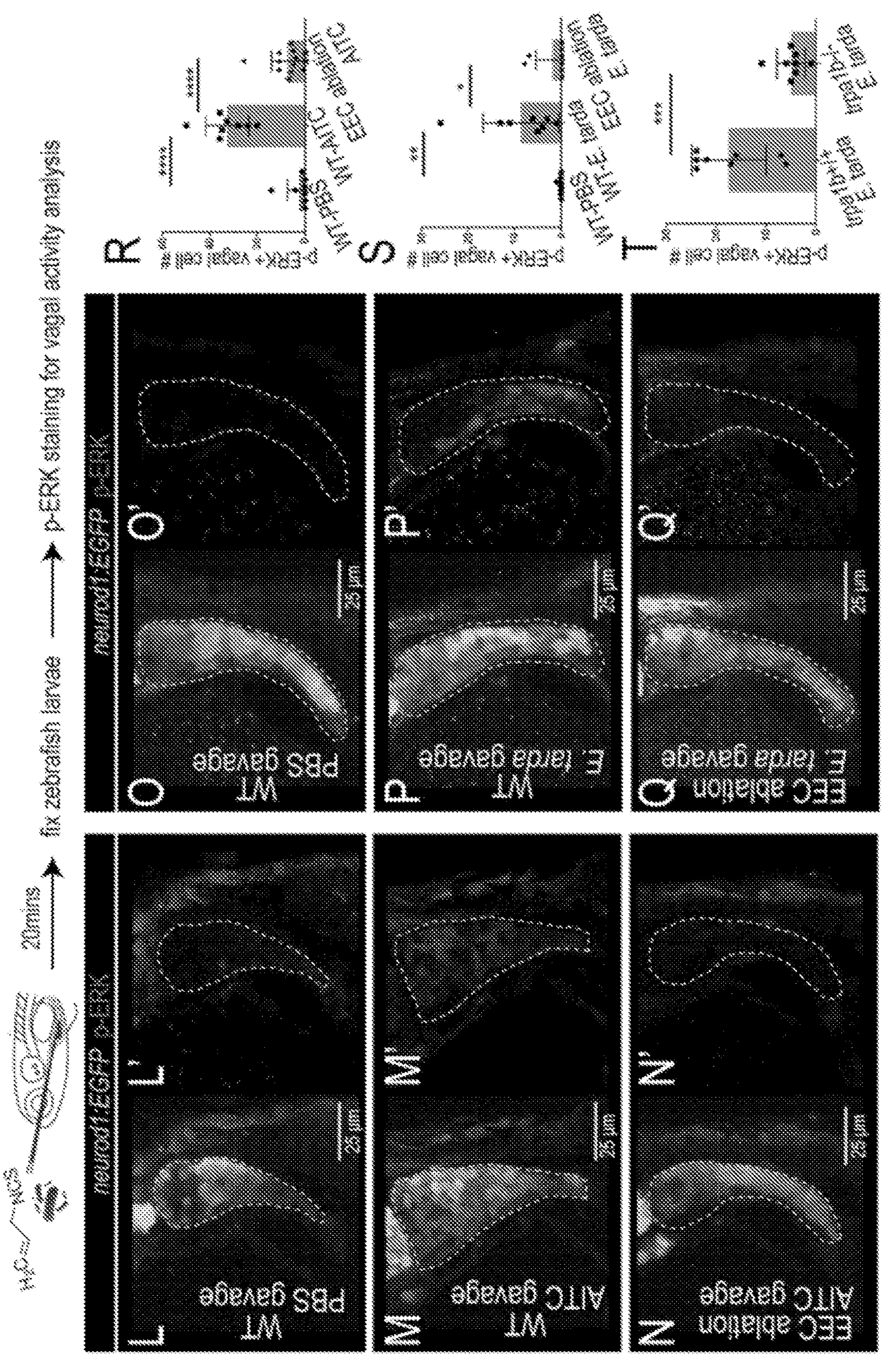
FIG. 12L-T

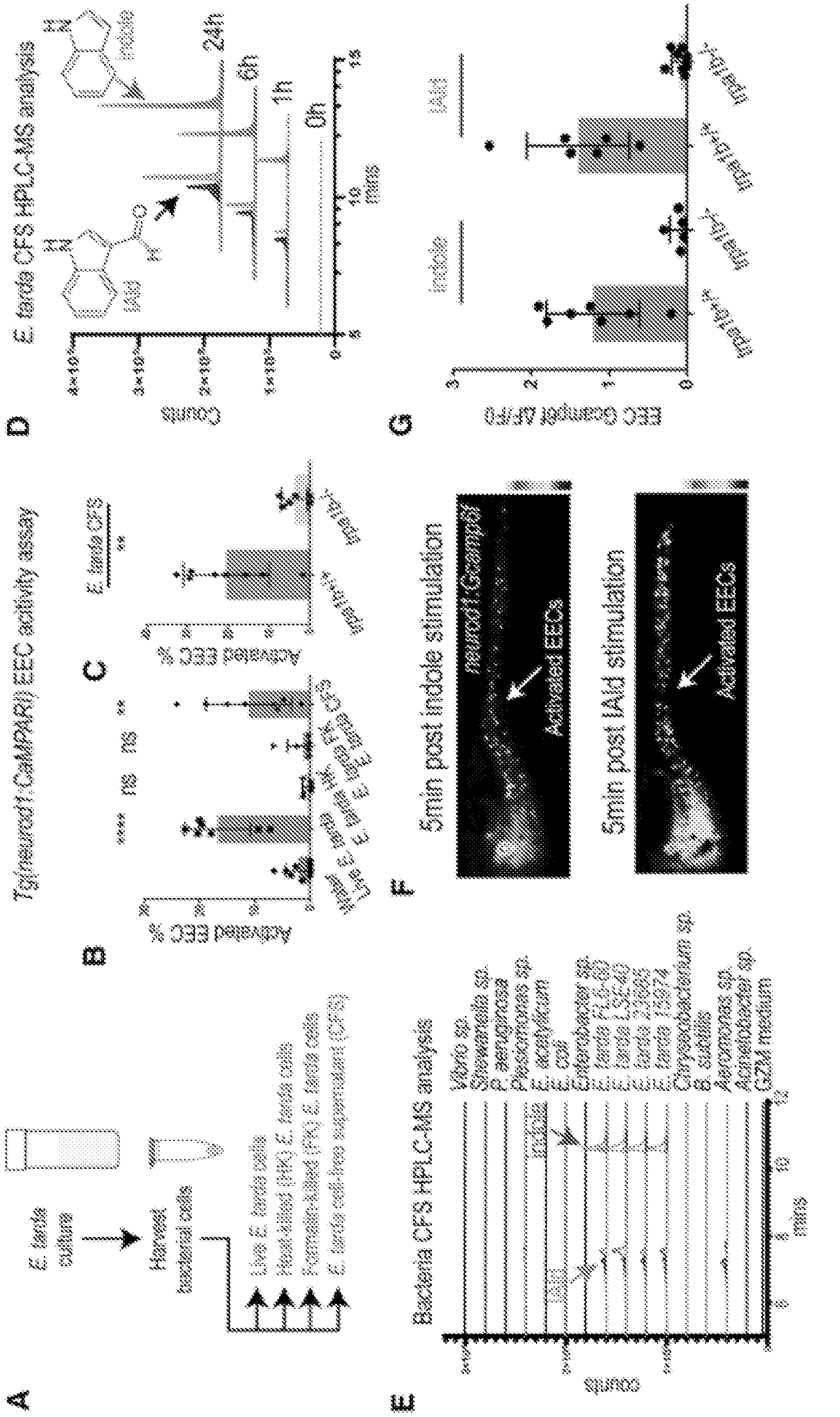
FIG. 13A-G

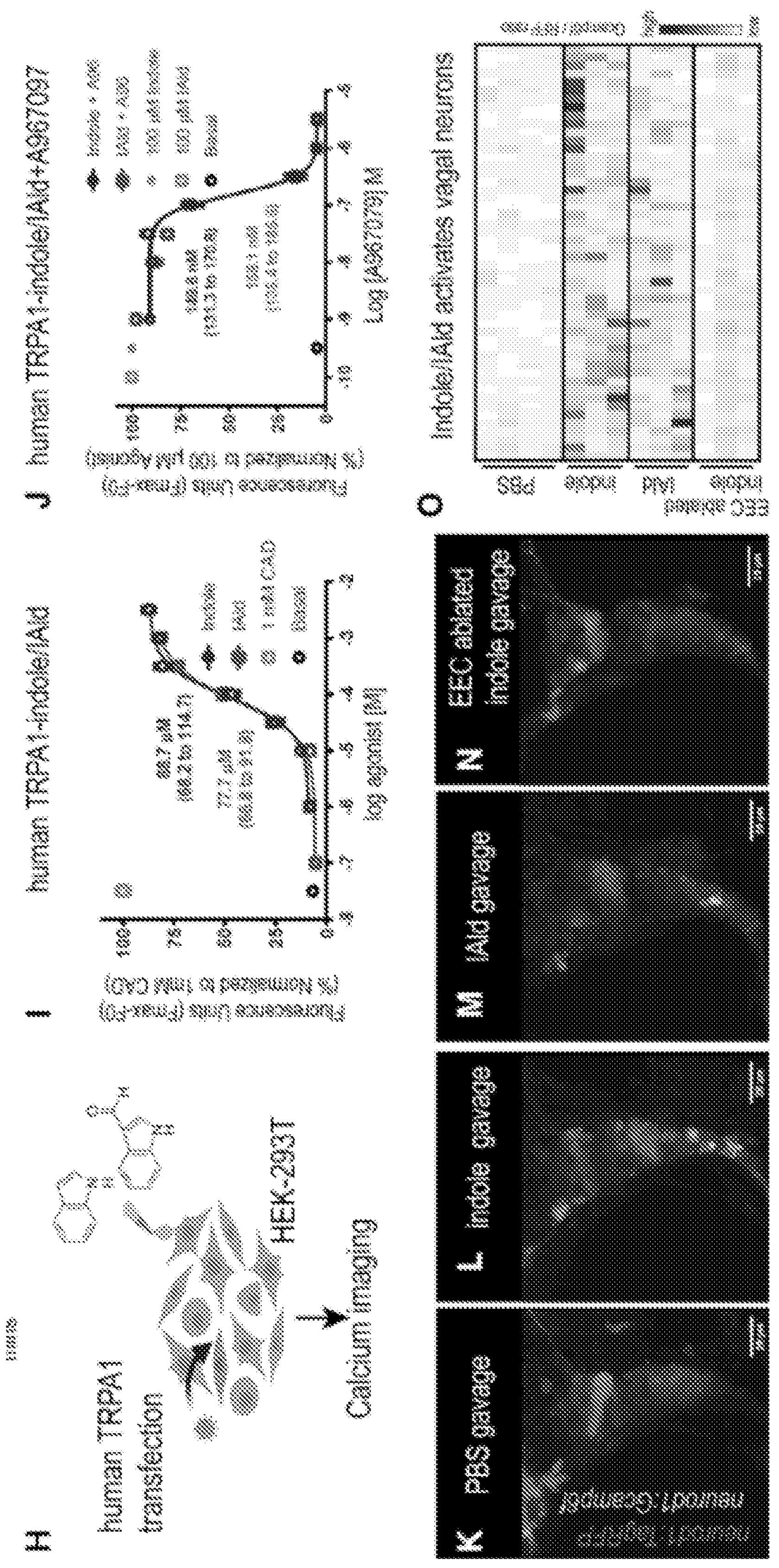
FIG.13H-O

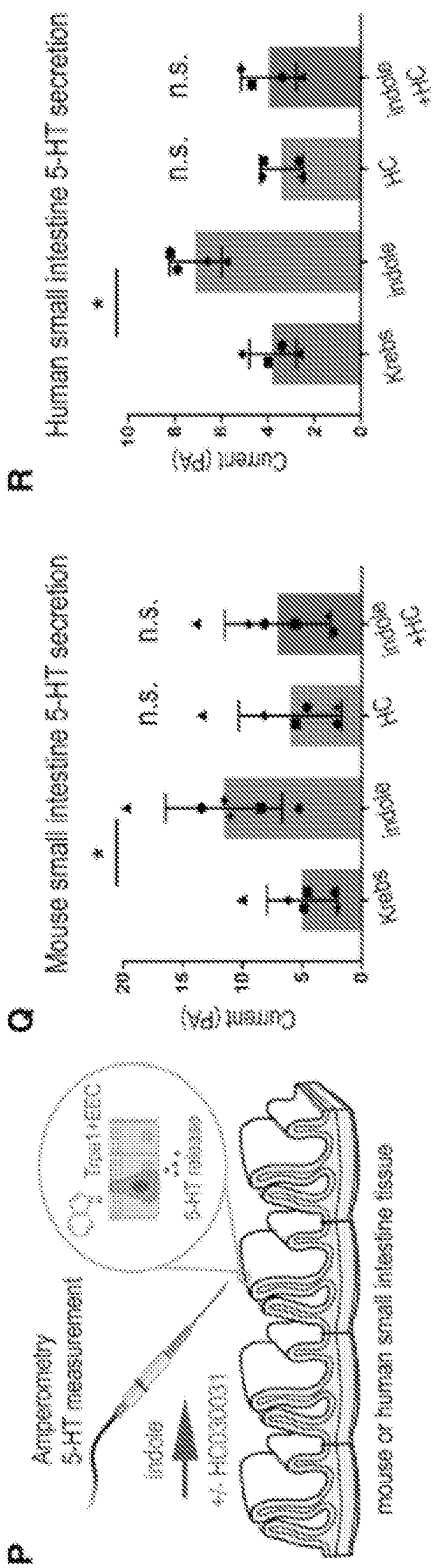
FIG. 13P-R

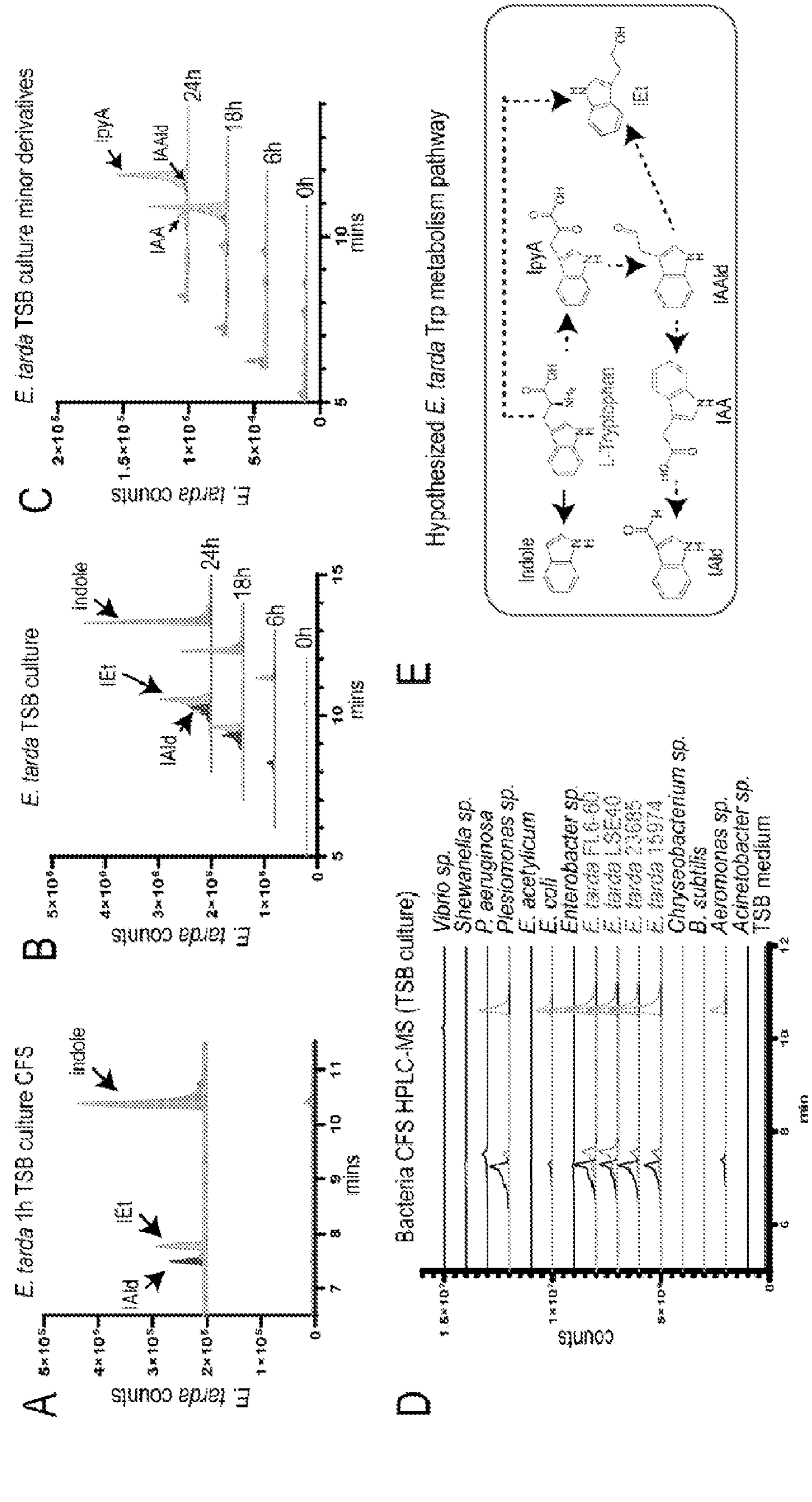
FIG. 14A-E

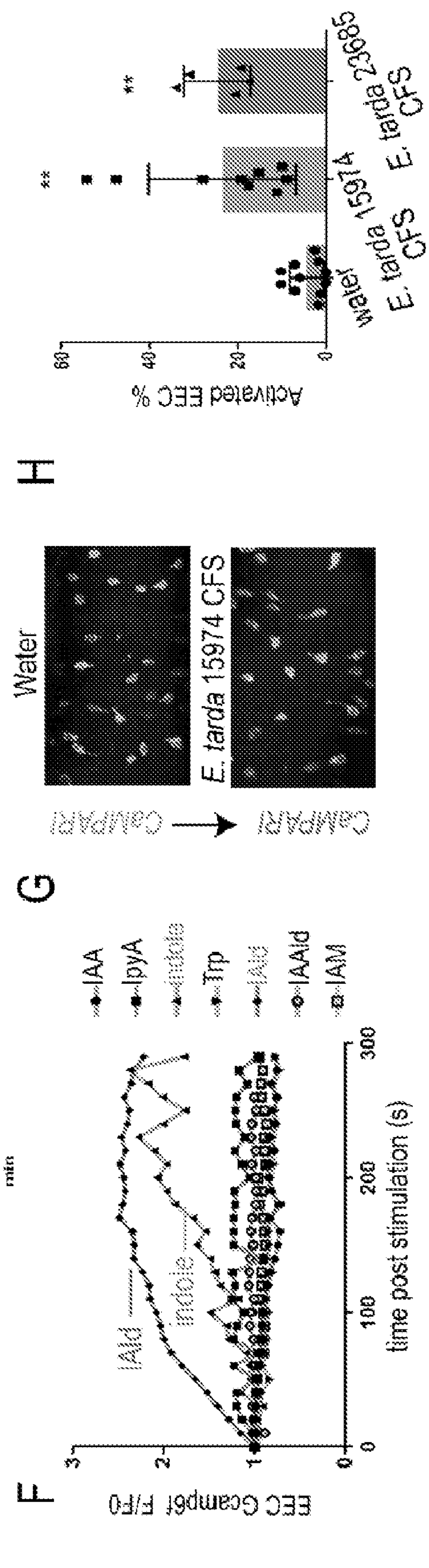
FIG. 14F-H

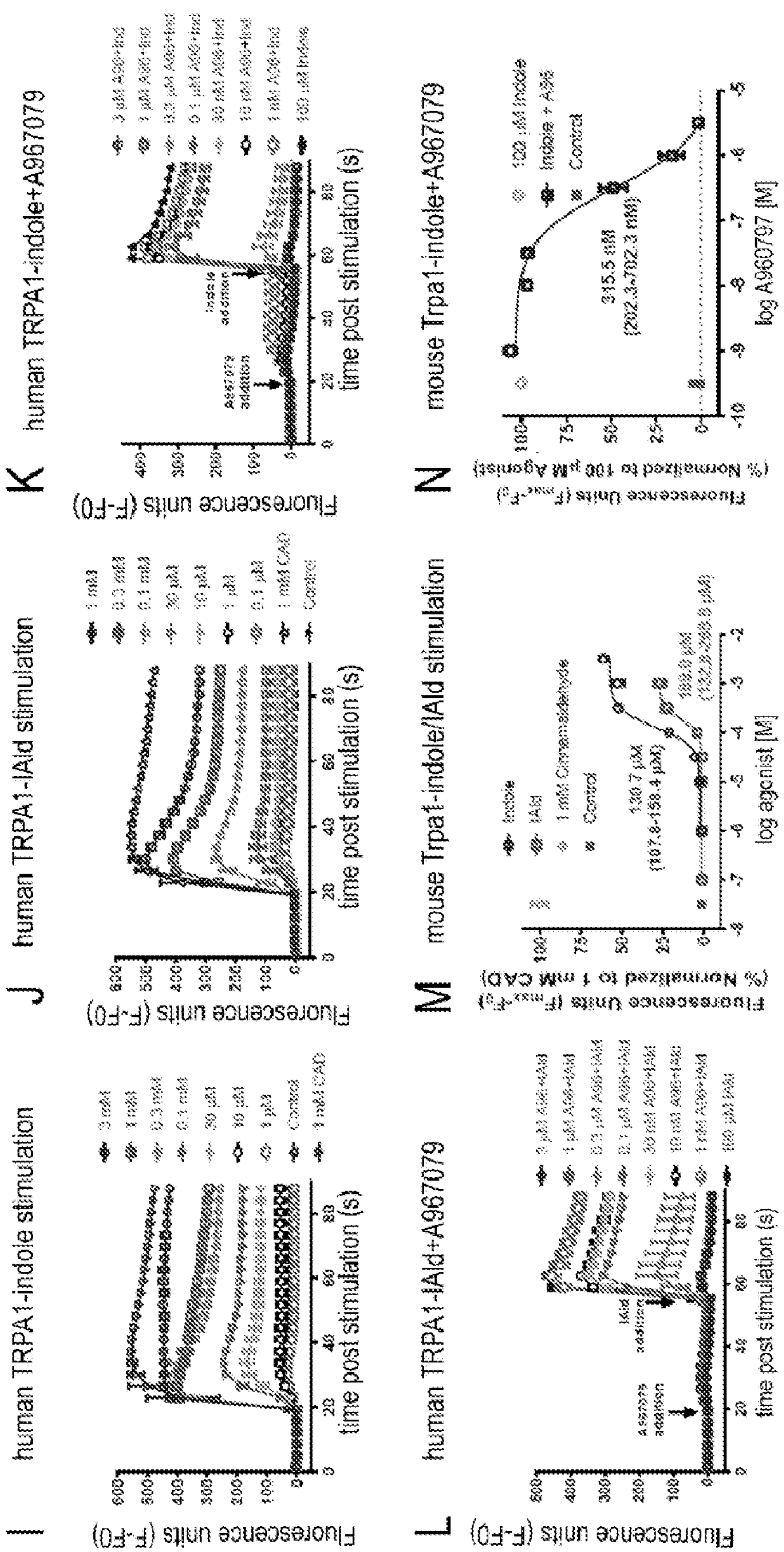
FIG. 14I-N

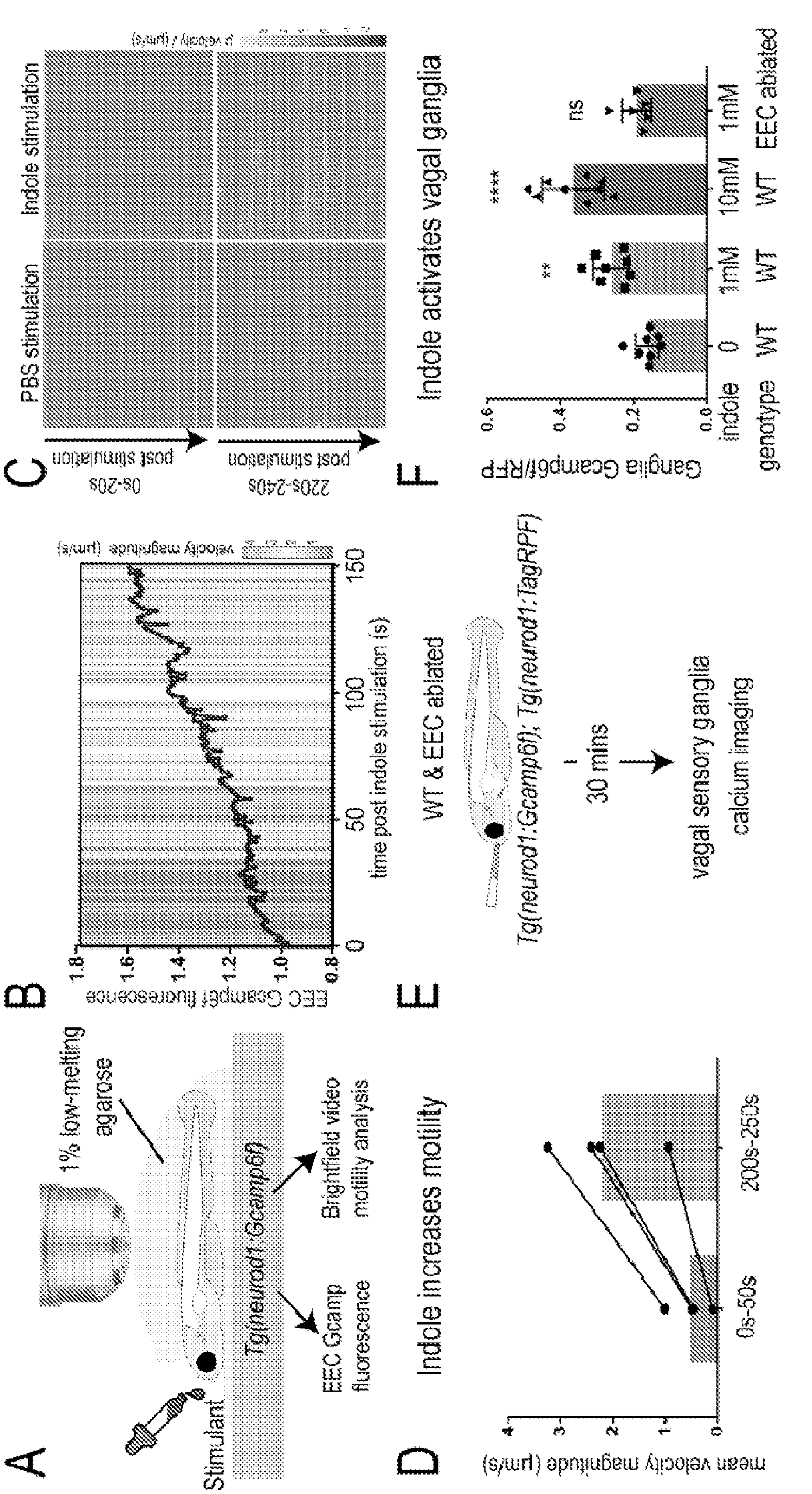
FIG. 15A-F

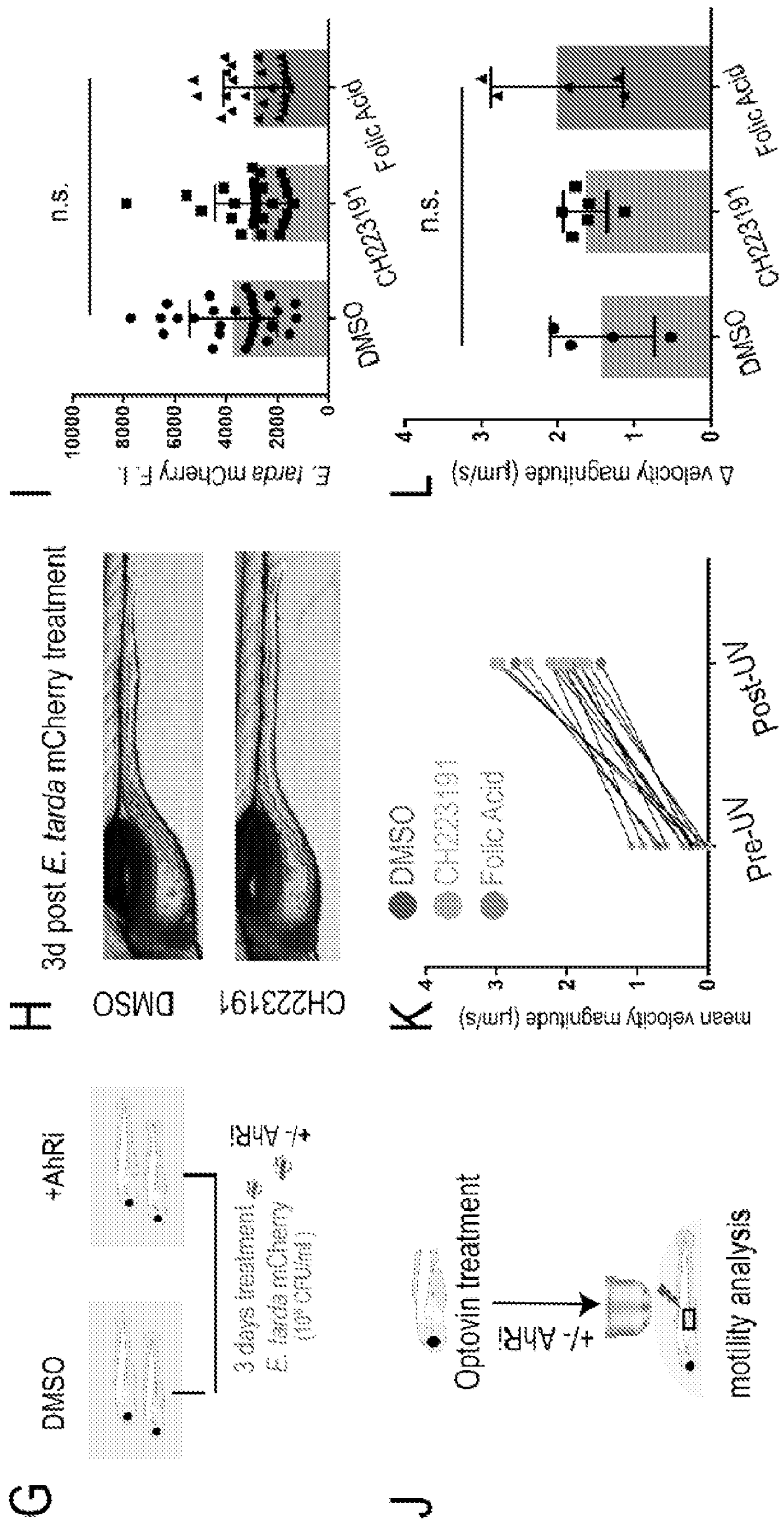
FIG. 15G-L

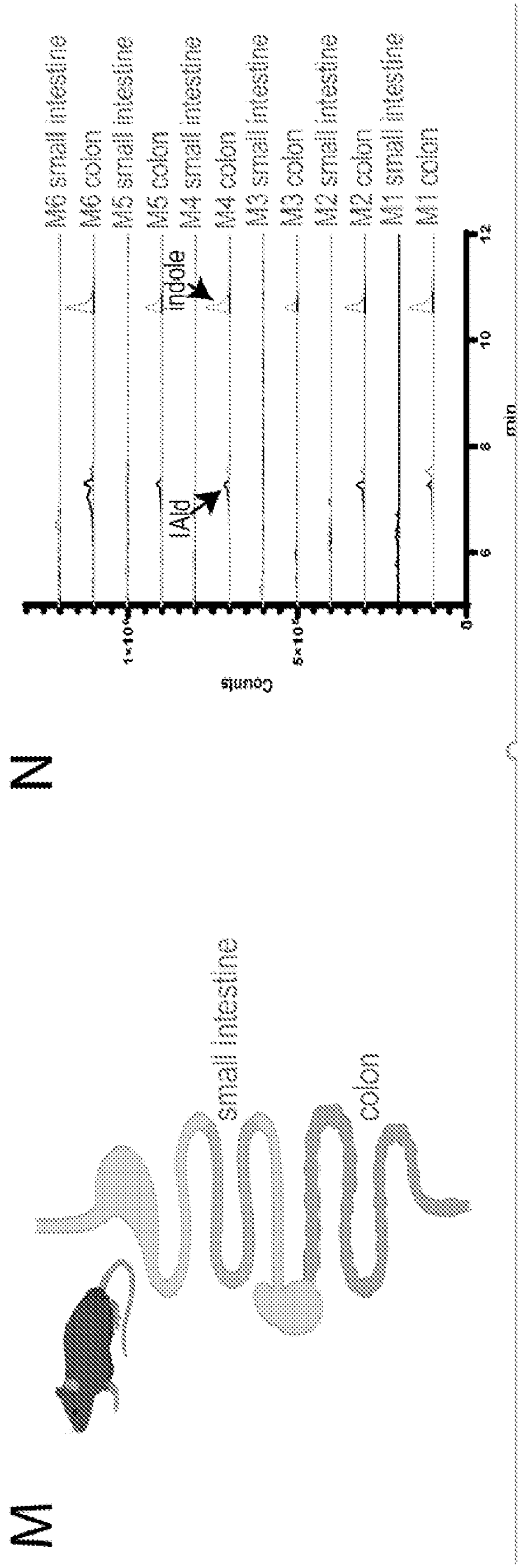
FIG. 15M-N

SEQUENCE LISTING

```
<160> NUMBER OF SEQ ID NOS: 30

<210> SEQ ID NO 1
<211> LENGTH: 20
<212> TYPE: PRT
<213> ORGANISM: Artificial sequence
<220> FEATURE:
<223> OTHER INFORMATION: synthetic

<400> SEQUENCE: 1

Ala Gly Cys Gly Thr Ala Thr Cys Cys Ala Cys Cys Cys Ala Ala Ala
1               5                   10                  15

Cys Cys Thr Gly
            20


<210> SEQ ID NO 2
<211> LENGTH: 20
<212> TYPE: PRT
<213> ORGANISM: Artificial sequence
<220> FEATURE:
<223> OTHER INFORMATION: synthetic

<400> SEQUENCE: 2
```

```
Gly Cys Cys Gly Gly Ala Thr Gly Thr Cys Cys Thr Gly Thr Thr Cys
1               5                   10                  15

Ala Thr Cys Ala
            20


<210> SEQ ID NO 3
<211> LENGTH: 20
<212> TYPE: PRT
<213> ORGANISM: Artificial sequence
<220> FEATURE:
<223> OTHER INFORMATION: synthetic

<400> SEQUENCE: 3

Ala Ala Cys Cys Ala Ala Ala Gly Gly Cys Thr Cys Ala Thr Ala Cys
1               5                   10                  15

Cys Gly Cys Ala
            20


<210> SEQ ID NO 4
<211> LENGTH: 20
<212> TYPE: PRT
<213> ORGANISM: Artificial sequence
<220> FEATURE:
<223> OTHER INFORMATION: synthetic

<400> SEQUENCE: 4

Thr Cys Ala Thr Ala Thr Thr Cys Cys Thr Cys Gly Gly Cys Gly Cys
1               5                   10                  15

Thr Thr Cys Gly
            20


<210> SEQ ID NO 5
<211> LENGTH: 20
<212> TYPE: PRT
<213> ORGANISM: Artificial sequence
<220> FEATURE:
<223> OTHER INFORMATION: synthetic

<400> SEQUENCE: 5

Gly Gly Gly Gly Thr Thr Thr Thr Cys Ala Cys Gly Gly Ala Cys Ala
1               5                   10                  15

Gly Cys Thr Ala
            20


<210> SEQ ID NO 6
<211> LENGTH: 20
<212> TYPE: PRT
<213> ORGANISM: Artificial sequence
<220> FEATURE:
<223> OTHER INFORMATION: synthetic

<400> SEQUENCE: 6

Thr Gly Thr Gly Thr Cys Ala Cys Ala Ala Ala Gly Cys Cys Gly Gly
1               5                   10                  15

Gly Ala Ala Thr
            20


<210> SEQ ID NO 7
<211> LENGTH: 20
<212> TYPE: PRT
<213> ORGANISM: Artificial sequence
<220> FEATURE:
<223> OTHER INFORMATION: synthetic
```

<400> SEQUENCE: 7

Thr Gly Cys Thr Gly Thr Ala Ala Gly Cys Ala Gly Ala Cys Gly Ala
1 5 10 15

Gly Ala Cys Cys
20

<210> SEQ ID NO 8
<211> LENGTH: 20
<212> TYPE: PRT
<213> ORGANISM: Artificial sequence
<220> FEATURE:
<223> OTHER INFORMATION: synthetic

<400> SEQUENCE: 8

Ala Gly Cys Ala Gly Ala Gly Gly Ala Ala Cys Gly Thr Cys Ala Gly
1 5 10 15

Gly Thr Cys Ala
20

<210> SEQ ID NO 9
<211> LENGTH: 20
<212> TYPE: PRT
<213> ORGANISM: Artificial sequence
<220> FEATURE:
<223> OTHER INFORMATION: synthetic

<400> SEQUENCE: 9

Thr Gly Gly Ala Ala Ala Gly Thr Cys Gly Ala Cys Cys Gly Cys Ala
1 5 10 15

Ala Thr Gly Ala
20

<210> SEQ ID NO 10
<211> LENGTH: 20
<212> TYPE: PRT
<213> ORGANISM: Artificial sequence
<220> FEATURE:
<223> OTHER INFORMATION: synthetic

<400> SEQUENCE: 10

Thr Gly Ala Ala Cys Thr Thr Gly Thr Cys Thr Cys Cys Gly Gly Thr
1 5 10 15

Cys Thr Gly Cys
20

<210> SEQ ID NO 11
<211> LENGTH: 20
<212> TYPE: PRT
<213> ORGANISM: Artificial sequence
<220> FEATURE:
<223> OTHER INFORMATION: synthetic

<400> SEQUENCE: 11

Ala Thr Gly Cys Gly Ala Ala Cys Cys Ala Thr Gly Gly Gly Gly Cys
1 5 10 15

Thr Thr Thr Ala
20

<210> SEQ ID NO 12
<211> LENGTH: 20
<212> TYPE: PRT
<213> ORGANISM: Artificial sequence
<220> FEATURE:
<223> OTHER INFORMATION: synthetic -continued

<400> SEQUENCE: 12

```
Thr Thr Gly Thr Thr Cys Gly Cys Gly Thr Thr Cys Cys Cys Gly Thr
1               5                   10                  15

Cys Ala Thr Ala
            20
```

<210> SEQ ID NO 13
<211> LENGTH: 20
<212> TYPE: PRT
<213> ORGANISM: Artificial sequence
<220> FEATURE:
<223> OTHER INFORMATION: synthetic

<400> SEQUENCE: 13

```
Gly Ala Thr Cys Gly Thr Gly Gly Cys Ala Cys Cys Gly Thr Thr Thr
1               5                   10                  15

Ala Thr Gly Cys
            20
```

<210> SEQ ID NO 14
<211> LENGTH: 20
<212> TYPE: PRT
<213> ORGANISM: Artificial sequence
<220> FEATURE:
<223> OTHER INFORMATION: synthetic

<400> SEQUENCE: 14

```
Ala Thr Thr Gly Thr Ala Gly Cys Cys Thr Thr Gly Cys Thr Gly Gly
1               5                   10                  15

Cys Thr Gly Thr
            20
```

<210> SEQ ID NO 15
<211> LENGTH: 20
<212> TYPE: PRT
<213> ORGANISM: Artificial sequence
<220> FEATURE:
<223> OTHER INFORMATION: synthetic

<400> SEQUENCE: 15

```
Ala Thr Cys Cys Thr Ala Thr Gly Gly Gly Gly Ala Gly Gly Cys Ala
1               5                   10                  15

Ala Cys Cys Thr
            20
```

<210> SEQ ID NO 16
<211> LENGTH: 20
<212> TYPE: PRT
<213> ORGANISM: Artificial sequence
<220> FEATURE:
<223> OTHER INFORMATION: synthetic

<400> SEQUENCE: 16

```
Ala Cys Cys Thr Thr Cys Cys Thr Gly Thr Cys Cys Ala Thr Ala Gly
1               5                   10                  15

Cys Cys Cys Thr
            20
```

<210> SEQ ID NO 17
<211> LENGTH: 20
<212> TYPE: PRT
<213> ORGANISM: Artificial sequence
<220> FEATURE:

-continued

```
<223> OTHER INFORMATION: synthetic

<400> SEQUENCE: 17

Ala Gly Thr Gly Cys Thr Cys Thr Thr Gly Gly Thr Cys Ala Thr Gly
1               5                   10                  15

Gly Thr Gly Gly
            20


<210> SEQ ID NO 18
<211> LENGTH: 20
<212> TYPE: PRT
<213> ORGANISM: Artificial sequence
<220> FEATURE:
<223> OTHER INFORMATION: synthetic

<400> SEQUENCE: 18

Ala Gly Gly Gly Gly Cys Thr Thr Gly Thr Thr Cys Thr Thr Gly Gly
1               5                   10                  15

Ala Thr Cys Gly
            20


<210> SEQ ID NO 19
<211> LENGTH: 24
<212> TYPE: PRT
<213> ORGANISM: Artificial sequence
<220> FEATURE:
<223> OTHER INFORMATION: synthetic

<400> SEQUENCE: 19

Thr Ala Cys Cys Ala Ala Cys Ala Thr Gly Thr Cys Gly Thr Gly Thr
1               5                   10                  15

Thr Thr Thr Cys Ala Gly Thr Gly
            20


<210> SEQ ID NO 20
<211> LENGTH: 22
<212> TYPE: PRT
<213> ORGANISM: Artificial sequence
<220> FEATURE:
<223> OTHER INFORMATION: synthetic

<400> SEQUENCE: 20

Gly Ala Thr Thr Gly Cys Ala Cys Ala Cys Ala Ala Cys Cys Gly Gly
1               5                   10                  15

Thr Thr Thr Ala Cys Ala
            20


<210> SEQ ID NO 21
<211> LENGTH: 23
<212> TYPE: PRT
<213> ORGANISM: Artificial sequence
<220> FEATURE:
<223> OTHER INFORMATION: synthetic

<400> SEQUENCE: 21

Cys Thr Cys Ala Thr Thr Thr Gly Thr Cys Thr Thr Gly Gly Ala Ala
1               5                   10                  15

Ala Gly Gly Gly Ala Gly Cys
            20


<210> SEQ ID NO 22
<211> LENGTH: 20
<212> TYPE: PRT
<213> ORGANISM: Artificial sequence
```

-continued

```
<220> FEATURE:
<223> OTHER INFORMATION: synthetic

<400> SEQUENCE: 22

Gly Gly Ala Gly Gly Ala Ala Gly Thr Thr Gly Cys Gly Ala Cys Cys
1               5                   10                  15

Thr Gly Thr Thr
            20


<210> SEQ ID NO 23
<211> LENGTH: 35
<212> TYPE: PRT
<213> ORGANISM: Artificial sequence
<220> FEATURE:
<223> OTHER INFORMATION: synthetic

<400> SEQUENCE: 23

Gly Gly Thr Cys Thr Cys Gly Ala Thr Cys Gly Gly Thr Cys Thr Ala
1               5                   10                  15

Ala Gly Gly Thr Gly Ala Ala Thr Cys Thr Gly Thr Cys Ala Cys Ala
            20                  25                  30

Thr Thr Cys
        35


<210> SEQ ID NO 24
<211> LENGTH: 35
<212> TYPE: PRT
<213> ORGANISM: Artificial sequence
<220> FEATURE:
<223> OTHER INFORMATION: synthetic

<400> SEQUENCE: 24

Gly Gly Thr Cys Thr Cys Gly Gly Cys Thr Ala Cys Gly Gly Ala Thr
1               5                   10                  15

Gly Gly Ala Thr Gly Cys Thr Cys Thr Thr Gly Thr Thr Thr Thr Ala
            20                  25                  30

Thr Ala Gly
        35


<210> SEQ ID NO 25
<211> LENGTH: 29
<212> TYPE: PRT
<213> ORGANISM: Artificial sequence
<220> FEATURE:
<223> OTHER INFORMATION: synthetic

<400> SEQUENCE: 25

Gly Gly Thr Cys Thr Cys Gly Thr Ala Gly Cys Cys Gly Cys Cys Gly
1               5                   10                  15

Cys Cys Ala Cys Cys Ala Thr Gly Gly Thr Gly Ala Gly
            20                  25


<210> SEQ ID NO 26
<211> LENGTH: 36
<212> TYPE: PRT
<213> ORGANISM: Artificial sequence
<220> FEATURE:
<223> OTHER INFORMATION: synthetic

<400> SEQUENCE: 26

Gly Gly Thr Cys Thr Cys Gly Gly Thr Ala Cys Cys Cys Thr Thr Gly
1               5                   10                  15

Thr Ala Cys Ala Gly Cys Thr Cys Gly Thr Cys Cys Ala Thr Gly Cys
```

-continued

```
            20                  25                  30

Cys Gly Cys Cys
        35


<210> SEQ ID NO 27
<211> LENGTH: 35
<212> TYPE: PRT
<213> ORGANISM: Artificial sequence
<220> FEATURE:
<223> OTHER INFORMATION: synthetic

<400> SEQUENCE: 27

Gly Gly Thr Cys Thr Cys Gly Gly Thr Ala Cys Cys Thr Ala Cys Thr
1               5                   10                  15

Thr Gly Thr Ala Cys Ala Ala Gly Gly Gly Ala Ala Gly Cys Gly Gly
            20                  25                  30

Ala Gly Cys
        35


<210> SEQ ID NO 28
<211> LENGTH: 31
<212> TYPE: PRT
<213> ORGANISM: Artificial sequence
<220> FEATURE:
<223> OTHER INFORMATION: synthetic

<400> SEQUENCE: 28

Gly Gly Thr Cys Thr Cys Cys Cys Ala Thr Gly Cys Cys Ala Gly Gly
1               5                   10                  15

Ala Thr Cys Gly Gly Thr Cys Gly Thr Gly Cys Thr Cys Gly Ala
            20                  25                  30


<210> SEQ ID NO 29
<211> LENGTH: 31
<212> TYPE: PRT
<213> ORGANISM: Artificial sequence
<220> FEATURE:
<223> OTHER INFORMATION: synthetic

<400> SEQUENCE: 29

Gly Gly Thr Cys Thr Cys Gly Cys Ala Thr Gly Gly Ala Cys Ala Cys
1               5                   10                  15

Cys Thr Cys Cys Cys Cys Cys Thr Gly Ala Ala Cys Cys Thr Gly
            20                  25                  30


<210> SEQ ID NO 30
<211> LENGTH: 32
<212> TYPE: PRT
<213> ORGANISM: Artificial sequence
<220> FEATURE:
<223> OTHER INFORMATION: synthetic

<400> SEQUENCE: 30

Gly Gly Thr Cys Thr Cys Cys Cys Gly Ala Thr Cys Gly Thr Cys Ala
1               5                   10                  15

Ala Ala Gly Gly Thr Thr Thr Gly Gly Gly Gly Thr Cys Cys Gly Cys
            20                  25                  30
```

COMPOSITIONS AND METHODS FOR MODULATING TRP CHANNEL ACTIVITY

CROSS-REFERENCE TO RELATED APPLICATIONS

This application is a Section 371 U.S. national stage entry of International Patent Application No. PCT/US2021/028602, International Filing Date Apr. 22, 2021 which claims priority to U.S. Provisional Patent Application No. 63/014,816, filed Apr. 23, 2020, the entire contents of which are incorporated herein by reference for all purposes.

STATEMENT OF RELATED APPLICATIONS

This application claims priority to U.S. Provisional Patent Application No. 63/014,816, filed Apr. 23, 2020, the entire contents of which are incorporated herein by reference for all purposes.

FIELD

The disclose relates to tryptophan catabolites and methods of use thereof. In particular, the disclosure relates to tryptophan catabolites and uses thereof in methods of treating gastrointestinal disorders, suppressing appetite, and promoting weight loss in a subject.

BACKGROUND

Transient receptor potential (TRP) channels act as molecular sensors of multiple stimuli, including changes in pH, chemicals, temperature, and osmolarity. The TRP family of ion channels is divided into six subfamilies, classified as canonical (TRPC), vanilloid (TRPV), ankyrin (TRPA), melastatin (TRPM), polycystin (TRPP), and mucolipin (TRPML). Transient receptor potential ankyrin 1 (TRPA1) is an excitatory calcium-permeable non-selective cation channel expressed in multiple cell types in the central and peripheral nervous system. This includes a subpopulation of nociceptive primary sensory neurons from dorsal root ganglia and trigeminal ganglia that innervate epidermis as well as visceral organs like the lung, heart, and lower gastrointestinal (GI) tract. In addition to nociceptive sensory neurons, TRPA1 is expressed in a subpopulation of vagal sensory neurons that innervate almost all the visceral organs. In addition to nerve cells, TRPA1 is also expressed in astrocytes, oligodendrocytes and Schwann cells. TRPA1 is a common target for chemically-diverse pronociceptive agonists generated in multiple pathophysiological pain conditions. Thereby, pain therapy that reduces TRPA1 agonism can be expected to be superior compared to many other drugs targeting single nociceptive signaling pathways.

In addition to pain, TRPA1 is also known as a gate keeper for inflammation. Primary afferent sensory neurons that innervate target organs release inflammatory neuropeptides in the local area of tissue damage. TRPA1 channels are required for neuronal excitation, the release of inflammatory neuropeptides, and subsequent pain hypersensitivity. TRPA1 is also activated by the release of inflammatory agents from non-neuronal cells in the area of tissue injury or disease.

TRPA1 is also widely expressed outside the nervous system where its function is less understood. In humans, TRPA1 is expressed in high levels in the gastrointestinal tract, urinary bladder and lymphoid tissues including epithelial cells (such as enteroendocrine cells in the intestinal epithelium, urothelium lining the lower urinary tract, endothelium (such as endothelium of rat cerebral and cerebellar arteries) as well as immune cells (such as macrophages and CD4+ T-cells).

Tryptophan is an essential amino acid in humans and other animals, and is also catabolized by bacteria and animals into diverse derivatives. Bacterial products of tryptophan catabolism are diverse with distinct properties, but many are still undefined. Humans and other animals can also metabolize tryptophan into diverse bioactive products including the neurotransmitter serotonin (5-HT). Although high levels of tryptophan are found in the gut, it as well as its microbial and host catabolites can be found throughout the body. Some microbial tryptophan derivatives are better understood than others. For some tryptophan catabolites there are known effects on host biology without known mechanisms of action. Moreover, new microbial tryptophan catabolites continue to be discovered, and many have no defined function. Importantly, there is no existing information linking bacterial tryptophan catabolites and TRP channels in any cell type in humans or any other animals.

SUMMARY

In some aspects, provided herein are methods of treating or preventing a gastrointestinal disorder in a subject. In some embodiments, provided herein is a method of treating or preventing a gastrointestinal disorder in a subject, comprising providing to the subject a composition comprising a tryptophan catabolite. Any suitable tryptophan catabolite may be used. In some embodiments, the tryptophan catabolite is indole, 3-methylindole (Skatole), indole-3-carboxaldehdye (IAld), Indoleacetic acid (IAA), Indoleacrylic acid (IA), indole-3-ethanol (IE), Indole-3-lactic acid (ILA), 3-indolepropionic acid (IPA), or tryptamine.

The methods described herein may be used for treatment of any suitable gastrointestinal disorder. In some embodiments, the gastrointestinal disorder is a gastrointestinal motility disorder. In some embodiments, the gastrointestinal disorder is intestinal pseudo-obstruction, small bowel bacterial overgrowth, small intestinal bacterial overgrowth, constipation, outlet obstruction type constipation, diarrhea, or tropical sprue. In some embodiments, the gastrointestinal disorder is diarrhea associated with diarrhea-predominant irritable bowel syndrome (IBS-D) or constipation associated with constipation-predominant irritable bowel syndrome (IBS-C). In some embodiments, the gastrointestinal disorder is irritable bowel syndrome (IBS). In some embodiments, the IBS is constipation predominant IBS (IBS-C), diarrhea predominant IBS (IBS-D), or post-infections IBS (PI-IBS). In some embodiments, the gastrointestinal disorder is colitis. In some embodiments, the gastrointestinal disorder is Crohn's disease. In some embodiments, the composition comprises indole or indole-3-carboxaldehdye.

In some aspects, provided herein are methods of inducing weight loss and/or suppressing appetite in a subject. In some embodiments, provided herein is a method of inducing weight loss in a subject, comprising administering to the subject a composition comprising a tryptophan catabolite. In some embodiments, provided herein is a method of suppressing appetite in a subject, comprising administering to the subject a composition comprising a tryptophan catabolite. Any suitable tryptophan catabolite may be used. In some embodiments, the tryptophan catabolite is indole, 3-methylindole (Skatole), indole-3-carboxaldehdye (IAld), Indoleacetic acid (IAA), Indoleacrylic acid (IA), indole-3-ethanol (IE), Indole-3-lactic acid (ILA), 3-indolepropionic acid (IPA), or tryptamine.

In some aspects, provided herein are methods of cleansing the colon of a subject. In some embodiments, provided herein is a method of cleansing the colon of a subject, comprising administering to the subject a composition comprising a tryptophan catabolite. Any suitable tryptophan catabolite may be used. In some embodiments, the tryptophan catabolite is indole, 3-methylindole (Skatole), indole-3-carboxaldehdye (IAld), Indoleacetic acid (IAA), Indoleacrylic acid (IA), indole-3-ethanol (IE), Indole-3-lactic acid (ILA), 3-indolepropionic acid (IPA), or tryptamine.

For any of the methods described herein, the subject may be human.

In some aspects, provided herein are compositions comprising a tryptophan catabolite. The tryptophan catabolite may be indole, 3-methylindole (Skatole), indole-3-carboxaldehdye (IAld), Indoleacetic acid (IAA), Indoleacrylic acid (IA), indole-3-ethanol (IE), Indole-3-lactic acid (ILA), 3-indolepropionic acid (IPA), or tryptamine. The compositions find use in a variety of methods, including treating or preventing a gastrointestinal disorder, inducing weight loss, suppressing appetite, and/or cleansing the colon of a subject. The subject may be human. The gastrointestinal disorder may be a gastrointestinal motility disorder. For example, provided herein are compositions for use in a method of treating or preventing a gastrointestinal motility disorder such as intestinal pseudo-obstruction, small bowel bacterial overgrowth, small intestinal bacterial overgrowth, constipation, outlet obstruction type constipation, diarrhea, or tropical sprue. As another example, provided herein are compositions for use in a method of treating or preventing a gastrointestinal disorder such as diarrhea associated with diarrhea-predominant irritable bowel syndrome (IBS-D) or constipation associated with constipation-predominant irritable bowel syndrome (IBS-C). Other suitable gastrointestinal disorders include, for example, is irritable bowel syndrome (IBS). For example, the IBS may be constipation-predominant IBS (IBS-C), diarrhea predominant IBS (IBS-D), or post-infections IBS (PI-IBS). In some embodiments, the gastrointestinal disorder is colitis. In some embodiments, the gastrointestinal disorder is Crohn's disease.

BRIEF DESCRIPTION OF THE DRAWINGS

FIG. 4. EECs express trpa1b and respond to Trpa1 agonist, related to FIG. 3 and FIG. 5. (A) Normalized counts of trpa1a and trpa1b gene expression in zebrafish EECs and other IECs from zebrafish EEC RNA-seq data. (B) Gel image of PCR product from FACS sorted EECs and other IECs cell population using primers from trpa1a, trpa1b and 18S. (C) Epifluorescence image of trpa1b+/+ (left) and trpa1b−/− (right) Tg(neurod1:Gcamp6f) zebrafish before or 2 mins post Trpa1 agonist AITC stimulation. (D) Epifluorescence image of Tg(neurod1:Gcamp6f) zebrafish following AITC stimulation with or without Trpa1 antagonist HC030031 treatment. (E) Epifluorescence image of trpa1a+/+ and trpa1a−/− Tg(neurod1:Gcamp6f) zebrafish 2 mins after AITC stimulation. (F) Quantification of EEC Gcamp fluorescence signal in trpa1a+/+, trpa1a+/− and trpa1a−/− zebrafish. (G) Confocal projection of trpa1b+/+ and trpa1b−/− Tg(neurod1:CaMPARI) zebrafish after AITC stimulation and UV light photoconversion. (H) Model of gut bacterial CFU quantification. (I) Quantification of gut bacterial CFU in trpa1b+/+, trpa1b+/− and trpa1b−/− conventionalized zebrafish. (J) Epifluorescence image of WT, Tg(neurod1:cre), Tg(gata5:RSD) and Tg(neurod1:cre); Tg(gata5:RSD) zebrafish. The EECs in all the groups are labelled by Tg(neurod1:EGFP). Note that neurod1:EGFP labelling is largely absent in Tg(neurod1:cre); Tg(gata5:RSD) zebrafish indicating EEC ablation. (K) Confocal images of Tg(neurod1:cre) (left) and Tg(neurod1:cre); Tg(gata5:RSD) (right) zebrafish intestine stained with PYY antibody. Yellow arrows in D indicate PYY+ EECs. (L) qPCR analysis of EEC marker genes, other IEC marker genes and neuronal genes in WT and EEC-ablated zebrafish. (M) Quantification of zebrafish survival rate when treated with different doses of *E. tarda* FL6-60. (N) Representative image of zebrafish treated with $10^6$ CFU/ml or $10^7$ CFU/ml *E. tarda*. Note that in the $10^6$ CFU/ml treated zebrafish, the majority of the surviving zebrafish do not exhibit gross pathology (top image). While many of the surviving zebrafish treated with $10^7$ CFU/ml *E. tarda* displayed deflated swim bladder, altered intestinal morphology and ruptured skin (bottom image). (O) Quantification of gut bacterial CFU in WT, Tg(neurod1:cre), Tg(gata5:RSD) and Tg(neurod1:cre); Tg(gata5:RSD) conventionalized zebrafish. (P) Epifluorescence image of Tg(gata5:RSD) and EEC-ablated zebrafish treated with *E. tarda* mCherry for 3 days. (Q) Quantification of *E. tarda* mCherry fluorescence intensity in the intestinal lumen of Tg(gata5:RSD) or EEC-ablated zebrafish. One-way ANOVA with Tukey's post test was used in F, I, L, O and student t-test was used in Q for statistical analysis. n.s. (not significant), $*p<0.05$, $p<0.01$, $*p<0.001$.

FIG. 5. Activation of EEC Trpa1 signaling facilitates enteric *E. tarda* clearance. (A) Schematic of zebrafish *E. tarda* treatment. (B-C) Representative image of trpa1b+/+ or trpa1b−/− zebrafish treated with *E. tarda* expressing mCherry (*E. tarda* mCherry). (D) Quantification of *E. tarda* mCherry fluorescence in trpa1b+/+ or trpa1b−/− zebrafish intestine. (E) Quantification of intestinal *E. tarda* CFU in trpa1b+/+ or trpa1b−/− zebrafish. (F) Schematic of genetic model in which EECs are ablated via Cre-induced Diptheria Toxin (DTA) expression. (G) Representative image of Tg(neurod1:cre; cmlc2:EGFP) and Tg(neurod1:cre; cmlc2:EGFP); TgBAC(gata5:RSD) with EECs that are labelled by Tg(neurod1:EGFP). (H) Quantification of intestinal *E. tarda* CFU in WT or EEC ablated zebrafish. Student's t-test was used in D, E, H. $*p<0.05$; $****p<0.0001$.

FIG. 7. Activation of EEC Trpa1 signaling promotes intestinal motility. (A) Illustration of EEC Trpa1 activation using an Optovin-UV platform. (B) Confocal image of trpa1b+/+ and trpa1b−/− Tg(neurod1:Gcamp6f) zebrafish EECs before and after UV activation. (C) Quantification of EEC Gcamp6f fluorescence changes in trpa1b+/+ and trpa1b−/− zebrafish before and after UV induction. (D) Representative images of Tg(neurod1:Gcamp6f) zebrafish intestine before and after UV-induced Trpa1 activation. Yellow arrowheads indicate the movement of intestinal luminal contents from anterior to posterior following EEC activation. (E) PIV-Lab velocity analysis to quantify intestinal motility in WT and EEC ablated zebrafish. Spatiotemporal heatmap series representing the μ velocity of the imaged intestinal segment at the indicated timepoint post Trpa1 activation. (F) Quantification of the mean intestinal velocity magnitude before and after UV activation in WT and EEC ablated zebrafish. (G) Model of light activation of ChR2 in EECs. (H) Fluorescence image of Tg(neurod1:Gal4); Tg(UAS:ChR2-mCherry) zebrafish that express ChR2 in EECs. (I) Confocal image of ChR2 expressing EECs in Tg(neurod1:Gcamp6f) intestine before and after blue light-induced ChR2 activation. (J) Quantification of EEC Gcamp fluorescence intensity before and after blue light-induced ChR2 activation. (K) Intestinal velocity magnitude before and after blue-light induced activation in ChR2+Trpa1+ EECs. (L) Mean velocity magnitude before and after blue light-induced activation in ChR2+Trpa1+ EECs. (M) Experimental design schematic for panels N and O. (N) Heatmap representing the μ velocity of the imaged intestinal segment at indicated timepoints following *Aeromonas* sp. or *E. tarda* gavage. (O) Mean intestinal velocity magnitude in zebrafish without gavage or gavaged with PBS or different bacterial strains. Student's t-test was used in O. $****p<0.0001$.

Figures 1A, 1B, 1C, 1D, 1E, 1F:
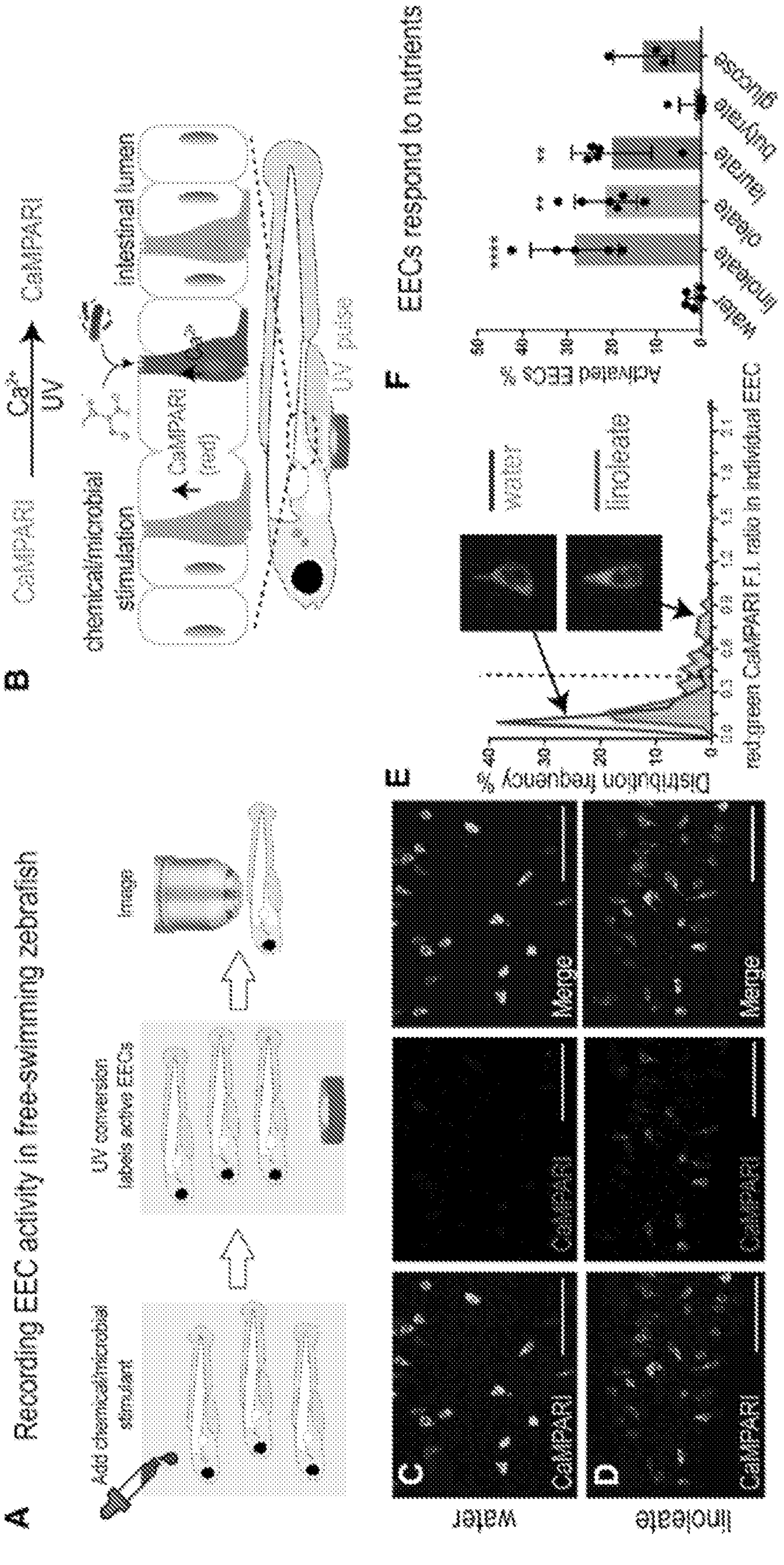
FIG. 1. *E. tarda* activates zebrafish EECs in vivo. (A) Experimental approach for measuring EEC activity in free-swimming zebrafish. (B) Method for recording EEC responses to chemical and microbial stimulants in the EEC-CAMPARI model. (C-D) Confocal projection of mid-intestinal EECs upon water (C, negative control) or linoleate (D) stimulation in Tg(neurod1:CaMPARI) following UV-photoconversion. (E) Frequency distribution of EECs' red:green CAMPARI fluorescence intensity ratio in water or linoleate-stimulated zebrafish. n=177 for water group and n=213 for linoleate group. (F) Percent EEC response in Tg(neurod1:CaMPARI) zebrafish. (G-H) Confocal projection of mid-intestinal EECs upon *Aeromonas* sp. (G) or *E. tarda* (H) stimulation in Tg(neurod1:CaMPARI) following UV-photoconversion. (I) Frequency distribution of EECs' red:green CAMPARI fluorescence intensity ratio in zebrafish treated with water or *E. tarda*. n=117 for water group and n=156 for *E. tarda* group. (J) Representative heatmap image showing *Aeromonas* sp., *B. subtilis* and *E. tarda* stimulated EEC red:green CAMPARI fluorescence ratio. (K) EEC activation in Tg(neurod1:CaMPARI) zebrafish stimulated with different bacterial strains. (L) Representative Tg(neurod1:Gcamp6f) zebrafish intestine stimulated with *E. tarda*. One-way ANOVA with Tukey's post-test was used in F and K. *p<0.05; p<0.01; *p<0.001; ****p<0.0001.

FIG. 9. Activation of EEC Trpa1 signaling activates enteric cholinergic neurons and promotes intestinal motility through 5-HT. (A) Working model showing Trpa1 stimulation in EECs activates enteric neurons. (B) Confocal image of ret+/? (ret+/+ or ret+/−) and ret−/− zebrafish intestine. neurod1 labelled EECs shown in green and NBT labelled ENS shown in magenta. (C) Quantification of mean intestinal velocity magnitude before and after EEC Trpa1 activation in ret+/? zebrafish. (D) Quantification of mean intestinal velocity magnitude before and after UV activation in ret−/− zebrafish. (E) Confocal image showing EECs (neurod1+; green) and cholinergic enteric neurons (chata+; magenta) in zebrafish intestine. The asterisks indicate Cholinergic enteric neuron cell bodies which reside on the intestinal wall. (F) Higher magnification view indicates the EECs (green) directly contact nerve fibers that are extended from the chata+ enteric neuron cell body (magenta) as indicated by yellow arrows. (G-H) Confocal image showing Trpa1+ EECs (green) form direct contact with chata+ enteric neurons (magenta). (I-J) In vivo calcium imaging of cholinergic enteric neurons. All the enteric neurons are labelled as magenta by NBT:DsRed. Yellow arrow indicates a chata+ enteric neuron that express Gcamp6s. (K) In vivo calcium imaging of chata+ enteric neuron before and after EEC Trpa1 activation. (L) Quantification of chata+ enteric neuron Gcamp6s fluorescence intensity before and after EEC Trpa1 activation. (M) Confocal image of TgBAC(trpa1b:EGFP) zebrafish intestine stained for 5-HT. Yellow arrows indicate the presence of 5-HT in the basal area of trpa1b+ EECs. (N) Confocal image showing zebrafish Trpa1b+ EECs (green) express Tph1b (magenta). (O) Quantification of intestinal motility changes in response to EEC Trpa1 activation in tph1b+/− and tph1b−/− zebrafish. Student's t test was used in O. **p<0.01

FIG. 10. Zebrafish EECs directly communicate with chata+ ENS, related to FIG. 9. (A-B) Confocal projection of 6 dpf (A) and adult (B) Tg(neurod1:EGFP) zebrafish intestine stained with the neuronal marker synaptic vesical protein 2 (SV2, magenta) antibody. (C) Higher magnification view of an EEC that exhibiting a neuropod contacting SV2 labelled neurons in the intestine. Yellow arrow indicates the EEC neuropod is enriched in SV2. (D) Higher magnification view of an EEC and neuropod in Tg(neurod1:TagRFP); Tg(neurod1:mitoEOS) zebrafish. The yellow arrow indicates the EEC neuropod is enriched in mitochondria (green, labelled by neurod1:mitoEOS). (E) Confocal projection of chata+ ENS in TgBAC(chata:Gal4); Tg(UAS:mCherry-NTR) zebrafish intestine. Asterisks indicate the chata+ enteric neuron cell bodies. (F) Higher magnification view of a chata+ ENS (white arrow in E). The nuclei of this chata+ enteric neuron is shown on the right. (F') The axon processes of the chata+ enteric neuron. Note this neuron displays a typical Dogiel type II morphology in which multiple axons project from the cell body. (G) Confocal projection of chata+ ENS and EECs in TgBAC(chata:Gal4); Tg(UAS:mCherry-NTR); Tg(neurod1:EGFP) zebrafish intestine. EECs are labeled as green and chata+ ENS are labeled as magenta. Asterisks indicate the chata+ enteric neuron cell bodies. (H) Higher magnification view of the physical connection between EECs and the chata+ enteric neuron. Yellow arrow indicates an EEC forming a neuropod to contact a chata+ enteric neuron. (I) Confocal projection of EECs (2F11+, green) and chata+ ENS (magenta) in TgBAC(chata:Gal4); Tg(UAS:NTR-mCherry) zebrafish. An asterisk indicates the chata+ ENS cell body. (J) Higher magnification view of the connection between EECs and chata+ ENS fibers. The point where EECs connected with chata+ nerve fibers are indicated by yellow arrows. (K) Schematic of Optovin-UV experiment in zebrafish that are anatomically disconnected from their CNS. The Optovin-treated zebrafish were mounted and placed on a confocal objective station. Immediately prior to imaging, the head of the mounted zebrafish was quickly removed with a sharp razor blade and imaging was then performed. (L) Quantification of the mean intestinal velocity before and post UV treatment in decapitated zebrafish. (M) Schematic and confocal image shows the chata+ ENS which is labelled by both Gcamp6s and mCherry in decapitated TgBAC(chata:Gcamp6s); Tg(UAS:Gcamp6s); Tg(UAS:NTR-mCherry) zebrafish. (N) Confocal image shows the chata+ ENS Gcamp fluorescence intensity before and post Trpa1$^{+}$ EEC activation by UV light. (O) Quantification of relative chata+ ENS Gcamp fluorescence intensity before and post Trpa1+ EEC activation. The Gcamp fluorescence intensity was normalized to mCherry fluorescence. n=12 from 7 zebrafish. (P) $Log_2$ fold change of presynaptic genes in zebrafish, mouse and human EECs. (Q-R) Confocal image and higher magnification view of TgBAC(trpa1b:EGFP); Tg(tph1b:mCherry-NTR) zebrafish intestine showing the tph1b+ (magenta) trpa1b+ (green). (S) Quantification of tph1a and tph1b in zebrafish EECs. (T) Quantification of 5-HT+ or tph1b+ EECs. (U) Quantification of tph1b+ and trpa1b+ EECs. Note the majority of tph1b+ EECs are trpa1b+. (V) Quantification of mean intestinal u velocity in unstimulated tph1b+/− and tph1b−/− zebrafish. Student t-test was used in V.

Figure 6I:
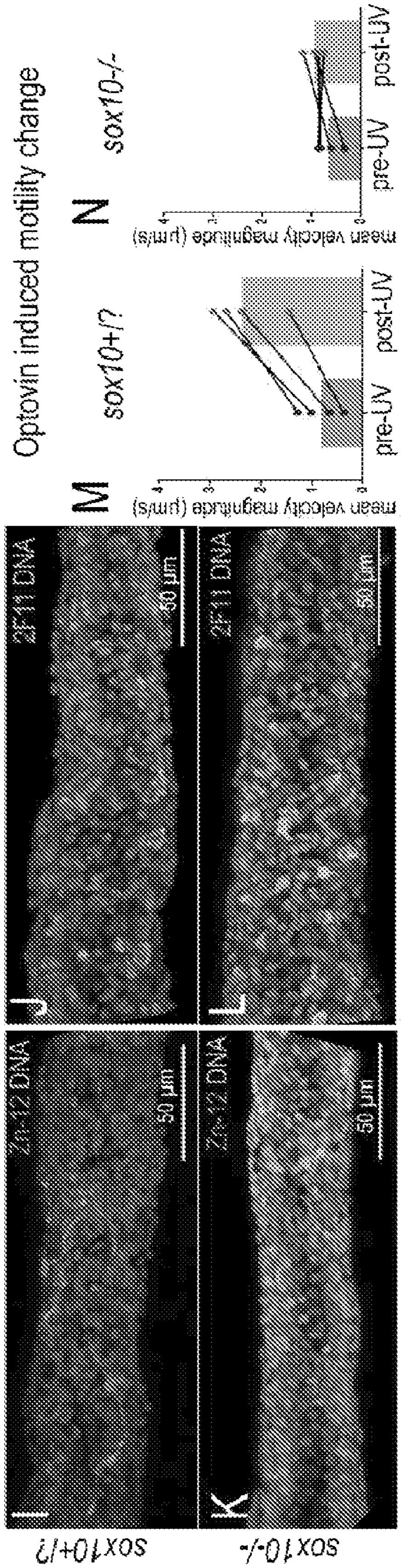
FIG. 6. The role of the enteric nervous system in EEC Trpa1-induced intestinal motility, related to FIG. 9. (A-B) Epifluorescence image of ret+/+ or ret+/−(ret+/?, A) and ret−/− (B) Tg(NBT:DsRed); Tg(neurod1:EGFP) zebrafish. The intestines are denoted by white dash lines. (C-D) Epifluorescence image of ret+/? Tg(neurod1:Gcamp6f) zebrafish before (C) and 2 mins after AITC stimulation (D). (E-F) Epifluorescence image of ret−/− Tg(neurod1:Gcamp6f) zebrafish before (E) and 2 mins after AITC stimulation (F). (G) Quantification of ret+/? and ret−/− intestinal u velocity following Optovin-UV-induced Trpa1 activation. (H) Quantification of velocity before and after Optovin-UV-induced Trpa1 activation in ret+/? and ret−/− zebrafish. (I-J) Confocal projection of sox10+/? zebrafish intestine stained with Zn12 (I, magenta, ENS labeling) or 2F11 (J, green, EEC labeling). (K-L) Confocal projection of sox10−/− zebrafish intestine stained with zn-12 (K) or 2F11 (L). (M-N) Quantification of changes in mean intestinal velocity magnitude before and after Optovin-UV activation in sox10+/? (M) or sox10−/− (N) zebrafish. (O-P) Confocal projection of TgBAC(trpa1b:EGFP) zebrafish intestine stained with Desmin (myoblast or smooth muscle cell marker, O') or Zn12 (ENS marker, P'). (Q) Confocal image of TgBAC(trpa1b:EGFP); Tg(NBT:DsRed) zebrafish intestine. Note in P and Q that both Zn12+ ENS and NBT+ ENS are trpa1b−. (R) Confocal image of TgBAC(chata:Gal4); Tg(UAS:NTR-mCherry); TgBAC(trpa1b:EGFP) zebrafish intestine. Note that the chata+ ENS are trpa1b−.

FIG. 11. Zebrafish vagal sensory nerve innervate the intestine, related to FIG. 12 (A-B) Lightsheet imaging of the right (A) and left (B) side of zebrafish intestine stained with acetylated α-tubulin antibody (white). (C) Schematic diagram of the Vagal-Brainbow model to label vagal sensory cells using Tg(neurod1:cre); Tg(βact2:Brainbow) zebrafish. See Vagal-Brainbow projection in FIG. 6F. (D) Confocal image of vagal ganglia in brainbow zebrafish stained with GFP antibody (green). Note that GFP antibody recognizes both YFP+ and CFP+ vagal sensory neurons. Six branches ($V_{i}$ to $V_{vi}$) extend from the vagal sensory ganglia and branch $V_{vi}$ innervates the intestine. (E-E') Confocal image of vagal sensory ganglia in brainbow zebrafish showing that $V_{vi}$ exits from the ganglia and courses behind the esophagus. (F-G) Confocal image of the proximal (F) and distal (G) intestine in brainbow zebrafish. The vagus nerve (green) innervates both intestinal regions. (H) Confocal image of vagal sensory ganglia in Tg(isl1:EGFP); Tg(neurod1:TagRFP) zebrafish. The vagal sensory ganglia is indicated by a yellow circle. The asterisk indicates the posterior lateral line ganglion. Note that isl1 (green) is expressed in the vagal sensory ganglia and overlaps with neurod1 (magenta). (I) Confocal image of intestine in Tg(isl1:EGFP); Tg(neurod1:TagRFP) zebrafish. The vagus nerve is labelled by isl1 (green) and the intestinal EECs are labelled by neurod1 (magenta). (J) Confocal plane of intestine in Tg(isl1:EGFP); Tg(neurod1:TagRFP) zebrafish. Note that the $V_{vi}$ branch of the vagus nerve is labelled by isl1 and travels behind the esophagus to innervate the intestine. (K) Schematic of in vivo vagal calcium imaging in PBS or AITC gavaged zebrafish. (L) In vivo vagal calcium imaging of Tg(neurod1:TagRFP); Tg(neurod1:Gcamp6f) zebrafish without gavage, gavaged with PBS or gavaged with AITC.

FIG. 12. EEC Trpa1 signaling activates vagal sensory ganglia. (A) Working model. (B) Confocal image of zebrafish vagal sensory ganglia labelled with Tg(neurod1:EGFP) (green) and acetylated αTubulin antibody staining (AC-aTub, magenta). (C) Lightsheet projection of zebrafish stained for AC-aTub. Yellow arrow indicates vagal nerve innervation to the intestine. (D) neurod1:EGFP+ EECs (green) directly contact vagal sensory nerve fibers labelled with αTubulin (white). (E) Confocal image of the vagal sensory nucleus in zebrafish larvae hindbrain where vagal sensory neurons project. Vagal sensory nerve fibers are labeled with different fluorophores through Cre-brainbow recombination in Tg(neurod1:cre); Tg(βact2:Brainbow) zebrafish. The 3D zebrafish brain image is generated using mapzebrain (Kunst et al., 2019). (F) Confocal image of vagal sensory ganglia in Tg(neurod1:cre); Tg(βact2:Brainbow) zebrafish. Asterisk indicates posterior lateral line afferent nerve fibers. Blue arrowheads indicate three branches from vagal sensory ganglia that project to the hindbrain. (G) Confocal image demonstrates the EEC-vagal network in zebrafish intestine. EECs are labeled as magenta by neurod1:TagRFP and the vagal nerve is labeled green by isl1:EGFP. (H) EECs (neurod1+; magenta) directly contact vagal nerve fibers (isl1+; green) as indicated by yellow arrows. (I-J) In vivo calcium imaging of vagal sensory ganglia in zebrafish gavaged with PBS (I) or *E. tarda* (J). (K) Quantification of individual vagal sensory neuron Gcamp6f fluorescence intensity in *E. tarda* or PBS gavaged zebrafish. (L-N) Confocal image of vagal ganglia (neurod1+; green) stained with p-ERK antibody (activated vagal sensory neurons; magenta) in WT or EEC ablated zebrafish gavaged with PBS or Trpa1 agonist AITC. (O-Q) Confocal projection of vagal ganglia stained with p-ERK antibody in WT or EEC ablated zebrafish gavaged with PBS or *E. tarda*. (R) Quantification of p-ERK+ vagal sensory neurons in WT or EEC ablated zebrafish following PBS or AITC gavage. (S) Quantification of p-ERK+ vagal sensory neurons in WT or EEC ablated zebrafish following PBS or *E. tarda* gavage. (T) Quantification of p-ERK+ vagal sensory neurons in WT or trpa1b−/− zebrafish following *E. tarda* gavage. One-way ANOVA with Tukey's post test was used in R and S and Student's t-test was used in T. *p<0.05; p<0.01; *p<0.001; ****p<0.0001.

FIG. 13. *E. tarda* derived Tryptophan catabolites activate Trpa1 and the EEC-vagal pathway. (A) Method for preparing different fractions from *E. tarda* GZM (zebrafish water) culture. (B) Activated EECs in Tg(neurod1:CaMPARI) zebrafish stimulated by different *E. tarda* fractions. (C) Activated EECs in trpa1b+/+ and trpa1b−/− Tg(neurod1:CaMPARI) zebrafish stimulated with *E. tarda* CFS. (D) Screening of supernatants of *E. tarda* in GZM culture medium by HPLC-MS. Samples were collected at 0, 1, 6, 24 h. Abbreviations are as follows: IAld, indole-3-carboxaldehyde; and IEt, tryptophol. Extracted ions were selected for IAld (m/z 145), IEt, (m/z 161), and Indole (m/z 117). (E) Chemical profiles of Trp-Indole derivatives from supernatants of various commensal bacteria in GZM medium for 1 day of cultivation. Values present normalized production of Trp-Indole derivatives based on CFU. (F) Tg(neurod1:Gcamp6f) zebrafish stimulated by Indole or IAld. Activated EECs in the intestine are labelled with white arrows. (G) Quantification of EEC Gcamp activity in trpa1b+/+ and trpa1b−/− zebrafish stimulated with Indole or IAld. (H) Schematic of experimental design to test effects of indole and IAld on human or mouse Trpa1. (I) Dose-response analysis of the integrated Calcium 6 fluorescence response above baseline (Fmax-F0; maximal change in $Ca^{2+}$ influx) as a function of indole and IAld concentration in human TRPA1 expressing HEK-293T cells. ($EC_{50}$=88.7 μM, 68.2-114.7 μM 95% CI for indole; and, $EC_{50}$=77.7 μM, 66.8-91.8 μM 95% CI for IAld). Concentration-response data were normalized to 1 mM cinnamaldehyde (CAD), a known TRPA1 agonist. Data represent the mean of 3-4 experiments, each performed with 3-4 replicates. (J) Dose-response analysis of A967079 inhibition of Indole and IAld induced $Ca^{2+}$ influx. ($IC_{50}$=149.6 nM, 131.3-170.8 nM 95% CI for Indole; and, $IC_{50}$=158.1 nM, 135.4-185.6 μM 95% CI for IAld). Concentration-response data of A967079 inhibition was normalized to response elicited by 100 μM agonist (Indole or IAld). (K-N) In vivo calcium imaging of vagal sensory ganglia in WT or EEC ablated Tg(neurod1:Gcamp6f); Tg(neurod1:TagRFP) zebrafish gavaged with PBS, Indole or IAld. (O) Quantification of individual vagal sensory ganglia cell Gcamp6f fluorescence intensities in WT or EEC ablated zebrafish gavaged with PBS or 1 mM Indole. (P) Schematic of amperometric measurements to examine the effects of indole on 5-HT secretion in mouse and human small intestinal tissue. (Q) Indole caused a significant increase in 5-HT secretion in mouse duodenum; however, no such effects were observed in the presence of Trpa1 antagonist HC030031. (R) Indole caused a significant increase in 5-HT secretion in human ileum; however, no such effects were observed in the presence of Trpa1 antagonist HC030031. Data in B, C, G, Q, R are presented as mean±/−SD. One-way ANOVA with Tukey's post test was used in B and Q, Student's t-test was used in C, H and paired one-way ANOVA with Tukey's post test was used in P-R. *p<0.05; p<0.01; *p<0.001; ****p<0.0001.

FIG. 14. *E. tarda* secretes tryptophan catabolites indole and IAld that activate Trpa1, related to FIG. 13. (A) Chemical profiles of Trp-Indole derivatives from supernatants of *E. tarda* in nutrient-rich TSB media. (B) Screening of supernatants of *E. tarda* in TSB media. Samples for *E. tarda* in TSB culture were collected at 0, 6, 18, and 24 h. (C) Screening of supernatants of *E. tarda* in TSB media. Abbreviations are as follows: IAld, indole-3-carboxaldehyde; IEt, tryptophol; IAM, indole-3-acetamide; IAA, indole-3-acetic acid; IAAld, indole-3-acetaldehyde; and IpyA, indole-3-pyruvate. Extracted ions were selected for IAld (m/z 145), IEt, (m/z 161), Indole (m/z 117), IAAld (m/z 159), IAM (m/z 174), IAA (m/z 175), and IpyA (m/z 203). (D) Chemical profiles of Trp-Indole derivatives from supernatants of various commensal bacteria in TSB medium for 1 day of cultivation. Y-axis values represent production of Trp-Indole derivatives normalized to CFU, with each strain beginning at zero. (E) Proposed model of *E. tarda* tryptophan catabolism. (F) EEC Gcamp fluorescence intensity in Tg(neurod1:Gcamp6f) zebrafish stimulated with different tryptophan catabolites. (G-H) Represented images (G) and quantification (H) of activated EECs in Tg(neurod1:CaMPARI) zebrafish that is stimulated with PBS or with CFS from *E. tarda* 23685 and *E. tarda* 15974. (I-J) Indole (I) and IAld (J)

stimulation of $Ca^{2+}$ influx in human TRPA1 expressing HEK-293T cells, measured as fluorescence increase of intracellular Calcium 6 indicator. (K-L) Effects of TRPA1 inhibition using various concentrations of inhibitor A967079, on subsequent $Ca^{2+}$ influx in response to indole (100 μM, G) or, IAld (100 μM, H) in human TRPA1 expressing HEK-293T cells. Data are from a representative experiment performed in triplicate and repeated three times. (M-N) Sensitivity of mouse TRPA1 to indole and IAld. (M) Dose-response effects of indole and IAld ($EC_{50}$=130.7 μM, 107.8-158.4 μM 95% CI for Indole; and, $EC_{50}$=189.0 μM, 132.8-268.8 μM 95% CI for IAld). Concentration-response data were normalized to 1 mM cinnamaldehyde (CAD), a known TRPA1 agonist. (N) Effects of the Trpa1 inhibitor A967079, on $[Ca^{2+}]_i$ in response to 100 μM indole in mouse Trpa1-expressing HEK-293T cells. Cells were treated with A967079 before the addition of indole (100 μM). Changes in Calcium 6 fluorescence above baseline (Fmax-F0; maximal $[Ca^{2+}]_i$) are expressed as a function of Trpa1 inhibitor, A967079, concentration (IC50=315.5 nM, 202.3-702.3 nM 95% CI for indole). Concentration-response data were normalized to the response elicited by 100 μM Indole. Data represent mean±s.e.m. of normalized measures pooled from two experiments, each performed in triplicate.

FIG. 15. Effects of tryptophan catabolites and AhR inhibitor on intestinal motility, related to FIG. 13. (A) Experimental model for measuring intestinal motility in response to indole stimulation. (B) EEC Gcamp6f fluorescence (blue line) and changes in intestinal motility (heat map) following indole stimulation. (C) Intestinal u velocity in response to PBS or indole stimulation. (D) Mean intestinal velocity magnitude 0-50s and 200-250s following indole stimulation. (E) Schematic of experiment design in measuring the effects of indole or IAld in vagal ganglia calcium. WT or EEC ablated Tg(neurod1:Gcamp6f); Tg(neurod1:TagRFP) zebrafish that were gavaged with indole or IAld. (F) Quantification of the Gcamp6f to TagRFP fluorescence ratio in the whole vagal sensory ganglia in WT or EEC ablated zebrafish 30 minds following indole gavage. (G) Schematic of experiment design in testing the effects of AhR inhibitors on intestinal *E. tarda* accumulation. To test whether AhR is involved in Trpa1+EEC induced intestinal motility, two AhR inhibitors, CH223191 and folic acid, were applied. (H) Representative image of DMSO or AhR inhibitor CH223191 treated zebrafish that were infected with *E. tarda* expressing mCherry (*E. tarda* mCherry). (I) Quantification of *E. tarda* mCherry fluorescence in DMSO, AhR inhibitor CH223191 or Folic acid treated zebrafish intestine. (J) Schematic of experimental design to examine effects of AhR inhibitors on $Trpa1^+$ EEC induced intestinal motility. (K) Quantification of mean intestinal velocity magnitude in DMSO, CH223191 or Folic acid treated zebrafish before and post UV activation. Treatment of zebrafish with these AhR inhibitors was insufficient to block *E. tarda* intestinal accumulation. (L) Quantification of mean intestinal velocity magnitude change in DMSO, CH223191 or Folic acid treated zebrafish upon UV-induced $Trpa1^+$EEC activation. Treatment of zebrafish with these AhR inhibitors was insufficient to block Optovin-UV induced intestinal motility change. (M) Schematic of small intestine and colonic regions in 10-week old SPF C57Bl/6 mice that were collected for HPLC-MS analysis. (N) Chemical profiles of Trp-Indole derivatives from colon and small intestine of conventionally-reared mice. Relative amounts of the Trp-metabolites from each mouse was normalized by tissue weight. M1-M3: males. M4-M5: females. Extracted ions were selected for Indole (m/z 117), IAld (m/z 145), and IEt, (m/z 161). One-way ANOVA with Tukey's post test was used in F, I, L. P<0.01, **P<0.0001, n.s. not significant.

DETAILED DESCRIPTION

1. Definitions

Unless otherwise defined, all technical terms used herein have the same meaning as commonly understood by one of ordinary skill in the art to which this disclosure belongs. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The use of the terms "a" and "an" and "the" and "at least one" and similar referents in the context of describing the invention (especially in the context of the following claims) are to be construed to cover both the singular and the plural, unless otherwise indicated herein or clearly contradicted by context.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

As used herein, the term "about" is used to provide flexibility to a numerical range endpoint by providing that a given value may be "slightly above" or "slightly below" the endpoint without affecting the desired result. In some embodiments, "about" may refer to variations of in some embodiments ±20%, in some embodiments ±10%, in some embodiments ±5%, in some embodiments ±1%, in some embodiments ±0.5%, and in some embodiments ±0.1% from the specified amount.

As used herein, the terms "comprise", "include", and linguistic variations thereof denote the presence of recited feature(s), element(s), method step(s), etc. without the exclusion of the presence of additional feature(s), element(s), method step(s), etc.

Recitation of ranges of values herein are merely intended to serve as a shorthand method of referring individually to each separate value falling within the range, unless otherwise-indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

As used herein, the terms "co-administration" and variations thereof refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Accordingly, co-administration may be especially desirable in embodiments where the co-administration of two or more agents results in sensitization of a subject to beneficial effects of one of the agents via co-administration of the other agent.

The term "carrier" as used herein refers to any pharmaceutically acceptable solvent of agents that will allow a therapeutic composition to be administered to the subject. A "carrier" as used herein, therefore, refers to such solvent as, but not limited to, water, saline, physiological saline, oil-water emulsions, gels, or any other solvent or combination of solvents and compounds known to one of skill in the art that is pharmaceutically and physiologically acceptable to the recipient human or animal. The term "pharmaceutically acceptable" as used herein refers to a compound or composition that will not impair the physiology of the recipient human or animal to the extent that the viability of the recipient is compromised. For example, "pharmaceutically acceptable" may refer to a compound or composition that does not substantially produce adverse reactions, e.g., toxic, allergic, or immunological reactions, when administered to a subject.

The term "intestine" or "intestines" as used interchangeably herein refer to the long-continuous tube running from the stomach to the anus. The term "intestine" includes the small intestine, the large intestine, and the rectum.

The term "gastrointestinal tract" or "GI tract" as used herein refers to the tract from the mouth to the anus. The gastrointestinal tract includes the mouth, esophagus, stomach, and intestines. The "gastrointestinal tract" may also be referred to herein as the "gut".

The term "motility" when used in reference to the GI tract refers to the contraction of muscles that mix and propel contents in the GI tract. The term "gastrointestinal motility disorder" refers to any number of conditions in which motility in the GI tract is abnormal, which may cause one or more undesirable symptoms in an afflicted subject.

As used herein, the terms "prevent," "prevention," and preventing" may refer to reducing the likelihood of a particular condition or disease state (e.g., a gastrointestinal disorder) from occurring in a subject not presently experiencing or afflicted with the condition or disease state. The terms do not necessarily indicate complete or absolute prevention. For example "preventing a gastrointestinal disorder" refers to reducing the likelihood of the gastrointestinal disorder occurring in a subject not presently experiencing or diagnosed with the disorder. The term may also refer to delaying the onset of a particular condition or disease state (e.g., a gastrointestinal disorder) in a subject not presently experiencing or afflicted with the condition or disease state. In order to "prevent" a condition, a composition or method need only reduce the likelihood and/or delay the onset of the condition, not completely block any possibility thereof. "Prevention," encompasses any administration or application of a therapeutic or technique to reduce the likelihood or delay the onset of a disease developing (e.g., in a mammal, including a human).

As used herein, the terms "subject" and "patient" are used interchangeably herein and refer to both human and nonhuman animals. The term "nonhuman animals" includes all vertebrates, e.g., mammals and non-mammals, such as non-human primates, sheep, dogs, cats, horses, cows, chickens, amphibians, reptiles, and the like. In some embodiments, the subject is a human. In some embodiments, the subject is a human. In particular embodiments, the subject may be male. In other embodiments, the subject may be female. In some embodiments, the subject is suffering from or at risk of developing a gastrointestinal disorder. In some embodiments, the subject is overweight or obese.

As used herein, "treat", "treating", "treatment", and variations thereof refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. In some embodiments, treating a gastrointestinal disorder refers to the management and care of the subject for combating and reducing one or more symptoms of the disorder. Treating a gastrointestinal disorder may reduce, inhibit, ameliorate and/or improve the onset of the symptoms or complications, alleviating the symptoms or complications of the disorder, or eliminating the disorder.

2. Compositions and Methods of Use

In some aspects, provided herein are compositions. In some embodiments, provided herein are compositions comprising a TRPA1 agonist. In some embodiments, the TRPA1 agonist is a tryptophan catabolite. The tryptophan catabolite may be any suitable compound that is generated during the catabolism of tryptophan. In some embodiments, the tryptophan catabolite is indole, 3-methylindole (Skatole), indole-3-carboxaldehdye (IAld), Indoleacetic acid (IAA), Indoleacrylic acid (IA), indole-3-ethanol (IE), Indole-3-lactic acid (ILA), 3-indolepropionic acid (IPA), or tryptamine. In some embodiments, the compositions comprise a plurality of tryptophan derivatives. Any suitable combination of tryptophan derivatives may be used. The formula and structure of common tryptophan catabolites are highlighted in Table 1. In some embodiments, the composition may comprise pharmaceutically acceptable salts, solvates, hydrates, prodrugs, or derivatives of a tryptophan catabolite.

In some embodiments, the tryptophan catabolite is made synthetically. In some embodiments, the tryptophan catabolite is isolated from a naturally occurring source. For example, the tryptophan catabolite may be produced by one or more bacteria, in which case the tryptophan catabolite may be referred to herein as a "bacterial tryptophan catabolite".

TABLE 1

Common Tryptophan Catabolites

| Name | Formula | Structure |
|---|---|---|
| Indole | $C_8H_7N$. | 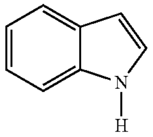 |
| Skatole | $C_9H_9N$. | 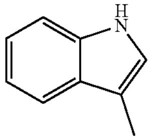 |
| Indole-3-carboxaldehdye | $C_9H_7NO$ | 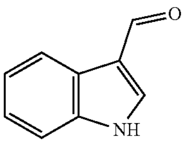 [SMILES: O=Cc1c[nH]c2ccccc12] |
| Indoleacetic acid | $C_{10}H_9NO_2$ | 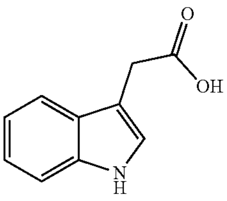 [SMILES: O=C(O)Cc1c[nH]c2ccccc12] |
| Indoleacrylic acid | $C_{11}H_9NO_2$ | 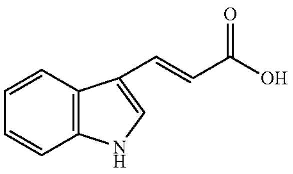 [SMILES: O=C(O)/C=C/c1c[nH]c2ccccc12] |
| Indole-3-ethanol | $C_{10}H_{11}NO$ | 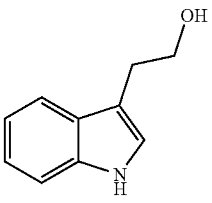 [SMILES: OCCc1c[nH]c2ccccc12] |
| Indole-3-lactic acid | $C_{11}H_{11}NO_3$ | 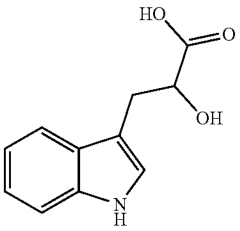 [SMILES: O=C(O)C(O)Cc1c[nH]c2ccccc12] |
| 3-Indolepropionic acid | $C_{11}H_{11}NO_2$ | 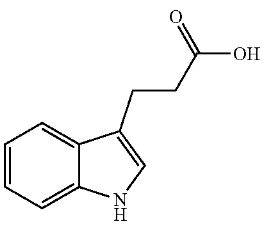 [SMILES: O=C(O)CCc1c[nH]c2ccccc12] |
| Tryptamine | $C_{10}H_{12}N_2$ | 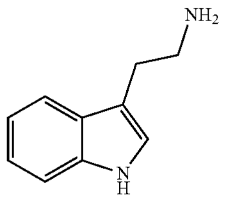 [SMILES: NCCc1c[nH]c2ccccc12] |

In some embodiments, the compositions described herein may be used in methods of modulating GI tract motility. In some embodiments, the compositions described herein may be used in methods of modulating intestinal motility. For example, the compositions may be provided to a subject to modulate motility in any suitable area of the intestine, including the small intestine or the large intestine. Disruption of normal intestinal motility occurs in a variety of GI motility disorders, therefore modulating intestinal motility may be beneficial for treating or preventing a GI motility disorder.

In some embodiments, the compositions described herein may be used in methods of treating or preventing one or more gastrointestinal disorders. The gastrointestinal disorder may be a functional gastrointestinal disorder, wherein the GI tract looks normal when examined by does not move properly. In some embodiments, the gastrointestinal disorder is a structural gastrointestinal disorder, where the GI tract looks abnormal when examined and does not work properly. In some embodiments, the gastrointestinal disorder is a gastrointestinal motility disorder. In some embodiments, the gastrointestinal motility disorder is intestinal pseudo-obstruction, small bowel bacterial overgrowth, small intestinal bacterial overgrowth, constipation, outlet obstruction type constipation (i.e. pelvic floor dyssynergia), or diarrhea. In some embodiments, the gastrointestinal disorder is diarrhea is associated with diarrhea-predominant irritable bowel syndrome (IBS-D). In some embodiments, the gastrointestinal disorder is constipation associated with constipation-predominant irritable bowel syndrome (IBS-C).

In some embodiments, the gastrointestinal disorder is irritable bowel syndrome (IBS). The irritable bowel syndrome may be constipation predominant (IBS-C) or diarrhea predominant (IBS-D). The irritable bowel syndrome may be post-infectious IBS (PI-IBS). In some embodiments, the gastrointestinal disorder is colitis (e.g. infectious colitis, ulcerative colitis). In some embodiments, the gastrointestinal disorder is Crohn's disease. In some embodiments, the gastrointestinal disorder is tropical sprue. Tropical sprue is a malabsorption disease commonly found in tropical regions, marked by abnormal flattening of the villi and inflammation of the lining of the small intestine. Tropical sprue typically starts with an acute attack of diarrhea, fever, and malaise and may ultimately lead to a chronic phase of diarrhea, steatorrhea, weight loss, anorexia, malaise, and nutritional deficiencies. Tropical sprue may be caused by persistent bacterial, viral, or parasitic infections. Tropical sprue may also be caused by folic acid deficiencies, disrupted intestinal motility, and persistent small intestinal bacterial overgrowth, which may be affiliated with small intestinal bacterial overgrowth and/or irritable bowel syndrome.

In some embodiments, compositions comprising a tryptophan catabolite as described herein find use in methods of cleansing the colon. For example, in some aspects the compositions described herein may be provided to the subject for use in a method of cleansing the colon of the subject, such as in preparation for a colonoscopy.

In some embodiments, the compositions herein find use in methods of reducing visceral pain in a subject. For example, the visceral pain may be associated with one or more gastrointestinal disorders, such as constipation. Treating one or more gastrointestinal disorders (e.g. constipation) may result in treatment of the constipation along with associated symptoms, including visceral pain.

In addition to modulating gut motility and treating/preventing gastrointestinal disorders, the compositions described herein find use methods of modulating communication between the gastrointestinal tract and the nervous system in the subject (e.g. modulating gut-brain communication). The vagus nerve is the primary sensory pathway by which visceral information is transmitted to the CNS. The vagus nerve may play a role in communicating gut microbial information to the brain. In particular, the results provided herein demonstrate that, in addition to spinal sensory nerves, EEC-vagal signaling is an important pathway for transmitting specific gut microbial signals to the CNS. The vagal ganglia project directly onto the hindbrain, and that vagal-hindbrain pathway has key roles in appetite and metabolic regulation. Accordingly, compositions comprising a tryptophan catabolite as described herein may be used in methods of regulating appetite in a subject. For example, compositions comprising a tryptophan catabolite may be used in a method of suppressing appetite in a subject. Inhibiting appetite may lead to diminished food intake and/or weight loss in the subject. As another example, compositions comprising a tryptophan catabolite may be used in methods of promoting weight loss in a subject.

The composition may further comprise one or more pharmaceutically acceptable carriers. Suitable carriers depend on the intended route of administration to the subject. Contemplated routes of administration include those oral, rectal, nasal, topical (including transdermal, buccal and sublingual), vaginal, parenteral (including subcutaneous, intramuscular, intravenous and intradermal) and pulmonary administration. In some embodiments, the composition or compositions are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then, if necessary, shaping the product.

Formulations of the present disclosure suitable for oral administration may be presented as discrete units such as capsules, cachets or tablets, wherein each preferably contains a predetermined amount of the one or more therapeutic agents as a powder or granules; as a solution or suspension in an aqueous or non-aqueous liquid; or as an oil-in-water liquid emulsion or a water-in-oil liquid emulsion. In other embodiments, the composition is presented as a bolus, electuary, or paste, etc. In some embodiments, compositions suitable for oral administration may include such further agents as sweeteners, thickeners and flavoring agents. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoleic acid), extenders, preservatives, and stabilizers, etc.

Various delivery systems are known and can be used to administer compositions described herein, e.g., encapsulation in liposomes, microparticles, microcapsules, receptor-mediated endocytosis, and the like. In specific embodiments, it may be desirable to administer the compositions of the disclosure locally to the area in need of treatment (e.g. directly to the intestine); this may be achieved by, for example, and not by way of limitation, local infusion during surgery, injection, or by means of a catheter.

Any suitable amount of the tryptophan catabolite may be provided to the subject. In general, suitable amounts are empirically determined and vary with the pathology being treated, the subject being treated and the efficacy and toxicity of the catabolite. It is understood that therapeutically effective amounts vary based upon factors including the age, gender, and weight of the subject, among others. It also is intended that the compositions and methods of this disclosure may be co-administered with other suitable compositions and therapies.

In general, suitable doses of the tryptophan catabolite may range from about 1 ng catabolite/kg body weight to about 1 g/kg. For example, a suitable dose may be from about 1 ng/kg to about 1 g/kg, about 100 ng/kg to about 900 mg/kg, about 200 ng/kg to about 800 mg/kg, about 300 ng/kg to about 700 mg/kg, about 400 ng/kg to about 600 mg/kg, about 500 ng/kg to about 500 mg/kg, about 600 ng/kg to about 400 mg/kg, about 700 ng/kg to about 300 mg/kg, about 800 ng/kg to about 200 mg/kg, about 900 ng/kg to about 100 mg/kg, about 1 μg/kg to about 50 mg/kg, about 10 μg/kg to about 10 mg/kg, about 100 μg/kg to about 1 mg/kg, about 200 μg/kg to about 900 μg/kg, about 300 μg/kg to about 800 μg/kg, about 400 μg/kg to about 700 μg/kg, or about 500 μg/kg to about 600 μg/kg.

The composition may be provided to the subject at any desired frequency. For example, the composition may be provided to the subject more than once per day (e.g. twice per day, three times per day, four times per day, and the like), once per day, once every other day, once a week, and the like. The one composition may be provided to the subject for any desired duration. For example, the composition may be administered to the subject for at least one week, at least two weeks, at least three weeks, at least one month, at least two months, at least three months, at least six months, at least one year, at least two years, at least three years, at least four years, at least five years, at least ten years, at least twenty years, or for the lifetime of the subject.

The composition may further comprise one or more additional suitable agents, such as a suitable agent for treatment or preventing of a gastrointestinal disorder or a suitable agent for appetite suppression and/or weight loss. Alternatively or in addition, the compositions may be co-administered to the subject along a separate composition comprising the additional agent. Co-administration may be simultaneously or sequentially, in any order.

EXAMPLES

Example 1

Overview

The intestinal epithelium senses nutritional and microbial stimuli using epithelial sensory enteroendocrine cells (EECs). EECs can communicate nutritional information to the nervous system, but similar mechanisms for microbial information are unknown. In vivo real-time measurements of EEC and nervous system activity in zebrafish demonstrate that the bacteria *Edwardsiella tarda* specifically activates EECs through the receptor transient receptor potential ankyrin A1 (Trpa1) and increases intestinal motility in an EEC-dependent manner. Microbial, pharmacological, or optogenetic activation of Trpa1$^+$ EECs directly stimulates vagal sensory ganglia and activates cholinergic enteric neurons through 5-HT. Herein, a subset of indole derivatives of tryptophan catabolism produced by *E. tarda* and other gut microbes were investigated. It was shown that indole derivatives potently activate zebrafish EEC Trpa1 signaling and also directly stimulate human and mouse Trpa1 and intestinal 5-HT secretion. These results establish a molecular pathway by which EECs regulate enteric and vagal neuronal pathways in response to specific microbial signals.

Background

The intestine harbors complex microbial communities that shape intestinal physiology, modulate systemic metabolism, and regulate brain function. These effects on host biology are often evoked by distinct microbial stimuli including microbe-associated molecular patterns (MAMPs) and microbial metabolites derived from digested carbohydrates, proteins, lipids, and bile acid (Brown and Hazen, 2015, Liu et al., 2020, Coleman and Haller, 2017). The intestinal epithelium is the primary interface that mediates this host-microbe communication (Kaiko and Stappenbeck, 2014). The mechanisms by which the intestinal epithelium senses distinct microbial stimuli and transmits that information to the rest of the body remains incompletely understood.

The intestinal epithelium has evolved specialized enteroendocrine cells (EECs) that exhibit conserved sensory functions in insects, fishes, and mammals (Guo et al., 2019, Ye et al., 2019, Furness et al., 2013). Distributed along the entire digestive tract, EECs are activated by diverse luminal stimuli to secrete hormones or neuronal transmitters in a calcium dependent manner (Furness et al., 2013). Recent studies have revealed that EECs form synaptic connections with sensory neurons (Kaelberer et al., 2018, Bellono et al., 2017, Bohorquez et al., 2015). The connection between EECs and neurons forms a direct route for the intestinal epithelium to transmit nutrient sensory information to the brain (Kaelberer et al., 2018). EECs are classically known for their ability to sense nutrients (Symonds et al., 2015) but whether they can be directly stimulated by microbes or microbially derived products is unclear. Short chain fatty acids and branched chain fatty acids from microbial carbohydrate and amino acid catabolism activate EECs via G-protein coupled receptors (Bellono et al., 2017, Lu et al., 2018).

With the growing understanding of gut microbiota and their metabolites, identifying the EEC receptors that recognize distinct microbial stimuli as well as the downstream pathways by which EECs transmit microbial stimuli to regulate local and systemic host physiology, has emerged as an important goal.

The vertebrate intestine is innervated by the intrinsic enteric nervous system (ENS) and extrinsic neurons from autonomic nerves, including sensory nerve fibers from the nodose vagal ganglia and dorsal root ganglia in the spinal cord (Furness et al., 1999). Both vagal and spinal sensory nerve fibers transmit visceral stimuli to the central nervous system and modulate a broad spectrum of brain functions (Brookes et al., 2013). Stimulating EECs with the microbial metabolite isovalerate activates spinal sensory nerves through 5-hydroxytryptamine (5-HT) secretion (Bellono et al., 2017). Whether and how gut microbial stimuli modulate ENS or vagal sensory activity through EECs is still unknown.

Results

*Edwardsiella tarda* Activates EECs Through Trpa1

To identify stimuli that activate EECs in live animals, a new transgenic zebrafish line that permits recording of EEC activity by expressing the calcium modulated photoactivatable ratiometric integrator (CaMPARI) protein in EECs under control of the neurod1 promoter was developed (FIG. 1A, FIGS. 2A-F). When exposed to 405 nm light, CAMPARI protein irreversibly photoconverts from a configuration that emits green light to one that emits red in a manner positively correlated with intracellular calcium levels $[Ca^{2+}]_i$. A high red:green CAMPARI ratio thus reports high intracellular calcium (Fosque et al., 2015). This EEC-CAMPARI system therefore enables imaging of the calcium activity history of intestinal EECs in the intact physiologic context of live free-swimming animals (FIGS. 1A-B, FIGS. 2G-J).

To test the validity of this EEC-CAMPARI system, larvae were stimulated with different nutrients known to activate zebrafish EECs (Ye et al., 2019). Exposure to only water as a vehicle control revealed an expected low basal red:green CAMPARI ratio (FIGS. 1C, E-F). Following long-chain fatty acid stimulation with linoleate, a subpopulation of EECs displayed high red:green CAMPARI ratio (FIGS. 1D, E-F). EECs with a high red:green CAMPARI ratio were classified as "activated EECs". The percentage of activated EECs significantly increased in response to chemical stimuli known to activate EECs, including linoleate, oleate, laurate, and glucose (FIG. 1F), but not in response to the short chain fatty acid butyrate, consistent with previous findings (FIG. 1F) (Ye et al., 2019).

Figures 1G, 1H, 1I, 1J, 1K, 1L:
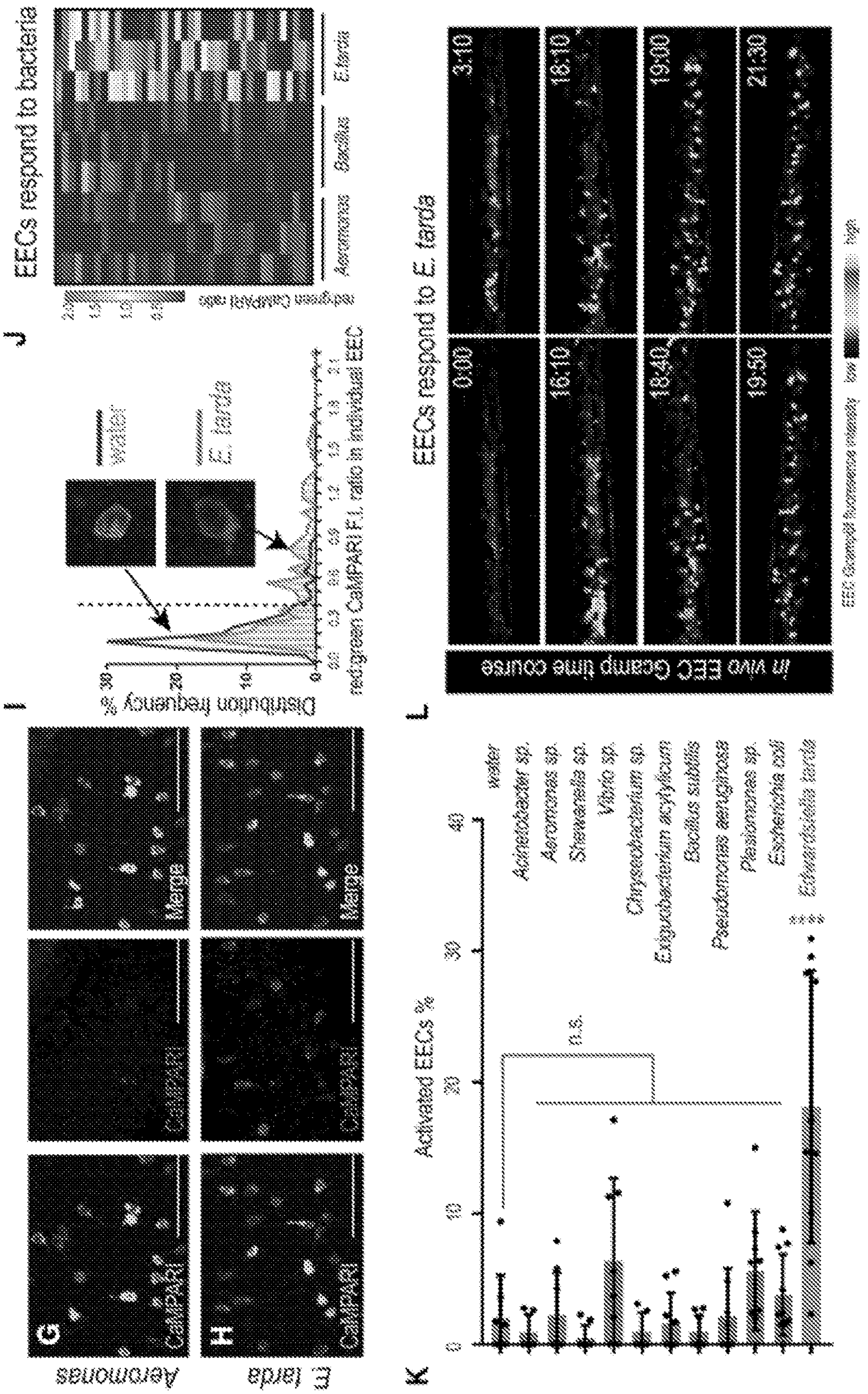
Figures 2A, 2B, 2C, 2D, 2E, 2F:
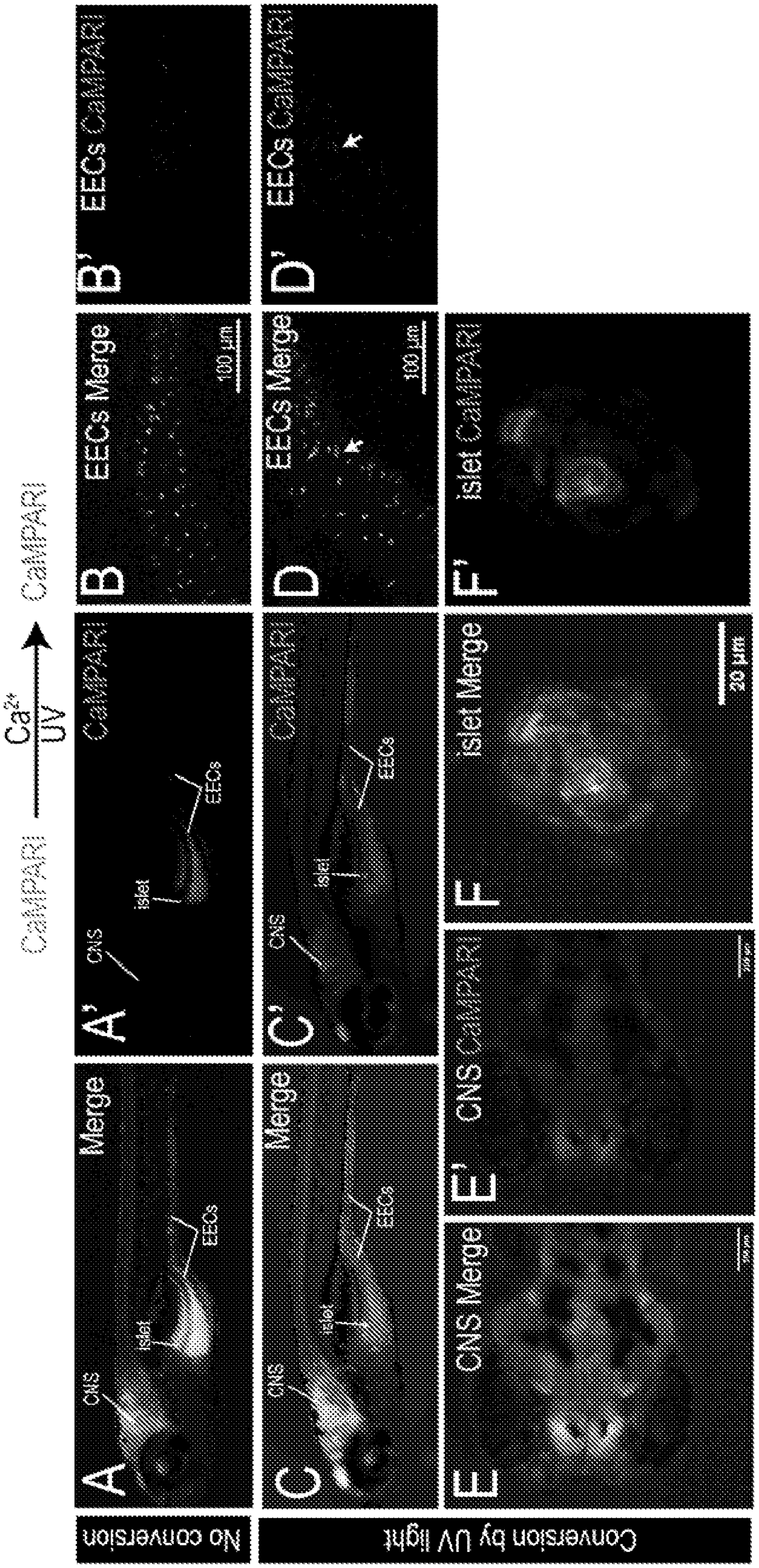
FIG. 2. *E. tarda* activates EECs in vivo, related to FIG. 1. (A) Epifluorescence image of Tg(neurod1:CaMPARI) zebrafish without UV conversion. Note that there is no red CAMPARI signal (magenta) in A'. (B) Confocal image of intestinal EECs in Tg(neurod1:CaMPARI) zebrafish without UV conversion. (C) Epifluorescence image of unstimulated Tg(neurod1:CaMPARI) zebrafish post UV conversion. The red CAMPARI signal is apparent in CNS and islets in C'. (D-F') Confocal image of intestinal EECs (D, D'), CNS (E, E') and islets (F, F') in unstimulated Tg(neurod1:CAMPARI) zebrafish after UV conversion. (G) Schematic of liver, pancreas and intestine in 6 dpf zebrafish larvae. The intestinal region that is imaged to assess the CaMPARI signal is indicated by a red box. (H-J) Quantification of EEC red:green CAMPARI fluorescence ratio in water- and linoleate-stimulated zebrafish. (K) Schematic of in vivo EEC Gcamp recording in response to bacterial stimulation in Tg(neurod1:Gcamp6f) zebrafish. (L) Quantification of EEC Gcamp6f fluorescence in response to stimulation by different bacteria. (M) Quantification of EEC Gcamp6f fluorescence before and 20 mins after *E. tarda* administration. (N-O) Fluorescence image of zebrafish intestine in Tg(neurod1:Gcamp6f) zebrafish without treatment (N) or 5 hours post *E. tarda* treatment (O). (P) Quantification of EEC Gcamp6f fluorescence in zebrafish without or with *E. tarda* treatment. Student's t-test was used in M and P for statistical analysis. *p<0.05.
Figures 2G, 2H:
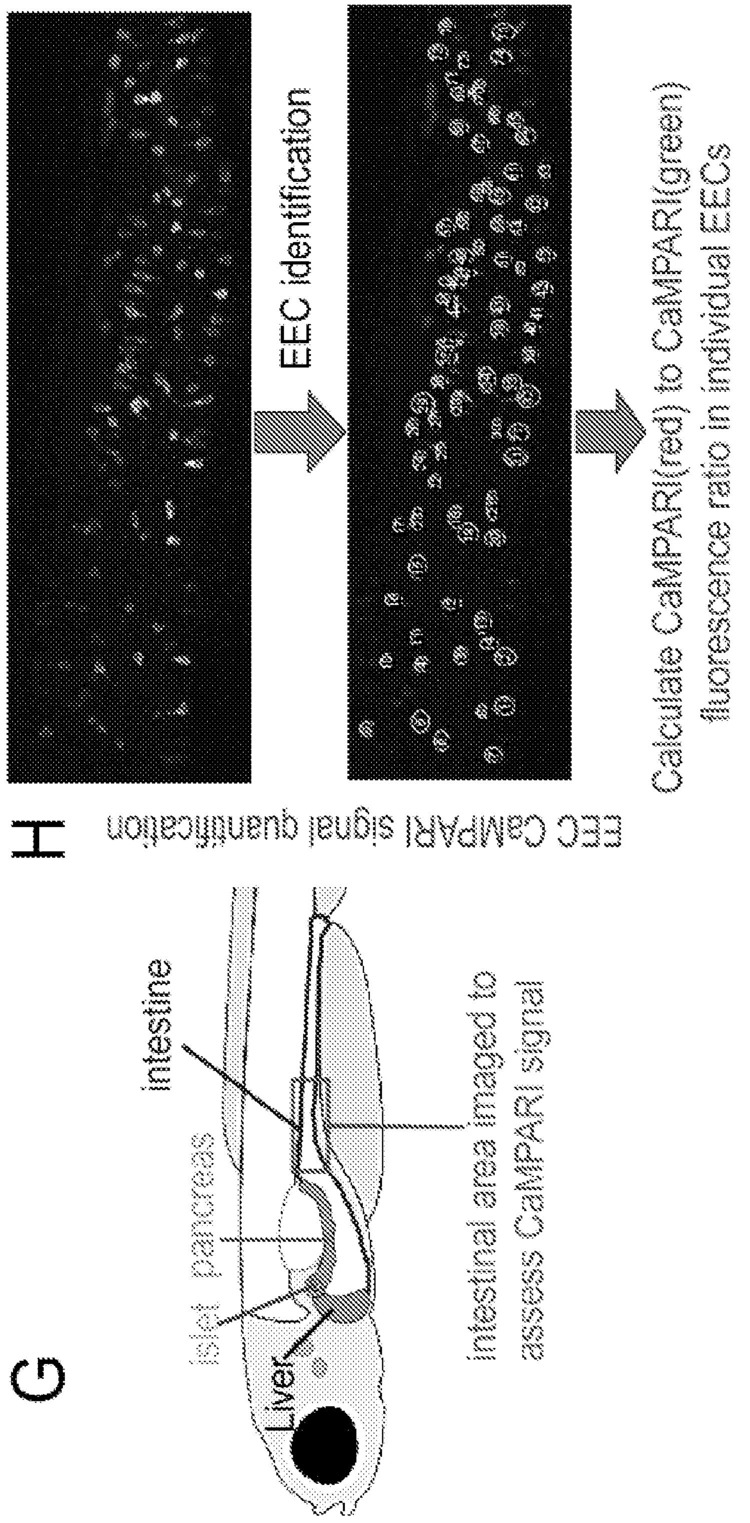
Figures 2I, 2J:
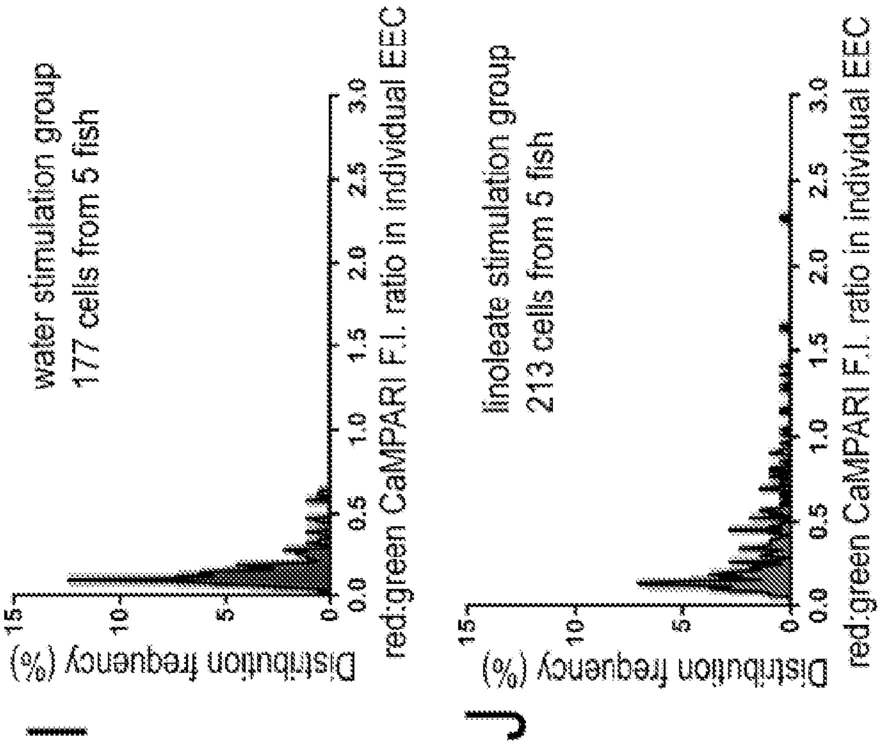
Figures 2K, 2L, 2M, 2N, 2O, 2P:
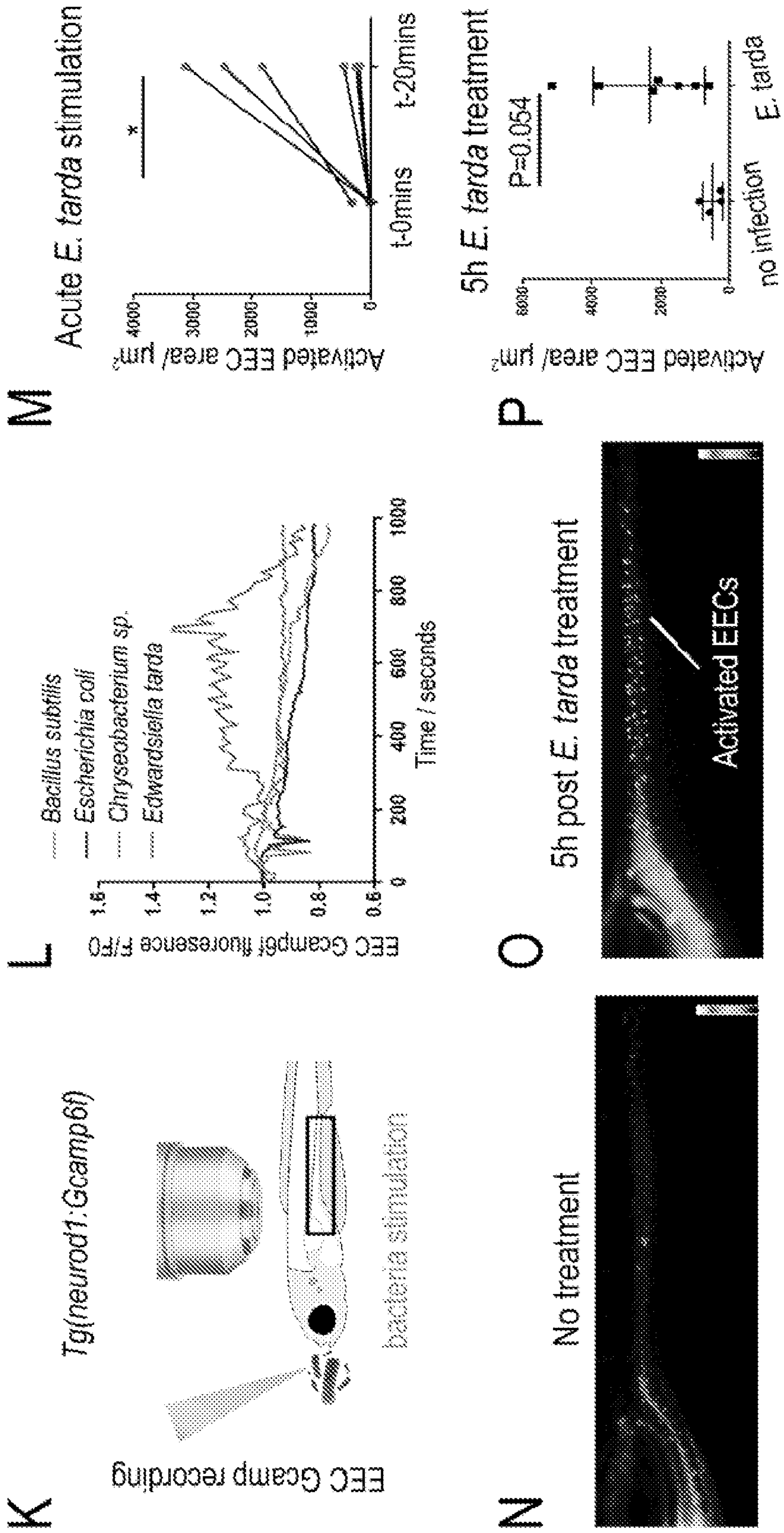

The EEC-CAMPARI system was next used to investigate whether EECs acutely respond to live bacterial stimulation in vivo. Tg(neurod1:CaMPARI) zebrafish were exposed to individual bacterial strains for 20 mins in zebrafish housing water (GZM), followed by photoconversion and imaging of CAMPARI fluorescence. For these experiments, a panel of 11 bacterial strains including 3 model species (*P. aeruginosa, E. coli, B. subtilis*), 7 commensal strains isolated from the zebrafish intestine (Rawls et al., 2006, Stephens et al., 2016), and the pathogen *E. tarda* FL6-60 (also called *E. piscicida* (Abayneh et al., 2013, Bujan et al., 2018) were used; FIG. 1K and Table 2). Within this panel, the only strain that induced a high red:green EEC-CAMPARI signal was *E. tarda* (FIGS. 1G-K). It was further confirmed that *E. tarda* directly activates EECs using an alternative reporter of EEC activity based on the $[Ca^{2+}]_i$-sensitive fluorescent protein Gcamp6f (neurod1:Gcamp6f) (FIG. 1L, FIGS. 21K-P) (Ye et al., 2019). Although *E. tarda* has been reported to infect zebrafish (Abayneh et al., 2013, Flores et al., 2020), no overt pathogenesis was observed in these acute exposure experiments.

TABLE 2

| Key Resources Table | | |
|---|---|---|
| REAGENT or RESOURCE | SOURCE | IDENTIFIER |
| Antibodies | | |
| Chicken anti-GFP Polyclonal antibody | Aves Lab | Cat# GFP-1010, RRID:AB_2307313 |
| Living Colors ® anti DsRed Polyclonal Antibody | TAKARA | Cat# 632496, RRID:AB_10013483 |
| Mouse anti-zebrafish gut secretory cell epitopes Monoclonal antibody [FIS 2F11/2] | Abcam | ab71286 |
| Mouse anti-zebrafish Zn-12 Monoclonal antibody | ZIRC | AB_10013761 |
| Rabbit anti-serotonin whole Polyclonal antibody | Sigma | Cat# 5545 |
| Mouse anti-p44/42 MAPK (Erk1/2) (L34F12) Monoclonal antibody | Cell Signaling | Cat# 4696 |
| Rabbit anti-Phospho-p44/42 MAPK (Erk1/2) (Thr202/Tyr204) (D13.14.4E) Monoclonal antibody | Cell Signaling | Cat# 4370T |
| Rabbit anti-chicken desmin Polyclonal Antibody | Sigma | Cat# D8281 |
| Rabbit anti-mouse PYY antibody | PMID: 28614796 | Custom antibody generated in Liddle Laboratory, aa4-21 (mouse) |
| Bacterial and Virus Strains | | |
| *Edwardsiella tarda* FL6-60 | PMID: 22003892 | N/A |
| *Edwardsiella tarda* LSE40; pmkb:mCherry | Gift by Mark Cronan | N/A |
| *Edwardsiella tarda* 23685 | ATCC | ATCC[23685] |
| *Edwardsiella tarda* 15974 | ATCC | ATCC[15974] |
| *Acinetobacter* sp. ZOR0008 | PMID: 26339860 | N/A |
| *Aeromonas veronii* ZOR0002 | PMID: 26339861 | N/A |
| *Shewanella* sp. ZOR0012 | PMID: 26339862 | N/A |
| *Enterobacter* sp. ZOR0014 | PMID: 26339863 | N/A |
| *Vibrio* sp. ZWU0020 | PMID: 26339864 | N/A |
| *Chryseobacterium* sp. ZOR0023 | PMID: 26339865 | N/A |
| *Exiguobacterium acetylicum* ZWU0009 | PMID: 26339866 | N/A |
| *Bacillus subtilis* 168 | PMID: 18723616 | N/A |
| *Pseudomonas aeruginosa* PAK | PMID: 30524971 | N/A |
| *Plesiomonas* sp. ZOR0011 | PMID: 26339861 | N/A |
| *Escherichia coli* MG1655 | PMID: 26339862 | N/A |
| Chemicals, Peptides, and Recombinant Proteins | | |
| Optovin | Tocris Biotech | 4901 |
| HC030031 | Sigma | 377430-5g |
| Allyl isothiocyanate | Sigma | H4415-10MG |
| Atropine | Sigma | A0132 |
| 4-DAMP | Sigma | SML0255 |
| Clozapine | Sigma | C6305 |
| α-Bungarotoxin | Sigma | 203980 |

TABLE 2-continued

| Key Resources Table | | |
|---|---|---|
| REAGENT or RESOURCE | SOURCE | IDENTIFIER |
| Indole-3-carboxaldehyde | Sigma | 129445 |
| Indole-acetaldehyde | Ambeed | A626636 |
| Indole | Sigma | I3408-25G |
| L-Tryptophan | Sigma | T8941-10mg |
| Indole-3-acetic acid sodium salt | Sigma | I5148-2G |
| Indole-3-pyruvic acid | Sigma | I7017 |
| Indole-3-acetamide | Sigma | 286281-1G |
| Tryptophol | Sigma | T90301-5G |
| CH030031 | Sigma | C8124-5M |
| Folic acid | Sigma | F7876-1G |
| Deposited Data | | |
| Raw and analyzed data | This paper | GSE151711 |
| Experimental Models: Cell Lines | | |
| HEK-293T cells | ATCC | ATCC-CRL-1573 |
| Experimental Models: Organisms/Strains | | |
| Zebrafish: Tg(neurod1:CaMPARI)$^{rdu78}$ | This paper | N/A |
| Zebrafish: Tg(-5kbneurod1:Gcamp6f)$^{icm05}$ | PMID: 27231612 | N/A |
| Zebrafish: TgBAC(cldn15la:EGFP)$^{pd1034}$ | PMID: 24504339 | N/A |
| Zebrafish: Tg(-5kbneurod1:TagRFP)$^{w69}$ | PMID: 22738203 | N/A |
| Zebrafish: TgBAC(trpa1b:EGFP)$^{a129}$ | PMID: 22190641 | N/A |
| Zebrafish: Tg(neurod1:cre; cmlc2:EGFP)$^{rdu79}$ | This paper | N/A |
| Zebrafish: TgBAC(gata5:loxp-mcherry-stop-loxp-DTA)$^{pd315}$ | This paper | N/A |
| Zebrafish: trpa1b mutant$^{vu197}$ | PMID: 18829968 | N/A |
| Zebrafish: trpa1a mutant$^{hu2163}$ | PMID: 18829968 | N/A |
| Zebrafish: TgBAC(neurod1:EGFP)$^{nl1}$ | PMID: 19424431 | N/A |
| Zebrafish: Tg(-5kbneurod1:Gal4; cmlc2:EGFP)$^{rdu71}$ | PMID: 31793875 | N/A |
| Zebrafish: Tg(-5kbneurod1:Lifeact-EGFP)$^{rdu70}$ | PMID: 31793875 | N/A |
| Zebrafish: Tg(UAS:ChR2(H134R)-mCherry)$^{s1985}$ | PMID: 26752076 | N/A |
| Zebrafish: Tg(NBT:DsRed)$^{zf148}$ | PMID: 29628374 | N/A |
| Zebrafish: ret mutant$^{hu2846}$ | PMID: 21490065 | N/A |
| Zebrafish: sox10 mutant$^{t3}$ | PMID: 28207737 | N/A |
| Zebrafish: TgBAC(chata:Gal4)$^{mpn202}$ | PMID: 28701772 | N/A |
| Zebrafish: Tg(UAS:Gcamp6s)$^{mpn101}$ | PMID: 28701772 | N/A |
| Zebrafish: Tg(UAS:NTR-mCherry)$^{c264}$ | PMID: 24496182 | N/A |
| Zebrafish: Tg(isl1:EGFP)$^{rw0}$ | PMID: 23850871 | N/A |

TABLE 2-continued

| Key Resources Table | | |
|---|---|---|
| REAGENT or RESOURCE | SOURCE | IDENTIFIER |
| Zebrafish: tph1b mutant$^{pd249}$ | PMID: 28811310 | N/A |
| Zebrafish: Tg(tph1b:mCherry-NTR)$^{pd275}$ | This paper | N/A |
| Zebrafish: Tg(β-act2:Brainbow1.0L)$^{pd50}$ | PMID: 22538609 | N/A |
| Zebrafish: Tg(neurod1:CaMPARI)$^{rdu78}$ | This paper | N/A |
| Zebrafish: Tg(-5kbneurod1:Gcamp6f)$^{icm05}$ | PMID: 27231612 | N/A |
| Zebrafish: TgBAC(cldn15la:EGFP)$^{pd1034}$ | PMID: 24504339 | N/A |
| Zebrafish: Tg(-5kbneurod1:TagRFP)$^{w69}$ | PMID: 22738203 | N/A |
| Zebrafish: Tg(-5kbneurod1:mitoEos)$^{Y586}$ | PMID: 30410881 | N/A |
| Mouse: C57BL/6J | Jackson Laboratory | 000664 |
| Oligonucleotides | | |
| RT-qPCR for zebrafish gene: pyyb NM_001327895 | Eurofins Genomics | AGCGTATCCACCCAAACCTG (SEQ ID NO: 1) GCCGGATGTCCTGTTCATCA (SEQ ID NO: 2) |
| RT-qPCR for zebrafish gene: ccka XM_001346104 | Eurofins Genomics | AACCAAAGGCTCATACCGCA (SEQ ID NO: 3) TCATATTCCTCGGCGCTTCG (SEQ ID NO: 4) |
| RT-qPCR for zebrafish gene: adcyap1a NM_152885 | Eurofins Genomics | GGGGTTTTCACGGACAGCTA (SEQ ID NO: 5) TGTGTCACAAAGCCGGGAAT (SEQ ID NO: 6) |
| RT-qPCR for zebrafish gene: insl5a NM_001037669 | Eurofins Genomics | TGCTGTAAGCAGACGAGACC (SEQ ID NO: 7) AGCAGAGGAACGTCAGGTCA (SEQ ID NO: 8) |
| RT-qPCR for zebrafish gene: fabp2 NM_131431 | Eurofins Genomics | TGGAAAGTCGACCGCAATGA (SEQ ID NO: 9) TGAACTTGTCTCCGGTCTGC (SEQ ID NO: 10) |
| RT-qPCR for zebrafish gene: muc5.3 XM_021477626 | Eurofins Genomics | ATGCGAACCATGGGGCTTTA (SEQ ID NO: 11) TTGTTCGCGTTCCCGTCATA (SEQ ID NO: 12) |
| RT-qPCR for zebrafish gene: sypa NM_001143977 | Eurofins Genomics | GATCGTGGCACCGTTTATGC (SEQ ID NO: 13) ATTGTAGCCTTGCTGGCTGT (SEQ ID NO: 14) |
| RT-qPCR for zebrafish gene: sypb NM_001030242 | Eurofins Genomics | ATCCTATGGGGAGGCAACCT (SEQ ID NO: 15) ACCTTCCTGTCCATAGCCCT (SEQ ID NO: 16) |
| RT-qPCR for zebrafish gene: agr2 NM_001012481 | Eurofins Genomics | AGTGCTCTTGGTCATGGTGG (SEQ ID NO: 17) AGGGGCTTGTTCTTGGATCG (SEQ ID NO: 18) |
| RT-PCR for zebrafish gene: trpa1a NM_001007065 | Eurofins Genomics | TACCAACATGTCGTGTTTTCAGTG (SEQ ID NO: 19) GATTGCACACAACCGGTTTACA (SEQ ID NO: 20) |
| RT-PCR for zebrafish gene: trpa1b NM_001007066 | Eurofins Genomics | CTCATTTGTCTTGGAAAGGGAGC (SEQ ID NO: 21) GGAGGAAGTTGCGACCTGTT (SEQ ID NO: 22) |

Figures 3A, 3B, 3C:
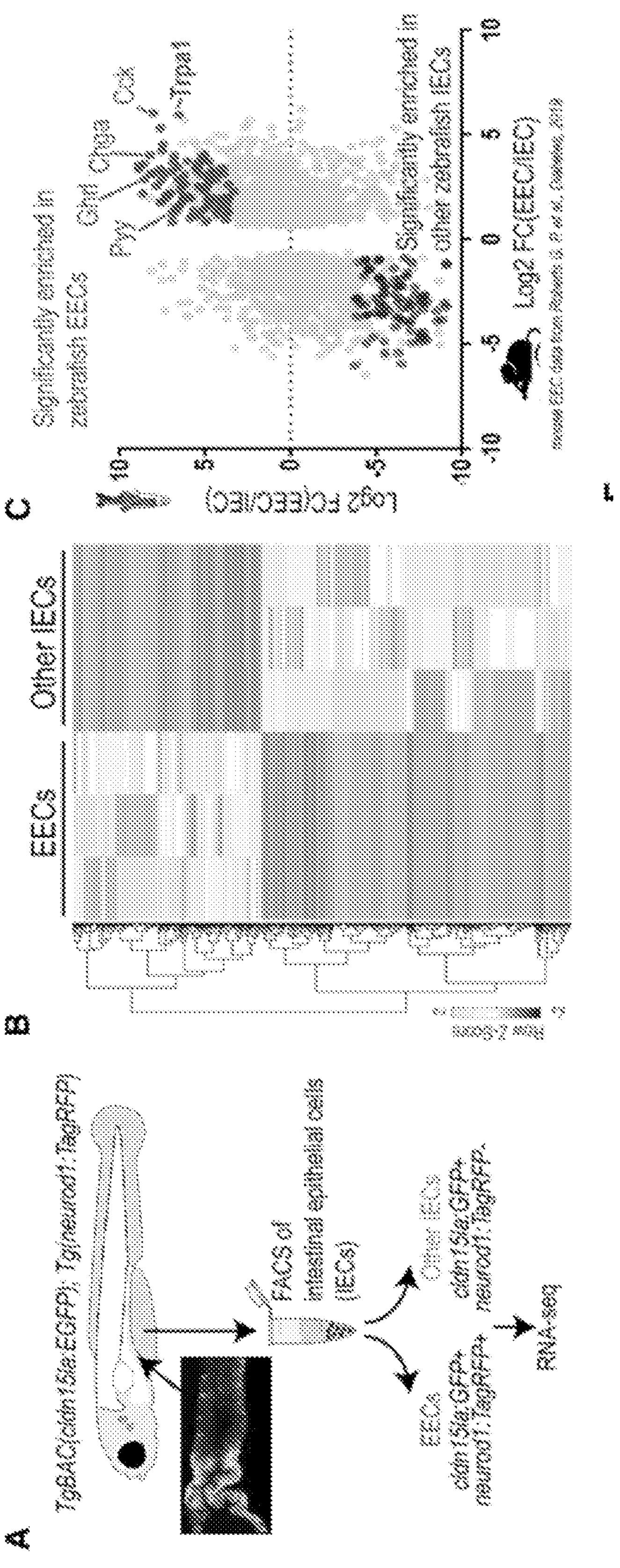
FIG. 3. *E. tarda* activates EECs through Trpa1. (A) Schematic diagram of zebrafish EEC RNA-seq. (B) Clustering of genes that are significantly enriched in zebrafish EECs and other IECs ($P_{adj}$<0.05). (C) Comparison of zebrafish and mouse EEC enriched genes. Mouse EEC RNA-seq data was obtained from GSE114913 (Roberts et al., 2019). (D) Fluorescence image of TgBAC(trpa1b:EGFP). Zoom-in view shows the expression of trpa1b+ cells in intestine. (E) Confocal projection of a TgBAC(trpa1b:EGFP); Tg(neurod1:TagRFP) zebrafish intestine. Yellow arrows indicate zebrafish EECs that are trpa1b:EGFP+. (F) Quantification of EEC Gcamp responses to Trpa1 agonist AITC stimulation in trpa1b+/+, trpa1b+/− and trpa1b−/− zebrafish. (G) Experimental design. (H-I) Confocal projection of Tg(neurod1:CaMPARI) zebrafish intestine stimulated with *E. tarda* with or without the Trpa1 antagonist HC030031. (J) Quantification of activated EECs in control and HC030031 treated zebrafish treated with water or *E. tarda*. (K) Experimental approach. (L-M) Confocal projection of trpa1b+/+ or trpa1b−/− Tg(neurod1:CaMPARI) intestine after stimulation with water or *E. tarda*. (N) Quantification of activated EEC percentage in WT and trpa1b−/− zebrafish treated with water or *E. tarda*. (O) Experimental design. (P-Q) Timed images of trpa1b+/+ or trpa1b−/− Tg(neurod1:Gcamp6f) zebrafish stimulated with *E. tarda*. (R) Quantification of relative EEC Gcamp6f fluorescence intensity in WT or trpa1b−/− zebrafish treated with *E. tarda*. One-way ANOVA with Tukey's post-test was used in F, J, N. *p<0.05; p<0.01; *p<0.001; ****p<0.0001.

EECs express a variety of sensory receptors that can be activated by different environmental stimuli. To investigate the mechanisms by which EECs perceive *E. tarda* stimulation, EECs were isolated from zebrafish larvae and RNA-seq analysis was performed. Transcript levels in FACS-sorted EECs (cldn15la:EGFP+; neurod1:TagRFP+) were compared to all other intestinal epithelial cells (IECs) (cldn15la:EGFP+; neurod1:TagRFP−) (FIG. 3A). 192 zebrafish transcripts that were significantly enriched in EECs were identified by DESeq2 using $P_{FDR}<0.05$ (FIG. 3B). Gene Ontology analysis revealed that those zebrafish genes are enriched for processes like hormone secretion, chemical synaptic transmission and neuropeptide signaling. To identify gene homologs enriched in EECs in both zebrafish and mammals, these 192 genes were compared to published RNA-seq data from Neurod1+ EECs from mouse duodenum and CHGA+ EECs from human jejunum (Roberts et al., 2019). Despite the evolutionary distance and differences in tissue origin, that 24% of zebrafish EEC-enriched gene homologs (46 out of 192) were shared among zebrafish, human, and mouse, and that 40% of zebrafish EEC-enriched genes (78 out of 192) were shared between zebrafish EECs and human jejunal EECs. The genes with conserved EEC expression include those encoding hormones, transcription factors, G-protein coupled receptors, and ion channels that regulate membrane potential (FIG. 3C). Using published data from mouse intestinal epithelial single-cell RNA-seq data that revealed different EEC subtypes (Haber et al., 2017), many of the signature genes in mouse enterochromaffin cells (EC), which are identified by their 5-HT synthesis, were found to be enriched in zebrafish EECs. Among these conserved EEC-enriched genes, one of the genes with the highest expression in zebrafish EECs is transient receptor potential ankyrin 1 (Trpa1) (FIG. 3C).

Trpa1 is a nociception receptor that is known to mediate pain sensation in nociceptive neurons (Lapointe and Altier, 2011). A broad spectrum of chemical irritants, including many compounds that are derived from food spices, activate Trpa1 (Nilius et al., 2011). In addition to chemical irritants, certain bacterial products, including lipopolysaccharide (LPS) and hydrogen sulfide ($H_2S$), stimulated nociceptive neurons in a Trpa1-dependent manner (Meseguer et al., 2014). The zebrafish genome encodes two trpa1 paralogs, trpa1a and trpa1b (Prober et al., 2008). The data presented herein establish that trpa1b, but not trpa1a, is expressed by a subset of zebrafish EECs and is required for EEC activation by Trpa1 agonist AITC (FIGS. 3D-F, FIGS. 4B-G). Since the expression of classic microbial pattern recognition receptors is very low in zebrafish EECs, it was next tested if Trpa1 mediated *E. tarda*-induced EEC activation. Treatment of wild-type (WT) Tg(neurod1:CAMPARI) fish with the Trpa1 antagonist HC030031 significantly inhibited *E. tarda*'s ability to induce EEC activation (FIGS. 3G-J). The ability of *E. tarda* to induce EEC activity in the EEC-CAMPARI model was similarly blocked in trpa1b mutant zebrafish (FIGS. 3K-N). In accord, experiments in Tg(neurod1:Gcamp6f) zebrafish confirmed that Gcamp6f fluorescence increased in EECs in response to *E. tarda* stimulation in WT, but not trpa1b mutant zebrafish (FIGS. 3O-R). Therefore live *E. tarda* bacteria stimulate EECs in a Trpa1-dependent manner, suggesting that EEC Trpa1 signaling may play an important role in mediating microbe-host interactions.

EEC Trpa1 Signaling is Important to Maintain Microbial Homeostasis by Regulating Intestinal Motility To determine how *E. tarda*-induced Trpa1 signaling in EECs affects the host, trpa1b+/+ and trpa1b$^{-/-}$ zebrafish larvae were exposed to an *E. tarda* strain expressing mCherry fluorescent protein. High-dose ($10^7$ CFU/mL) *E. tarda* exposure for 3 days decreased survival rate and caused gross pathology (FIGS. 4M-N), consistent with its reported activity as a zebrafish pathogen (Abayneh et al., 2013, Flores et al., 2020). To investigate the interaction between *E. tarda* and Trpa1+EECs under relatively normal physiological conditions, zebrafish were exposed to a low *E. tarda* dose ($10^6$ CFU/mL) that did not significantly affect survival rate or cause gross pathology (FIGS. 4M-N and FIG. 5A). When reared under conventional conditions in the absence of *E. tarda*, no significant difference in the abundance of culturable gut microbes between trpa1b$^{+/+}$ and trpa1b$^{-/-}$ zebrafish was observed (FIGS. 4H-I). However, upon 3-day treatment with *E. tarda*, there was significant accumulation of *E. tarda* mCherry$^+$ bacteria in the intestinal lumen in trpa1b$^{-/-}$ but not trpa1b$^{+/+}$ zebrafish larvae (FIGS. 5A-C). This accumulation could be observed by either quantifying intestinal *E. tarda* mCherry fluorescence (FIG. 5D) or counting *E. tarda* colony forming units (CFU) from digestive tracts dissected from *E. tarda* treated trpa1b$^{+/+}$ and trpa1b$^{-/-}$ zebrafish (FIG. 5E). This suggests that Trpa1 signaling may act as a host defense mechanism to facilitate clearance of specific types of bacteria such as *E. tarda*.

In addition to EECs, Trpa1 is also expressed in mesenchymal cells within the intestine (FIGS. 5D-E and FIG. 6O) and nociceptive sensory neurons (Yang et al., 2019, Holzer, 2011). To test if the phenotype observed above is specifically mediated by EECs, a new Cre-loxP transgenic system was generated that permits specific ablation of EECs without affecting other IECs or other neurod1 expressing cells like CNS or pancreatic islets (FIG. 5F, FIG. 4J). Quantitative RT-PCR and immunofluorescence confirmed a reduction of EEC hormones but not non-EEC marker genes (FIGS. 4K-L). Establishing this EEC ablation system allowed investigation of the specific role of EECs in mediating *E. tarda*-host interaction. As with trpa1b$^{-/-}$ zebrafish, no significant differences in gut microbial abundance between unexposed WT and EEC-ablated zebrafish were detected (FIG. 4O). However, in response to *E. tarda* exposure, a significantly higher amount of *E. tarda* mCherry accumulated in EEC-ablated zebrafish compared to WT sibling controls (FIG. 5H and FIGS. 4P-Q). Together, these data establish that EEC Trpa1 signaling maintains gut microbial homeostasis by facilitating host clearance of specific types of bacteria like *E. tarda*.

Figure 8A:
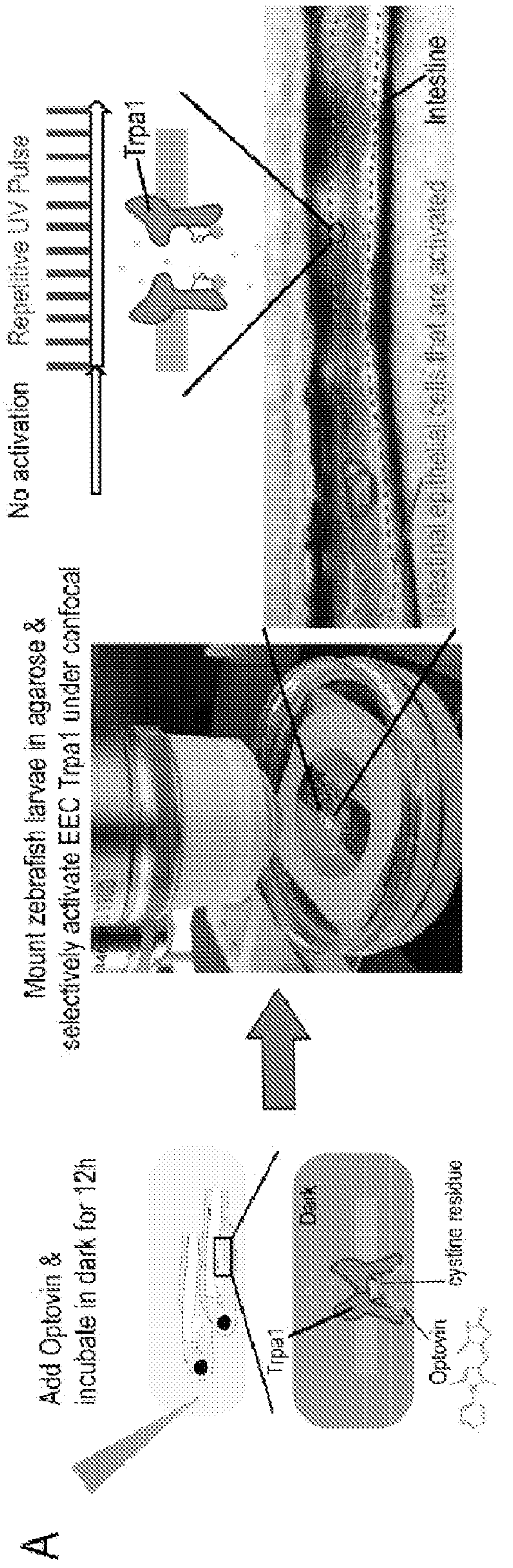
FIG. 8. Activation of EEC Trpa1 signaling promotes intestinal motility, related to FIG. 7. (A) Experimental design for activating EEC Trpa1 signaling using Optovin-UV. (B) Confocal image of Tg(neurod1:Gcamp6f); Tg(neurod1:TagRFP) zebrafish intestine before (images on the left) and after (images on the right) UV light activation. Yellow arrows indicate the subpopulation of EECs exhibiting increased Gcamp fluorescence following UV activation. (C) Quantification of the EEC Gcamp6f to TagRFP fluorescence ratio before and after UV activation. (D) Schematic of intestinal movement in larval zebrafish. The proximal zebrafish intestine exhibits retrograde movement while mid-intestine and distal intestine exhibit anterograde movement. The imaged and UV light activated intestinal region in the Optovin-UV experiment is indicated by the red box. The μ velocity indicates intestinal horizontal movement. A positive value indicates anterograde movement and a negative value indicates retrograde movement. The v velocity indicates intestinal vertical movement. (E) Quantification of intestinal motility using PIV-LAB velocity analysis before and after UV activation. Note that Optovin-UV induced Trpa1 activation increased u velocity (horizontal movement) more than v velocity (vertical movement). (F) Confocal image of ChR2+Trpa1+ EECs (yellow circles, top image) and ChR2+Trpa1-EECs (red circles, bottom image) in TgBAC(trpa1b:EGFP); Tg(neurod1:Gal4); Tg(UAS:ChR2-mCherry) zebrafish. (G) Quantification of μ velocity following blue light activation of ChR2+Trpa1+ or ChR2+Trpa1-EECs. (H) Quantification of mean intestinal velocity magnitude change before and after blue light activation of ChR2+Trpa1-EECs. (I) Quantification of mean intestinal velocity magnitude in response to *E. tarda* gavage in trpa1b+/+ or trpa1b−/− zebrafish. Student t-Test was used in I. ***P<0.001.

To understand the mechanisms by which EEC Trpa1 regulates gut microbial homeostasis, an opto-pharmacological approach that permits temporal control of EEC Trpa1 activation through UV light exposure was used (FIG. 7A). Zebrafish were pretreated with Optovin, a chemical that specifically activates Trpa1 only in the presence of UV light (Kokel et al., 2013) (FIG. 8A). To specifically activate Trpa1 in EECs, zebrafish larvae pretreated with Optovin were mounted and restricted UV light exposure specifically to the intestinal epithelium using a confocal laser (FIG. 8A). UV light activation significantly increased $[Ca^{2+}]_i$ in a subpopulation of EECs in WT larvae, as measured by Gcamp6f fluorescence (FIGS. 8B-C). The same UV light exposure in trpa1b−/− larvae pretreated with Optovin did not increase EEC $[Ca^{2+}]_i$ (FIGS. 7B-C), indicating that EEC activation induced by Optovin-UV was dependent on Trpa1. Next, this approach was used to examine the effect of EEC Trpa1 activation on intestinal motility. Trpa1 activation in EECs within the middle intestine via UV light application in WT larvae produced a propulsive movement of the intestine from anterior to posterior, and the velocity of intestinal motility increased accordingly (FIGS. 7D-F, FIGS. 8D-E. In contrast, Optovin treatment and UV activation failed to induce intestinal motility in EEC-ablated zebrafish (FIGS. 74D-F). These results indicate that intestinal motility triggered by Trpa1 activation is dependent on EECs.

To further test if signaling from Trpa1+EECs is sufficient to activate intestinal motility, \ a new optogenetic system was used in which a mCherry tagged Channelrhodopsin (ChR2-mCherry) is expressed in EECs from the neurod1 promoter (FIGS. 7G-H). Blue light activation of ChR2 causes cation influx and plasma membrane depolarization, and $[Ca^{2+}]_i$ then increases through the activation of voltage-dependent calcium channels (Nagel et al., 2003) which are abundantly expressed in zebrafish EECs (FIGS. 7I-J). This new tool permits selective activation of the ChR2-mCherry+ EECs using a confocal laser without affecting the activity of nearby EECs (FIG. 8F). Therefore, Tg(neurod1:Gal4); Tg(UAS:ChR2-mCherry); TgBAC(trpa1b:EGFP) larvae were used to selectively activate ChR2-mCherry expressing EECs that are either trpa1b+ or trpa1b−. Activation of trpa1b+ EECs but not trpa1b− EECs consistently increased intestinal velocity magnitude (FIGS. 7K-L, FIGS. 8F-H), again indicating a unique role for Trpa1+EECs in regulating intestinal motility. Consistent with the Optovin-UV result, stimulating Trpa1+ChR2+ EECs in the middle intestine resulted in anterograde intestinal movement. Interestingly, stimulating Trpa1+ChR2+ EECs in the proximal intestine initiated a retrograde intestinal movement. This is consistent with previous findings that the zebrafish proximal intestine typically exhibits a retrograde motility pattern whereas the middle and distal intestine display antegrade motility (FIG. 8D) (Roach et al., 2013).

Finally, it was tested whether microbial activation of Trpa1 signaling in EECs also increased intestinal motility. Using microgavage (Cocchiaro and Rawls, 2013), delivery of live *E. tarda* into the intestinal lumen was found to significantly promote intestinal peristalsis and motility compared to PBS-gavaged controls (FIGS. 7M-O). *E. tarda* induced intestinal motility was significantly reduced in trpa1b−/− zebrafish (FIG. 8I). Zebrafish were then gavaged with *Aeromonas* or *Bacillus*, two of the tested bacterial strains that do not activate EECs (FIG. 1), no significant change of intestinal motility was observed (FIGS. 7M-O). These experiments together establish that activation of Trpa1 in EECs directly stimulates intestinal motility, and provide a potential physiologic mechanism underlying Trpa1-dependent clearance of *E. tarda* from the intestinal lumen.

EEC Trpa1 Signaling Promotes Intestinal Motility by Activating Cholinergic Enteric Neurons To test the role of the ENS in Trpa1-activated intestinal motility, zebrafish that lack an ENS due to mutation of the receptor tyrosine kinase gene ret (Taraviras et al., 1999) were used. Immunofluorescence demonstrated that $ret^{-/-}$ zebrafish lack all identifiable enteric nerves (marked by NBT transgenes, FIG. 9B and FIGS. 6A-B), whereas EECs remain intact (marked by neurod1 transgenes, FIG. 9B) and responsive to Trpa1 agonist (FIGS. 7C-F). Using the Optovin-UV system (FIG. 9A), it was observed that EEC Trpa1 activation increased intestinal motility in control ($ret^{+/+}$ or $ret^{+/-}$) but not $ret^{-/-}$ zebrafish (FIGS. 9C-D and FIGS. 7G-H). These results were confirmed using a second zebrafish mutant that lacks an ENS due to mutation of the transcription factor gene sox10 (Bondurand and Sham, 2013) (FIGS. 7I-N). These data suggest that Trpa1+ EECs do not signal directly to enteric smooth muscle to promote intestinal motility, but instead signal to the ENS.

The ENS is a complex network composed of many different neuronal subtypes. Among these subtypes, cholinergic neurons secrete the excitatory neurotransmitter acetylcholine to stimulate other enteric neurons or smooth muscle (Pan and Gershon, 2000, Qu et al., 2008) and are essential for normal intestinal motility (Johnson et al., 2018). One of the key enzymes for the synthesis of acetylcholine in the ENS is choline acetyltransferase (Chat) (Furness et al., 2014). Using TgBAC(chata:Gal4); Tg(UAS:NTR-mCherry) transgenic zebrafish, cholinergic enteric neurons in the zebrafish intestine were observed (FIG. 9E and FIGS. 10E-J). It was found that chata+ neurons have smooth cell bodies which are located within the intestinal wall, many of which display multiple axons (FIG. 9E and FIGS. 10E-F). Such multipolar neurons have also been classified as Dogiel type II neurons (Cornelissen et al., 2000). These Dogiel type II neurons are likely to be the intestinal intrinsic primary afferent neurons (IPANs) (Bornstein, 2006). These results indicate that some EECs including Trpa1+EECs form direct contacts with nerve fibers extending from chata+ enteric neurons (FIGS. 9F-H and FIGS. 10G-J). In addition, it was found that zebrafish EECs are enriched for transcripts encoding presynaptic vesicle proteins (FIG. 10P) and forms neuropod structure to connect with neurons (FIGS. 10A-D) similar as previous findings in mouse EECs (Bohorquez et al., 2015, Bellono et al., 2017, Kaelberer et al., 2018).

To investigate whether activation of Trpa1+EECs stimulates chata+ enteric neurons, TgBAC(chata:Gal4); Tg(UAS:Gcamp6s) zebrafish were used, which permit recording of in vivo calcium activity in chata+ neurons (FIGS. 9I-J). Upon Trpa1+EEC activation, Gcamp6s fluorescence increased in chata+ enteric neurons (FIGS. 9K, L). Trpa1 is not expressed in chata+ enteric neurons or in any other ENS cells (FIGS. 11O-R), indicating that chata+ enteric neurons cannot be directly activated by optic Trpa1 stimulation but are instead activated via stimulation by Trpa1+ EECs. In addition to the ENS, efferent vagal nerves also play an important role in modulating intestinal motility (Travagli and Anselmi, 2016). However, similar Trpa1+EEC induced intestinal motility change and chata+ enteric neuron activation was observed in zebrafish whose intestine is anatomically disconnected from the CNS (FIGS. 10K-O), suggesting that vagal efferent nerves are not required for Trpa1+EEC induced intestinal motility, and that Trpa1+EEC induced intestinal motility is mediated by intrinsic enteric circuitry which likely involves chata+ enteric neurons.

Previous mouse studies demonstrated that Trpa1 mRNA is highly enriched in 5-HT-secreting EC cells in the small intestine of mammals (Nozawa et al., 2009). Immunofluorescence staining indicated that, similar to mammals, 5-HT expression in the zebrafish intestinal epithelium is also highly enriched in Trpa1+EECs (FIG. 9M). 5-HT in EECs is synthesized from tryptophan via tryptophan hydroxylase 1 (Tph1) (Li et al., 2011). Zebrafish possess two Tph1 paralogs, tph1a and tph1b (Ulhaq and Kishida, 2018), but only tph1b is expressed in zebrafish EECs (FIG. 10S). The expression of tph1b in Trpa1+EECs was also confirmed by crossing a new Tg(tph1b:mCherry-NTR) transgenic line to TgBAC(trpa1b:EGFP) zebrafish (FIG. 9N and FIGS. 10Q-R, T-U). To investigate whether 5-HT mediates EEC Trpa1-induced intestinal motility, it was tested whether a similar response was present in $tph1b^{+/+}$ and $tph1b^{-/-}$ zebrafish larvae (Tornini et al., 2017) using the Optovin-UV platform. Under baseline conditions, no significant difference in intestinal motility between $tph1b^{+/+}$ and tph1b−/− zebrafish was observed (FIG. 10V). However, in response to UV stimulated EEC Trpa1 activation, intestinal motility was significantly reduced in tph1b$^{-/-}$ compared to tph1b$^{+/+}$ zebrafish (FIG. 9O). These findings suggest a working model in which Trpa1+EECs signal to cholinergic enteric neurons through 5-HT, which in turn stimulates intestinal motor activity and promotes intestinal motility.

Chemical and Microbial Stimulation of EEC Trpa1 Signaling Activate Vagal Sensory Ganglia The intestine is innervated by both intrinsic ENS and extrinsic sensory nerves from the brain and spinal cord (Brookes et al., 2013). In mammals, afferent neuronal cell bodies of the vagus nerve reside in the nodose ganglia and travel from the intestine to the brainstem to convey visceral information to the CNS. However, in zebrafish, it is unknown if the vagal sensory system innervates the intestine. The zebrafish vagal sensory ganglia can be labelled using TgBAC(neurod1:EGFP) or immunofluorescence staining of the neuronal marker acetylated α Tubulin (AcαTub) (FIG. 12B). Using lightsheet confocal imaging, it was demonstrated that not only do the vagal ganglion in zebrafish extend projections to the intestine (FIGS. 12B-C and FIGS. 11A-B) but vagal sensory nerve fibers directly contact a subpopulation of EECs (FIG. 12D). Using the Tg(neurod1:cre); Tg(β-act2:Brainbow) transgenic zebrafish system (Gupta and Poss, 2012) (Vagal-Brainbow), in which individual vagal ganglion cells are labeled with different fluorescent colors through Cre recombination (Foglia et al., 2016) (FIG. 11C), it was revealed that the zebrafish vagal sensory ganglia cells also directly project to the vagal sensory region in the hindbrain (FIGS. 12E-F). Using this Vagal-Brainbow system, it was found that vagal sensory nerves are labelled by Cre recombination in both the proximal and distal intestine (FIGS. 12D-G).

To further visualize the vagal sensory network in zebrafish, Tg(isl1:EGFP) zebrafish were used in which EGFP is expressed in vagal sensory ganglia and overlaps with neurod1 (FIG. 12G and FIGS. 1H-J). Data revealed that after leaving the vagal sensory ganglia, the vagus nerve travels along the esophagus and enters the intestine in the region between the pancreas and the liver (FIG. 12G and FIGS. 11I-J). Direct contact of EECs and the vagus nerve could also be observed in Tg(isl1:EGFP); Tg(neurod1:TagRFP) zebrafish (FIG. 12H). These data demonstrate the existence of a vagal network in the zebrafish intestine.

Next, it was investigated whether this vagal network is activated in response to enteric microbial stimulation with *E. tarda*. Tg(neurod1:Gcamp6f); Tg(neurod1:TagRFP) zebrafish larvae were gavaged with either PBS or live *E. tarda* bacteria. 30 min after enteric stimulation with Trpa1 agonist AITC or *E. tarda*, but not after PBS vehicle stimulation, Gcamp6f fluorescence intensity significantly increased in a subset of vagal sensory neurons (FIGS. 121-K, FIGS. 11K-L). This result indicated that acute enteric chemical or microbial stimulation directly activated vagal sensory neurons. To further investigate whether the vagal activation induced by enteric *E. tarda* was mediated by Trpa1+EECs, a published method that labels active zebrafish neurons through pERK immunofluorescence (Randlett et al., 2015) was used to measure vagal activity. Delivering AITC into the zebrafish intestine by microgavage (Cocchiaro and Rawls, 2013) increased the number of pERK+ vagal cells compared to PBS treatment (FIGS. 12L-N, R). AITC-induced vagal activation was abrogated in the absence of EECs (FIGS. 12N, R), indicating that Trpa1 signaling in the intestine increases vagal sensory activity in an EEC-dependent manner. Next, live *E. tarda* bacteria were gavaged into both WT and EEC-ablated zebrafish. Similar to Trpa1 chemical agonist stimulation, *E. tarda* gavage increased the number of activated pERK+ vagal sensory neurons in WT zebrafish (FIGS. 12O-Q, S) but not in EEC ablated zebrafish (FIGS. 12Q, S). Furthermore, the vagal activation induced by enteric *E. tarda* was dependent on Trpa, 1 as pERK+ vagal cell number was significantly reduced in *E. tarda* treated trpa1b$^{-/-}$ zebrafish (FIG. 12T). Together, these results reveal that chemical or microbial stimuli in the intestine can stimulate Trpa1+ EECs, which then signal to the vagal sensory ganglia.

Tryptophan Catabolites Secreted from *E. tarda* Activate the EEC Trpa1 Gut-Brain Pathway In order to identify the molecular mechanism by which *E. tarda* activates Trpa1 in EECs, the effects of live and killed *E. tarda* cells and cell-free supernatant (CFS) from *E. tarda* cultures on EEC calcium activity were examined (FIG. 13A). Formalin-killed or heat-killed *E. tarda* cells failed to stimulate EECs, however, CFS, at levels comparable to live *E. tarda* cells, stimulated EECs (FIGS. 13A-B). The ability of *E. tarda* CFS to activate EECs was diminished in trpa1b mutant zebrafish (FIG. 13C), suggesting that a factor secreted from *E. tarda* has the ability to activate Trpa1 in EECs. HPLC-MS analysis revealed that *E. tarda* CFS is enriched for several indole ring-containing tryptophan catabolites (FIG. 13D and FIGS. 14A-C), three of the most abundant being indole, tryptophol (IEt), and indole-3-carboxyaldhyde (IAld) (FIG. 13D and FIGS. 14A-C). To test if other bacteria secrete tryptophan catabolites like *E. tarda*, similar HPLC-MS analysis of CFS from bacteria previously tested for EEC activation was performed (FIG. 1K). Although several tested bacterial strains produced indole or IAld when cultured in nutrient-rich medium (FIG. 14D), *E. tarda* was the only bacteria that uniquely retained a high level of indole and IAld production when cultured in zebrafish GZM housing water (FIG. 13E), consistent with the finding that *E. tarda* uniquely activates zebrafish EECs when added into GZM water (FIG. 1K). To investigate whether these tryptophan metabolites were directly linked with *E. tarda* pathogenesis, two other *E. tarda* strains (*E. tarda* 23685 and *E. tarda* 15974) were tested which were isolated from human gut microbiota and do not cause fish pathogenesis (Yang et al., 2012, Srinivasa Rao et al., 2003, Nakamura et al., 2013). Both *E. tarda* strains activated EECs and exhibited similar indole and IAld secretion capacity as pathogenic *E. tarda* FL6-60 and *E. tarda* LSE40 (FIG. 713E and FIGS. 14G-H). This result suggested that tryptophan catabolites production, EEC Trpa1 activation and its downstream consequences may be distinct from *E. tarda* pathogenesis in fish (Edwardsiellosis) (Park et al., 2012).

It was next tested if *E. tarda* tryptophan catabolites are sufficient to activate EECs. Indole and IAld, but not other tested tryptophan catabolites, strongly activated zebrafish EECs in a trpa1b-dependent manner (FIGS. 13F-G, FIGS. 14F). Indole and IAld also activated the human TRPA1 receptor transfected into HEK cells (FIGS. 13H-J and FIGS. 14I-J). Both indole and IAld exhibited full TRPA1 agonist activity with an efficiency comparable to cinnamaldehyde (CAD), a well characterized TRPA1 activator (FIGS. 13I-J and FIGS. 14I-J) (Macpherson et al., 2007). Both indole and IAld also activated mouse Trpa1, but in a less potent manner (FIG. 14M). Both indole- and IAld-induced human and mouse Trpa1 activation were blocked by the TRPA1 inhibitor A967079 (FIG. 13J and FIGS. 14K-L, N). These results establish that the microbial tryptophan catabolites indole and IAld are novel and evolutionarily-conserved agonists of vertebrate TRPA1.

Next, it was investigated whether indole and IAld can mimic live *E. tarda* bacterial stimulation and activate a similar gut-brain pathway through EEC Trpa1 signaling. Results indicated that enteric delivery of indole or IAld by microgavage increased Gcamp6f fluorescence in a subset of vagal sensory neurons (FIGS. 13K-O, FIGS. 15E-F) and stimulating zebrafish larvae with indole increases intestinal motility (FIGS. 15A-D). This vagal sensory neuron activation induced by enteric indole was abrogated in zebrafish larvae lacking EECs (FIGS. 13K-O, FIGS. 15E-F). To test whether microbial Tryptophan metabolites induced Trpa1+ EEC signaling is conserved in mammalian models, amperometry was performed on fresh tissue sections from human and mouse small intestine to measure the impact of acute indole exposure on 5-HT secretion. Indole was able to significantly induce 5-HT secretion from both human and mouse small intestine, and this effect was blocked by the Trpa1 inhibitor HC030031 (FIGS. 13P-R). These data support the model and further suggest that these microbial tryptophan catabolites may modulate intestinal motility and gut-brain communication in humans.

Discussion

Microbially Derived Tryptophan Catabolites Interact with the Host Through Trpa1

Trpa1 is a primary nociceptor involved in pain sensation and neuroinflammation. Trpa1 can be activated by several environmental chemical irritants and inflammatory mediators (Bautista et al., 2006), however, it was not known if and how Trpa1 might be activated by microbes. Tryptophan is an essential amino acid that is released in the intestinal lumen by dietary protein digestion or microbial synthesis. Gut microbes can catabolize tryptophan to produce a variety of metabolites, among which indole was the first discovered and often the most abundant (Smith, 1897). These tryptophan-derived metabolites secreted by gut bacteria can act as interspecies and interkingdom signaling molecules. Some microbially-derived tryptophan catabolites including indole and IAld may regulate host immune homeostasis and intestinal barrier function through ligand binding to the transcription factors, Ahr and Pxr (Venkatesh et al., 2014, Zelante et al., 2013). Another microbial tryptophan catabolite, tryptamine, activates epithelial 5-$HT_4$R and increases anion-dependent fluid secretion in the proximal mouse colon (Bhattarai et al., 2018). Though several tryptophan metabolites including IAld can act as Ahr agonists (Zelante et al., 2013), conflicting effects of indole on AhR activation have been reported (Heath-Pagliuso et al., 1998, Hubbard et al., 2015, Jin et al., 2014). The results presented herein indicate that *E. tarda* or Trpa1+EEC-induced intestinal motility is not mediated via AhR (FIGS. 15G-L). Whether other host receptors can recognize microbially derived tryptophan catabolites was previously unknown. Here, evidence that bacteria-derived tryptophan catabolites activate Trpa1 in zebrafish, human, and mouse is presented. The findings presented herein point to an ancient role for TRP channels in microbial metabolite sensing. These results indicate that intestinal colonization by bacteria that produce high levels of tryptophan catabolites (e.g., *E. tarda*) leads to detection of those catabolites by Trpa1+EECs leading to purging of those bacteria by increased intestinal motility. These discoveries were made possible because *E. tarda*, but none of the other tested zebrafish commensals, exhibited high capacity to produce and secrete tryptophan catabolites in zebrafish water conditions. Since no overt pathogenesis was detected in *E. tarda*-treated zebrafish under those experimental conditions, and since many of the *E. tarda* induced responses were recapitulated by indole or IAld alone, it is believed that EEC Trpa1 activation and its downstream consequences reported herein are separable from *E. tarda* induced pathogenesis and have broader relevance for host-microbial relationships in the gut.

Trpa1+EECs are abundant in the small intestine but not in the colon of human and rodents (Yang et al., 2019, Nozawa et al., 2009). The data presented herein demonstrate that microbially derived tryptophan metabolites are restricted to the colon and largely absent in small intestine under normal physiological conditions (FIGS. 15G-H), suggesting that Trpa1+EECs may not play a major role to regulate intestinal motility under normal physiological conditions. Instead, Trpa1+EECs may act as a host protective mechanism that detects tryptophan catabolites accumulating due to aberrant overgrowth of small intestinal microbiota or invasion of specific microbes like *E. tarda* that precociously produce those catabolites, and in response increases intestinal motility to purge that particular community. On one hand, loss or impairment of that protective mechanism may result in overgrowth or dysbiosis of small intestinal microbial communities or an increased risk of enteric infection. On the other hand, excessive or chronic activation of those Trpa1+ EECs may result in pathophysiological changes. One such scenario may be small intestinal bacteria overgrowth (SIBO), which is prevalent in patients suffering from diarrhea-dominant irritable bowel syndrome (IBS) (Ghoshal et al., 2017). IBS is a complicated disease that display comorbidities of both impairment of GI motility and CNS symptoms. The cause of SIBO in IBS is incompletely understood although several studies demonstrated that some of the indole producing bacteria like *Escherichia coli* exhibit high abundance in the small intestine of SIBO associated IBS patients (Ghoshal et al., 2014, Leite et al., 2020, Avelar Rodriguez et al., 2019). The findings presented herein suggest that SIBO leads to an increase of microbial tryptophan metabolite production in the small intestine, which then activates Trpa1+EECs to increases intestinal motility and modulate CNS activity through the vagal nerve, resulting in the complex comorbidities of intestinal and psychiatric disorders in IBS.

Gut Microbiota-EEC-ENS Communication

Nerve fibers do not penetrate the gut epithelium therefore, sensation is believed to be a transepithelial phenomenon as the host senses gut contents through the relay of information from EECs to the ENS (Gershon, 2004). Using an in vitro preparation of mucosa-submucosa, mechanical or electrical stimulation of mucosa was shown to activate submucosal neuronal ganglia, an effect blocked by a 5-HT1R antagonist (Pan and Gershon, 2000). Consistent with these previous findings, zebrafish data suggest a model that 5-HT released from Trpa1+EECs stimulates intrinsic primary afferent neurons (IPANs) which then activate secondary neurons to promote intestinal motility through the local enteric EEC-ENS circuitry. 90% of 5-HT in the intestine is produced by EC cells, and therefore, EC cell 5-HT secretion was thought to be important in regulating intestinal motility (Gershon, 2013). This hypothesis, however, was challenged by recent findings that depletion of EC 5-HT production in $Tph1^{-/-}$ mice had only minor effects on gastric emptying, intestinal transit, and colonic motility (Li et al., 2011). Therefore, the physiological role of EC 5-HT production and secretion remains unclear. The data presented herein suggests that EEC 5-HT production may be necessary for intestinal motility changes in response to environmental chemical or microbial stimuli, but not for intestinal motility under normal physiological conditions. Mice raised germ-free displayed lower 5-HT content in the colon, however no significant difference of 5-HT production was observed in the small intestine compared to colonized mice (Yano et al., 2015). Whether gut microbiota regulate small intestinal 5-HT secretion and signaling remains unknown. The data shown herein suggest a model in which specific microbial communities or constituent species stimulate 5-HT secretion from Trpa1+EECs to modulate small intestinal motility by producing tryptophan catabolites. This may provide a new mechanism by which gut microbiota can regulate 5-HT signaling in the small intestine. Indole, IAld and other tryptophan catabolites are produced by a wide range of gut bacteria, so results herein should be applicable to commensal and pathogenic bacteria and their host interactions.

Gut Microbiota-EEC-CNS Communication

The vagus nerve is the primary sensory pathway by which visceral information is transmitted to the CNS. Recent evidence suggests that the vagus nerve may play a role in communicating gut microbial information to the brain (Fulling et al., 2019, Breit et al., 2018, Bonaz et al., 2018). For example, the beneficial effects of *Bifidobacterium longum* and *Lactobacillus rhamnosus* in neurogenesis and behavior were abolished following vagotomy (Bercik et al., 2011, Bravo et al., 2011). However, direct evidence for whether and how vagal sensory neurons perceive and respond to gut bacteria has been lacking. The results herein demonstrate that bacterial tryptophan catabolites activate vagal sensory ganglia through EEC Trpa1 signaling. Previous findings have shown that EC cells transmit microbial metabolite and chemical irritant stimuli to pelvic fibers from the spinal cord dorsal root ganglion (Bellono et al., 2017). Findings here demonstrate that, in addition to spinal sensory nerves, EEC-vagal signaling is an important pathway for transmitting specific gut microbial signals to the CNS. The vagal ganglia project directly onto the hindbrain, and that vagal-hindbrain pathway has key roles in appetite and metabolic regulation (Grill and Hayes, 2009, Han et al., 2018, Travagli et al., 2006, Berthoud et al., 2006). The present findings raise the possibility that certain tryptophan catabolites, including indole, may directly impact these processes as well as emotional behavior and cognitive function (Jaglin et al., 2018). If so, this pathway could be manipulated to treat gut microbiota-associated neurological disorders.

Methods

Experimental Model and Subject Details

Zebrafish Strains and Husbandry

All zebrafish experiments conformed to the US Public Health Service Policy on Humane Care and Use of Laboratory Animals, using protocol numbers A115-16-05 and A096-19-04 approved by the Institutional Animal Care and Use Committee of Duke University. For experiments involving conventionally raised zebrafish larvae, adults were bred naturally in system water and fertilized eggs were transferred to 100 mm petri dishes containing ~25 mL of egg water at approximately 6 hours post-fertilization. The resulting larvae were raised under a 14 h light/10 h dark cycle in an air incubator at 28 °C at a density of 2 larvae/mL water. All the experiments performed in this study ended at 6 dpf unless specifically indicated. The strains used in this study are listed in Table 2. All lines were maintained on a mixed Ekkwill (EKW) background.

Bacterial Strains and Growing Conditions

All bacterial strains in this study were cultured at 30 °C in Trypticase soy broth (TSB) or Gnotobiotic zebrafish medium (GZM) (Pham et al., 2008). Tryptic Soy Agar (TSA) plate was used for streaking bacterial from glycerol stock or performing colony forming unit (CFU) experiments. The antibiotic carbenicillin was used to select *E. tarda* LSE that express mCherry at the working concentration of 100 μg/mL.

Method Details

Generating Transgenic Zebrafish

The Gateway Tol2 cloning approach was used to generate the neurod1:CAMPARI and neurod1:cre plasmids (Kawakami, 2007, Kwan et al., 2007). The 5 kb pDONR-neurod1 P5E promoter was previously reported (McGraw et al., 2012). The pME-cre plasmid was reported previously (Cronan et al., 2016). The pcDNA3-CAMPARI plasmid was reported previously (Fosque et al., 2015) and obtained from Addgene. The CaMPARI gene was cloned into pDONR-221 plasmid using BP clonase (Invitrogen, 11789-020) to generate PME-CAMPARI. pDONR-neurod1 P5E and PME-CAMPARI were cloned into pDestTol2pA2 using LR Clonase (ThermoFisher, 11791). Similarly, pDONR-neurod1 P5E and pME-cre were cloned into pDestTol2CG2 containing a cmlc2:EGFP marker. The final plasmid was sequenced and injected into the wild-type EKW zebrafish strain and the F2 generation of alleles Tg(neurod1:CaMPARI)$^{rdu78}$ and Tg(neurod1:cre; cmlcl2:EGFP)$^{rdu79}$ were used for this study.

To make transgenic lines, that permit specific EEC ablation, Tg(neurod1:cre) and TgBAC(gata5:loxp-mCherry-stop-loxp-DTA) new transgenic system were used. This system consists of two new transgene alleles-one expressing Cre recombinase from the neurod1 promoter (in EECs, CNS, and islets) and a second expressing the diphtheria toxin (DTA) in gata5+ cells (in EECs, other IECs, heart, and perhaps other cell types) only in the presence of Cre (FIG. 5F). As the only cells known to co-express neurod1 and gata5 in the zebrafish larvae, EECs are ablated whereas non-EEC cell populations, including islets and the CNS, remain unaffected (FIG. 5G). A small percentage of EECs remained in the distal intestine presumably due to the low level of gata5 expression in that region (FIG. 7C). The method for generating Tg(neurod1:cre) was described above. To generate the TgBAC(gata5:loxp-mCherry-stop-loxp-DTA) transgenic line, the translational start codon of gata5 in the BAC clone DKEYP-73A2 was replaced with the loxP-mCherry-STOP-loxP-DTA (RSD) cassette by Red/ET recombineering technology (GeneBridges). For recombination with arms flanking the RSD cassette, the 5' homologous arm used was a 716 bp fragment upstream of the start codon and the 3' homologous arm was a 517 bp downstream fragment. The vector-derived loxP site was replaced with an I-SceI site using the same technology. The final BAC was purified using the Qiagen Midipre kit, and co-injected with I-SceI into one-cell stage zebrafish embryos. The full name of this transgenic line is Tg(gata5:loxP-mCherry-STOP-loxP-DTA)$^{pd315}$.

Tg(tph1b:mCherry-NTR)$^{pd275}$ zebrafish were generated using I-SceI transgenesis in an Ekkwill (EK) background. Golden Gate Cloning with BsaI-HF restriction enzyme (NEB) and T4 DNA ligase (NEB) was used to generate the tph1b:mCherry-NTR plasmid by cloning the 5 kb tph1b promoter sequence (tph1bP GG F: GGTCTC-GATCGGtctaaggtgaatctgtcacattc (SEQ ID NO: 23); tph1bP GG R: GGTCTCGGCTACggatggatgctcttgttttatag (SEQ ID NO: 24)), mCherry (mC GG F: GGTCTCGTAGCC gccgc-caccatggtgag (SEQ ID NO: 25); mC GG2 R: GGTCTCGGTACCcttgtacagctegtccatgccgcc (SEQ ID NO: 26)), a P2A polycistronic sequence and triple mutant variant nitroreductase (Mathias et al., 2014) (mutNTR GG F:

GGTCTCGGTACCtacttgtacaagggaagcggagc (SEQ ID NO: 27); mutNTR GG2 R: GGTCTCCCATGC caggateggtcgtgctcga (SEQ ID NO: 28)), into a pENT7 vector backbone with a poly-A tail and I-SceI sites (pENT7 mCN GG F: GGTCTCGCATGGacacctccccctgaacctg (SEQ ID NO: 29); pENT7 mCN GG R: GGTCTCCCGATC gtcaaaggtttggggtccgc (SEQ ID NO: 30)). 500 pL of 25 ng/μL plasmid, 333 U/mL I-SceI (NEB), 1×I-SceI buffer, 0.05% Phenol Red (Sigma-Aldrich) solution was injected into EK 1-cell zebrafish embryos. F0 founders were discovered by screening for fluorescence in outcrossed F1 embryos.

RNA Sequencing and Bioinformatic Analysis

To isolate zebrafish EECs and other IECs, two transgenic zebrafish lines were crossed, one that specifically expresses enhanced green fluorescent protein (EGFP) in all intestinal epithelial cells (TgBAC(cldn15la:EGFP)) (Alvers et al., 2014) and a second that expresses red fluorescent protein (RFP) in EECs, pancreatic islets, and the central nervous system (CNS) (Tg(neurod1:TagRFP)) (McGraw et al., 2012). The FACS-isolated EECs were identified by cldn15la:EGFP+; neurod1:TagRFP+; and the other IECs were identified by cldn15la:EGFP+; neurod1:TagRFP−. Conventionalized (CV) and germ-free (GF) TgBAC (cldn15la:EGFP); Tg(neurod1:TagRFP) ZM000 fed zebrafish larvae were derived and reared using a published protocol (Pham et al., 2008) for Flow Activated Cell Sorting (FACS) to isolate zebrafish EECs and other IECs. The protocol for FACS was adopted from a previous publication (Espenschied et al., 2019). Replicate pools of 50-100 double transgenic TgBAC(cldn15la:EGFP); Tg(neurod1:TagRFP) zebrafish larvae were euthanized with Tricaine and washed with deyolking buffer (55 mM NaCl, 1.8 mM KCl and 1.25 mM $NaHCO_3$) before they were transferred to dissociation buffer [HBSS supplemented with 5% heat-inactivated fetal bovine serum (HI-FBS, Sigma, F2442) and 10 mM HEPES (Gibco, 15630-080)]. Larvae were dissociated using a combination of enzymatic disruption using Liberase (Roche, 05 401 119 001, 5 μg/mL final), DNaseI (Sigma, D4513, 2 μg/mL final), Hyaluronidase (Sigma, H3506, 6 U/mL final) and Collagenase XI (Sigma, C7657, 12.5 U/mL final) and mechanical disruption using a gentleMACS dissociator (Miltenyi Biotec, 130-093-235). 400 μL of ice-cold 120 mM EDTA (in 1×PBS) was added to each sample at the end of the dissociation process to stop the enzymatic digestion. Following addition of 10 mL Buffer 2 [HBSS supplemented with 5% HI-FBS, 10 mM HEPES and 2 mM EDTA], samples were filtered through 30 μm cell strainers (Miltenyi Biotec, 130-098-458). Samples were then centrifuged at 1800 ref for 15 minutes at room temperature. The supernatant was decanted, and cell pellets were resuspended in 500 μL Buffer 2. FACS was performed with a MoFlo XDP cell sorter (Beckman Coulter) at the Duke Cancer Institute Flow Cytometry Shared Resource. Single-color control samples were used for compensation and gating. Viable EECs or IECs were identified as 7-AAD negative.

Samples from three independent experimental replicates were performed. 250-580 EECs (n=3 for each CV and GF group) and 100 IECs (n=3 for each CV and GF group) from each experiment were used for library generation and RNA sequencing. Total RNA was extracted from cell pellets using the Argencourt RNAdvance Cell V2 kit (Beckman) following the manufacturer's instructions. RNA amplification prior to library preparation had to be performed. The Clontech SMART-Seq v4 Ultra Low Input RNA Kit (Takara) was used to generate full-length cDNA. mRNA transcripts were converted into cDNA through Clontech's oligo (dT)-priming method. Full length cDNA was then converted into an Illumina sequencing library using the Kapa Hyper Prep kit (Roche). In brief, cDNA was sheared using a Covaris instrument to produce fragments of about 300 bp in length. Illumina sequencing adapters were then ligated to both ends of the 300 bp fragments prior to final library amplification. Each library was uniquely indexed allowing for multiple samples to be pooled and sequenced on two lanes of an Illumina HiSeq 4000 flow cell. Each HiSeq 4000 lane could generate >330M 50 bp single end reads per lane. This pooling strategy generated enough sequencing depth (~55M reads per sample) for estimating differential expression. Sample preparation and sequencing was performed at the GCB Sequencing and Genomic Technologies Shared Resource.

Zebrafish RNA-seq reads were mapped to the danRer10 genome using HISAT2 (Galaxy Version 2.0.5.1) using default settings. Normalized counts and pairwise differentiation analysis were carried out via DESeq2 (Love et al., 2014) with the web based-galaxy platform: usegalaxy.org. For the purpose of this study, only the CV EEC (n=3) and CV IEC (n=3) comparison and analysis are shown. The default significance threshold of FDR <5% was used for comparison. Hierarchical clustering of replicates and a gene expression heat map of RNA-seq data were generated using the online expression heatmap tool: heatmapper.ca/expression. The human and mouse RNA-seq raw counts data were obtained from the NCBI GEO repository: human, GSE114853; mouse, GSE114913 (Roberts et al., 2019). Pairwise differentiation analysis of human jejunum CHGA+ (n=11) and CHGA-(n=11) and mouse duodenum Neurod1+ (n=3) and Neurod1-(n=3) was performed using DESeq2. The mouse and zebrafish ortholog Gene ID conversion was downloaded from Ensemble. The genes that were significantly enriched ($P_{FDR}$<0.05) in the human and mouse EEC data sets were used to query the zebrafish EEC RNA seq dataset and data were plotted using Graphpad Prism7. RNA-seq data generated in this study can be accessed under Gene Expression Omnibus accession GSE151711.

Recording In Vivo EEC Activity

CAMPARI undergoes permanent green-to-red photoconversion (PC) under 405 nm light when calcium is present. This permanent conversion records the calcium activity for all areas illuminated by PC-light. Red fluorescence intensity correlates with calcium activity during photoconversion (Fosque et al., 2015). In the Tg(neurod1:CaMPARI) zebrafish line, the CaMPARI (calcium-modulated photoactivatable ratiometric integrator) transgene is expressed under control of the −5 kb promoter cloned from the zebrafish neurod1 locus. CAMPARI mRNA is transcribed and the CaMPARI protein is expressed in cells that are able to activate the neurod1 promoter. There are multiple cell types in the zebrafish body that are sufficient to activate the neurod1 promoter, including all EECs in the intestine (Ye et al., 2019). CaMPARI protein is a calcium indicator protein that binds calcium and converts from green fluorescence to red fluorescence in the presence of UV light. This protein is engineered and described in detail in a previous publication (Fosque et al., 2015). This transgenic model was used to measure the level of intracellular calcium in EECs. Similar to neurons, it is well known that when extracellular stimulants act on various receptors on EECs, this leads to an increase of intracellular calcium either due to calcium influx through calcium channels in the plasma membrane or release of calcium stored in the ER. Through either of these pathways, increased intracellular calcium then directly triggers EECs to release hormone/neurotransmitter vesicles. To record in vivo EEC activity using the CaMPARI platform, conventionally raised Tg(neurod1:CaMPARI) zebrafish larvae were sorted at 3 dpf and maintained in Gnotobiotic Zebrafish Media (GZM) (Pham et al., 2008) with 1 larvae/mL density. At 6 dpf, for each experimental group, ~20 larvae were transferred into 50 mL conical tubes in 2 mL GZM medium. The larvae were adjusted to the new environment for 30 mins before stimuli were added to each conical tube. For nutrient stimulation, since linoleate, oleate and laurate are not soluble in water, a bovine serum albumin (BSA) conjugated fatty acid solution was generated as described previously (Ye et al., 2019). 2 mL linoleate, oleate, laurate, butyrate or glucose was added to the testing tube containing ~20 zebrafish larvae in 3 mL GZM. The final stimulant concentrations were: linoleate (1.66 mM), oleate (1.66 mM), laurate (1.66 mM), butyrate (2 mM) and glucose (500 mM). Zebrafish larvae were stimulated for 2 mins (fatty acids) or 5 mins (glucose) before the UV pulse. For bacterial stimulation, single colonies of the different bacterial strains were cultured aerobically in tryptic soy broth (TSB) at 30 °C overnight (rotating 50-60 rpm, Thermo Fisher Tissue Culture Rotator CEL-GRO #1640Q) (see strains listed in Table 2). O/N TSB cultured bacteria were harvested, washed with GZM and resuspended in 2 mL GZM. 2 mL bacteria were then added to a test tube containing ~20 zebrafish larvae in 3 mL GZM. The final concentration of the bacterial is ~$10^8$ CFU/ml. Zebrafish were then stimulated for 20 mins before treated with a UV pulse. A customized LED light source (400 nm-405 nm, Hongke Lighting CO. LTD) was used to deliver a UV light pulse (100 W power, DC32-34 V and 3500 mA) for 30 seconds. Following the UV pulse, zebrafish larvae were transferred to 6-well plates. To block spontaneous intestinal motility and facilitate in vivo imaging, zebrafish larvae were incubated in 20 μM 4-DAMP (mAChR blocker), 10 μM atropine (mAChR blocker) and 20 μM clozapine (5-HTR blocker) for 30 mins. Zebrafish larvae were then anesthetized with Tricaine (1.64 mg/ml) and mounted in 1% low melting agarose and imaged using a 780 Zeiss upright confocal microscope in the Duke Light Microscope Core Facility. Z-stack confocal images were taken of the mid-intestinal region in individual zebrafish. The laser intensity and gain were set to be consistent across different experimental groups. The resulting images were then processed and analyzed using FIJI software (Schindelin et al., 2012). To quantify the number of activated EECs, the color threshold was set for the CAMPARI red channel. EECs surpassing the color threshold were counted as activated EECs. The CaMPARI green channel was used to quantify the total number of EECs in each sample. The ratio of activated EECs to the total EEC number was calculated as the percentage of activated EECs. As reported in FIGS. 2A-F, in Tg(neurod1:CaMPARI) zebrafish model, in addition to EECs, CAMPARI is also expressed in other neurod1+ cells including CNS and pancreatic islet. Therefore, the Tg(neurod1:CaMPARI) model can also be used to measure the activity of the CNS and pancreatic islet. However, the method described above permitted specific analysis of EEC signal through restricting image inquiry in the middle intestine, a region in which only EECs express CAMPARI.

To record in vivo EEC activity using the Tg(neurod1:Gcamp6f) system, a published protocol with slight modification (Ye et al., 2019) was used. In brief, unanesthetized zebrafish larvae were gently mounted in 3% methylcellulose. Excess water was removed and zebrafish larvae were gently positioned with right side up. Zebrafish were then moved onto an upright Leica M205 FA fluorescence stereomicroscope equipped with a Leica DFC 365FX camera. The zebrafish larvae were allowed to recover for 2 mins before 100 μL of test agent was pipetted directly in front of the mouth region. Images were then recorded every 10 seconds. The data shown in FIGS. 2O-R, depicting the EEC responses to *E. tarda* stimulation, were obtained by mounting unanesthetized zebrafish larvae in 1% low melting agarose. A window (5×5 mm) was cut to expose the head region of the zebrafish. 10 μL of *E. tarda* culture [~$10^9$ Colony Forming Unit (CFU)] were delivered at the zebrafish mouth area. Images were recorded every 10 secs for 20 mins. Image processing and analysis were performed using FIJI software. Time-lapse fluorescence images were first aligned to correct for experimental drift using the plugin "align slices in stack." Normalized correlation coefficient matching and bilinear interpolation methods for subpixel translation were used for aligning slices (Tseng et al., 2012). The plugin "rolling ball background subtraction" with the rolling ball radius=10 pixels was used to remove the large spatial variation of background intensities. The Gcamp6f fluorescence intensity in the intestinal region was then calculated for each time point. The ratio of maximum fluorescence (Fmax) and the initial fluorescence (F0) was used to measure EEC calcium responses.

Immunofluorescence Staining and Imaging

Whole mount immunofluorescence staining was performed as previously described (Ye et al., 2019). In brief, ice cold 2.5% formalin was used to fix zebrafish larvae overnight at 4 °C. The samples were then washed with PT solution (PBS+0.75% Triton-100). The skin and remaining yolk were then removed using forceps under a dissecting microscope. The deyolked samples were then permeabilized with methanol for more than 2 hrs at −20 °C. Samples were then blocked with 4% BSA at room temperature for more than 1 hr. The primary antibody was diluted in PT solution and incubated at 4 °C for more than 24 hrs. Following primary antibody incubation, the samples were washed with PT solution and incubated overnight with secondary antibody with Hoechst 33342 for DNA staining. Imaging was performed with Zeiss 780 inverted confocal and Zeiss 710 inverted confocal microscopes with 40× oil lens. The secondary antibodies in this study were from Alexa Fluor Invitrogen were used at a dilution of 1:250.

To quantify vagal activity by pERK staining, published protocol with slight modification (Randlett et al., 2015) was used. Zebrafish larvae were quickly collected by funneling through a 0.75 mm cell strainer and dropped into a 5 mL petri dish containing ice cold fix buffer (2.5% formalin+0.25% Triton 100). Larvae were fixed overnight at 4 °C, then washed 3 times in PT (PBS+0.3% Triton 100), treated with 150 mM Tris-HCl (PH=9) for 15 mins at 70 °C, washed with PT and digested with 0.05% trypsin-EDTA on ice for 45 mins. Following digestion, samples were then washed with PT and transferred into block solution [PT+1% bovine serum albumin (BSA, Fisher)+2% normal goat serum (NGS, Sigma)+1% dimethyl sulfoxide (DMSO)]. The primary antibodies [pERK (Cell signaling); tERK (Cell signaling); GFP (Aves Lab)] were diluted in block solution (1:150 for pERK; 1:150 for tERK and 1:500 for GFP) and samples were incubated in 100 μl of primary antibody overnight at 4 °C. Following primary antibody incubation, samples were then washed with PT and incubated with secondary antibody overnight at 4 °C. Samples were then washed with PBS, mounted in 1% LMA and imaged using a Zeiss 780 upright confocal microscope.

Zebrafish *E. tarda* Colonization

For *E. tarda* colonization experiments, fertilized zebrafish eggs were collected, sorted and transferred into a cell culture flask containing 80 mL GZM at 0 dpf. At 3 dpf, dead embryos and 60 mL GZM were removed and replaced with 50 mL fresh GZM in each flask. To facilitate consistent commensal gut bacterial colonization, an additional 10 mL of filtered system water (5 μm filter, SLSV025LS, Millipore) were added to each flask. Overnight *E. tarda* mCherry culture was harvested, washed three times with GZM. 150 μL of GZM-washed *E. tarda* mCherry culture were inoculated into each flask. The *E. tarda* concentration is ~$10^6$ CFU/ml. Daily water changes (60 ml) was performed and 200 μL autoclaved solution of ZM000 food (ZM Ltd.) was added from 3 dpf to 6 dpf as previously described (Pham et al., 2008). At 6 dpf, zebrafish larvae were subjected to fluorescence imaging analysis or CFU quantification. For fluorescence imaging analysis, zebrafish larvae were anesthetized with Tricaine (1.64 mg/ml), mounted in 3% methylcellulose and imaged with a Leica M205 FA upright fluorescence stereomicroscope equipped with a Leica DFC 365FX camera. For CFU quantification, digestive tracts were dissected and transferred into 1 mL sterile PBS which was then mechanically disassociated using a Tissue-Tearor (BioSpec Products, 985370). 100 μL of serially diluted solution was then spread on a Tryptic soy agar (TSA) plate with Carbenicillin (100 μg/ml) and cultured overnight at 30 °C under aerobic conditions. The mCherry+ colonies were quantified from each plate and *E. tarda* colony forming units (CFUs) per fish were calculated.

Zebrafish Microgavage and Chemical Treatment

For delivering bacterial or chemicals specifically to the intestine, the established microgavage technique (Cocchiaro and Rawls, 2013) was adopted. Zebrafish were anesthetized with 1 mg/mL α-Bungarotoxin (α-BTX) and the gavage procedure was performed as previously described using microinjection station (Cocchiaro and Rawls, 2013). For bacteria gavage experiments, 1 ml of overnight bacterial culture was harvested, pelleted, washed with PBS and resuspended in 100 ul PBS. ~8nl was then delivered into the zebrafish intestine using microgavage. The gavaged zebrafish was then transferred into egg water and mounted in 1% LMA for imaging. For chemical gavage experiments, ~8nl of AITC (100 mM), indole (1 mM) and IAld (1 mM) was gavaged into the intestine.

For Trpa1 inhibition, Trpa1 antagonist HC030031 (280 μM) was treated 2 hours before and during the 30 mins of *E. tarda* stimulation. For AhR inhibition, two AhR inhibitors, CH030031 and folic acid, were selected based on previous publications (Puyskens et al., 2020, Kim et al., 2020). CH030031 is a well-established specific AhR inhibitor (Choi et al., 2012). Whereas folic acid is shown to act as a competitive AhR antagonist at the concentration as low as 10 ng/ml (Kim et al., 2020). For the *E. tarda* treatment experiment, DMSO, CH030031 (1 μM) or folic acid (10 μM) was added into zebrafish water at 3 dpf zebrafish at the same time as *E. tarda* administration. The AhR inhibitors were replenished during daily water changes, and zebrafish were analyzed at 6 dpf. For the Optovin-UV experiment, overnight Optovin treated zebrafish were treated for 2 hours with DMSO, CH030031 (10 μM) or folic acid (10 μM). As demonstrated by previous study, 2-hour 10 μM and 3-day 0.5 μM CH030031 treatment is sufficient to inhibit larvae zebrafish AhR signaling (Puyskens et al., 2020, Sun et al., 2019b, Yue et al., 2017). The concentration of FA was chosen based on zebrafish tolerance and a previous study shown the treatment of early zebrafish embryos with 0.05 μM FA inhibits AhR signaling (Yue et al., 2017).

Optic EEC Activation

For EEC Trpa1 activation using the Optovin platform, zebrafish larvae were treated with 10 μM Optovin overnight. Following Optovin treatment, unanesthetized zebrafish were mounted in 1% LMA and imaged under a 780 upright Zeiss confocal microscope using 20× water objective lenses. For all the experiments, the mid-intestine region was imaged (FIG. 10D). The intestinal epithelium was selected as the region of interest (ROI) (FIG. 10A). Serial images were obtained at 1 s/frame. A 405 nm pulse of light was applied to the ROI at 1 pulse/10s. For some experiments (FIGS. 7D-F, FIGS. 10B-G), the images were obtained at 10s/frame. When measuring Optovin effects on intestinal motility in ret−/−, sox10−/− or tph1b−/− zebrafish larvae, embryos were collected from heterozygous zebrafish. ret−/− zebrafish were identified by lack of ENS and deflated swim bladder (Knight et al., 2011), sox10−/− zebrafish were identified by lack of pigment (Rolig et al., 2017), and tph1b−/− zebrafish were identified by PCR-based genotyping (Tornini et al., 2017).

Photoactivation of channelrhodopsin (ChR2) in EECs was performed in Tg(neurod1:Gal4, cmlc2; EGFP); Tg(UAS:ChR2-mCherry) transgenic zebrafish. In this model, ChR2 expression in EECs is mosaic. At 6 dpf, unanesthetized zebrafish larvae were mounted in 1% LMA. Photoactivation and imaging were performed with a Zeiss 780 upright confocal using 20× water objective lenses. Individual ChR2+ EECs were selected as ROI (FIGS. 10H, I). Serial images were obtained at 1 s/frame. The 488 nm and 458 nm pulses were applied to the selected ROI at 1 pulse/s. For selectively activating trpa1b+ or trpa1b− ChR2 expressing EECs, Tg(neurod1:Gal4, cmlc2; EGFP); Tg(UAS:ChR2-mCherry) was crossed with TgBAC(trpa1b:EGFP). In each zebrafish, either Trpa1+ChR2+ EEC or Trpa1-ChR+ EEC was selected to activate and examine the motility pre and post activation. Each dot in updated FIG. 7L and FIG. 5H represent data from individual zebrafish. A snapshot of the intestinal area was obtained to determine the trpa1b+ ChR2+ and trpa1b− ChR2+ EECs (FIGS. 10H, I) and light pulses were applied to the selected EECs as indicated above. Due to the mosaic expression of ChR2 in the EECs in the Gal4-UAS transgenic system, the ChR2+ EECs in both proximal and middle intestinal regions are selected.

To determine whether Optovin-UV or ChR2 was sufficient to activate EECs, Tg(neurod1:Gcamp6f) zebrafish were used. To facilitate EEC calcium imaging under the confocal microscope, zebrafish larvae were incubated in 20 μM 4-DAMP, 10 μM atropine and 20 μM clozapine for 30 mins before mounting in 1% LMA to reduce spontaneous motility. The Gcamp6f signal was recorded with 488 nm laser intensity less than 0.5. The zebrafish intestinal motility is quantified through recorded image series of zebrafish intestine using the method similar as previously described (Ganz et al., 2018). Intestinal u velocity and v velocity were used to estimate intestinal motility in zebrafish as previously described using the PIV-Lab MATLAB app (Ganz et al., 2018). A positive value of the μ velocity indicates an anterograde intestinal movement and a negative value of the μ velocity indicates a retrograde intestinal movement. The time-course u velocity number is plotted as heatmaps. When calculating the mean velocity, only the mean velocity magnitude was calculated, which therefore doesn't account for the movement direction. The MTrackJ FIJI plugin was used to quantify the mean velocity magnitude (Meijering et al., 2012).

To assess whether Trpa1$^+$EEC activation induced intestinal motility change is due to the indirect communication through vagal afferent and efferent system, zebrafish CNS with the intestine was anatomically disconnected by decapitating. Optovin-treated unanesthetized zebrafish were mounted and placed on the 780 Zeiss upright confocal station as described above. The zebrafish head was then removed with a razor blade. The same imaging and 405 nm activation of the mid-intestinal region was performed as described above.

Enteric Cholinergic Neuron and Vagal Ganglion Calcium Imaging

TgBAC(chata:Gal4); Tg(UAS:Gcamp6s); Tg(NBT:DsRed) or TgBAC(chata:Gal4); Tg(UAS:Gcamp6s); Tg(UAS:NTR-mCherry) zebrafish were used to record in vivo calcium activity in enteric cholinergic neurons. The NBT promoter labels all ENS neurons while the Chata promoter labels only cholinergic enteric neurons. DsRed or mCherry fluorescence was used as reference for cholinergic neuron Gcamp quantification. Zebrafish larvae were incubated in 20 μM 4-DAMP for 30 mins before mounting in 1% LMA to reduce spontaneous motility and facilitate in vivo imaging using a Zeiss 780 upright confocal microscope with 20× water lenses. Serial images were taken at 5 s/frame. To record cholinergic neuron calcium activation, zebrafish was pretreated with Optovin and 40 nm light was applied at the frequency of 1 pulse/5s to the intestinal epithelium ROI. The Gcamp6s to DsRed fluorescence in cholinergic neurons was calculated for recorded.

Tg(neurod1:Gcamp6f); Tg(neurod1:TagRFP) zebrafish were used to record vagal sensory ganglia calcium activity in vivo. Zebrafish were anesthetized with 1 mg/mL α-Bungarotoxin (α-BTX) and gavaged with chemical compounds or bacteria as described (Naumann et al., 2016). Zebrafish larvae were mounted in 1% LMA and imaged under a Zeiss 780 upright confocal microscope. Z-stack images of the entire vagal ganglia were collected as serial images at 10 mins/frame and processed in FIJI. Individual vagal sensory neurons were identified and the Gcamp6f to TagRFP fluorescence ratios of individual vagal sensory neurons were calculated.

Quantitative Real-time PCR

Quantitative real-time PCR was performed as described previously (Murdoch et al., 2019). In brief, 20 zebrafish larvae digestive tracts were dissected and pooled into 1 mL TRIzol (ThermoFisher, 15596026). mRNA was then isolated with isopropanol precipitation and washed with 70% ethanol. 500 ng mRNA was used for cDNA synthesis using the iScript kit (Bio-Rad, 1708891). Quantitative PCR was performed in triplicate 25 μL reactions using 2×SYBR Green SuperMix (PerfeCTa, Hi Rox, Quanta Biosciences, 95055) run on an ABI Step One Plus qPCR instrument using gene specific primers (Supplementary file 1). Data were analyzed with the ΔΔCt method. 18S was used as a housekeeping gene to normalize gene expression.

Mammalian TRPA1 Activity Analysis

HEK-293T cells were cultured in DMEM (Thermofisher Scientific, Waltham, MA) and supplemented with 10% fetal bovine serum (FBS) (Thermofisher Scientific), penicillin (100 units/mL) and streptomycin (0.1 mg/mL). Cells were plated on 100 mm tissue culture plates coated with poly-D-lysine (Sigma Aldrich, Saint Louis, MO) and grown to ~60% confluence. The cells were transiently transfected for 16-24 hours with either human or mouse orthologs of TRPA1 using Fugene 6 transfection reagents and Opti-MEM (Thermofisher Scientific) according to the manufacturer's protocol. Subsequently, cells were trypsinized, re-suspended and re-plated onto poly-D-lysine coated 96-well plates (Krystal black walled plates, Genesee Scientific) at $5\times10^5$ cells/mL (100 μL/well) and allowed to grow for another 16-20 hrs prior to the experiments. Cells were maintained as monolayers in a 5% $CO_2$ incubator at 37 °C.

Measurements of changes in intracellular $Ca^{2+}$ concentrations ($[Ca^{2+}]_i$) were performed as described previously (Caceres et al., 2017). In brief, cells in 96-well plates were loaded with Calcium 6, a no-wash fluorescent indicator, for 1.5 hrs (Molecular Devices, San Jose, CA) and then transferred to a FlexStation III benchtop scanning fluorometer chamber (Molecular Devices). Fluorescence measurements in the FlexStation were performed at 37 °C (Ex: 485 nm, Em: 525 nm at every 1.8 s). After recording baseline fluorescence, agonists (indole, IAld, cinnamaldehyde) were added and fluorescence was monitored for a total of 60 s. To determine the effects of TRPA1 inhibition on agonist response, TRPA1 transfected HEK-293 cells were pretreated with various concentrations of A967079 (Medchem101, Plymouth Meeting, PA), a specific antagonist of TRPA1, and then exposed to either 100 μM indole or IAld. The change in fluorescence was measured as Fmax-F0, where Fmax is the maximum fluorescence and F0 is the baseline fluorescence measured in each well. The EC50 and IC50 values and associated 95% confidence intervals for agonist (Indole and IAld) stimulation of $Ca^{2+}$ influx and A967079 inhibition of agonist-induced $Ca^{2+}$ influx, respectively, were determined by non-linear regression analysis with a 4-parameter logistic equation (Graphpad Prism, San Diego, CA). Indole and IAld concentration-response data was normalized to 1 mM cinnamaldehyde for EC50's calculations and A967079 concentration-response data was normalized to 100 μM indole or IAld for IC50's calculations.

HPLC-MS Analysis of Trp-Indole Derivatives

The chemical profiling of Trp-Indole derivatives was performed using 1 L culture of *E. tarda*. The strain was inoculated in 3 mL of TSB medium and cultivated for 1 day on a rotary shaker at 180 rpm at 30 °C under aerobic conditions. After 1 day, 1 mL of *E. tarda* liquid culture was inoculated in 1 L of TSB medium in a 4-L Pyrex flask. The *E. tarda* culture was incubated at 30 °C for 24 hr under aerobic conditions. For time-course screening, 10 mL from the *E. tarda* TSB culture was collected at 0, 6, 18, and 24 hours. Each 10 mL sample of *E. tarda* culture was extracted with 15 mL of ethyl acetate (EtOAc). The EtOAc layer was separated from the aqueous layer and residual water was removed by addition of anhydrous sodium sulfate. Each EtOAc fraction was dried under reduced pressure, then resuspended in 500 μL of 50% MeOH/50% $H_2O$ and 50 μL of each sample were analyzed using an Agilent Technologies 6130 quadrupole mass spectrometer coupled with an Agilent Technologies 1200-series HPLC (Agilent Technologies, Waldbron, Germany). The chemical screening was performed with a Kinetex® EVO C18 column (100×4.6 mm, 5 μm) using the gradient solvent system (10% ACN/90% $H_2O$ to 100% ACN over 20 min at a flow rate of 0.7 mL/min).

For HPLC-MS analysis of *E. tarda* in GZM medium, the remaining 1 L culture of *E. tarda* in TSB culture was centrifuged at 7,000 rpm for 30 min. Pellets were transferred to 1 L of GZM medium in a 4-L Pyrex flask and cultivated on a rotary shaker at 30 °C for 24 hr. For time-course screening, 10 mL from the *E. tarda* GZM culture was collected at 0, 1, 6, and 24 hours. Sample preparation and HPLC-MS analysis of *E. tarda* culture GZM medium were performed using same procedures as described above for TSB. Trp-Indole derivatives of *E. tarda* culture broths were identified by comparing the retention time and extracted ion chromatogram with authentic standards. Extracted ions were selected for Indole (m/z 117, Sigma-Aldrich), IAld (m/z 145, Sigma-Aldrich), IAAld (m/z 159, Ambeed), IEt (m/z 161, Sigma-Aldrich), IAM (m/z 174, Sigma-Aldrich), IAA (m/z 175, Sigma-Aldrich), and IpyA (m/z 203, Sigma-Aldrich).

For HPLC-MS analysis of Trp-indole derivatives from 15 different bacterial strains in TSB medium, each of the strains (*Acinetobacter* sp. ZOR0008, *Aeromonas veronii* ZOR0002, *Bacillus subtilis* 168, *Chryseobacterium* sp. ZOR0023, *Edwardsiella tarda* 15974, *Edwardsiella tarda* 23685, *Edwardsiella tarda* LSE40, *Edwardsiella tarda* FL6-60, *Enterobacter* sp. ZOR0014, *Escherichia coli* MG1655, *Exiguobacterium acetylicum* sp. ZWU0009, *Plesiomonas* sp. ZOR0011, *Pseudomonas aeruginosa* PAK, *Shewanella* sp. ZOR0012, and *Vibrio* sp. ZWU0020) were inoculated in 3 mL of TSB medium and cultivated for 1 day on a rotary shaker at 180 rpm at 30 °C under aerobic conditions. After 1 day, 1 mL of each liquid culture was inoculated in 100 mL of TSB medium in 500 mL Pyrex flasks and cultivated on a rotary shaker at 30 °C overnight. A 10 mL sample was taken from each culture and extracted and analyzed via HPLC-MS as explained above. CFU was calculated for each bacterial liquid culture and the HPLC-MS data was normalized to the CFU.

For HPLC-MS analysis of Trp-indole derivatives from 15 different bacterial strains in GZM medium, the remaining 100 mL culture of each strain was centrifuged at 4500 rpm for 20 min. Pellets were transferred to 100 mL of GZM medium in 500 mL Pyrex flasks and cultivated on a rotary shaker at 30 °C overnight. Sample preparation and HPLC-MS analysis of each GZM culture were performed using the same procedure as described above.

For HPLC-MS analysis of Trp-indole derivatives from murine small intestine and large intestine, three 10-week old female and three 10-week old male conventionally-reared specific pathogen-free C57BL/6J mice were ordered from Jackson Lab. The mice were not fast in advance and euthanized with 5% isoflurane. The ⅔-⅘ portion of the small intestinal region and the colon caudal to cecum was collected from each mouse and transferred to a 50 mL conical tube that was placed on dry-ice. 80% methanol was then added according to the tissue weight (50 μL/mg tissue). The intestine was then homogenized with a Tissue-Tearor (BioSpec Products, 985370). Following homogenizing, the tryptophan metabolites were extracted and analyzed with HPLC-MS as explained above. The relative metabolite abundance was normalized to tissue weight. These mouse experiments conformed to the US Public Health Service Policy on Humane Care and Use of Laboratory Animals, using protocol number A170-17-07 approved by the Institutional Animal Care and Use Committee of Duke University.

Measurement of Serotonin Release from Mouse and Human Small Intestine

These experiments using C57BL/6J mice were approved by the Flinders University Animal Welfare Committee (number 965-19) and human ileum tissue was collected from resected small and large intestine from patients that gave written informed consent under the approval of the Southern Adelaide Clinical Human Research Ethics Committee (number 50.07) as previous (Sun et al., 2019a). Mice were euthanized at 8 to 12 weeks by isoflurane overdose followed by cervical dislocation. The duodenum was removed and placed in Krebs solution oxygenated with 95% 02, 5% $CO_2$. A midline incision was made along the duodenum to create a flat sheet, the section was pinned with the mucosal side up in an organ bath lined with Sylgard and containing oxygenated Krebs solution. Serotonin release was measured using amperometry. A carbon-fibre electrode (5-μm diameter, ProCFE; Dagan Corporation, Minneapolis, MN), was lowered above the mucosa and 400 mV potential was applied to the electrode causing oxidation of serotonin (Zelkas et al., 2015). 10 mM Indole and/or 50 μM HC030031 were applied to tissue by constantly perfusing the bath. The change in amplitude due to serotonin oxidation was recorded using an EPC-10 amplifier and Pulse software (HEKA Electronic, Lambrecht/Pfalz, Germany), and samples at 10 kHz and low-pass filtered at 1 kHz. Data was assessed as peak current during each treatment. Data was analyzed comparing all groups using one-way ANOVA with Tukey's post-hoc test. For the mouse experiments, 6 independent experiments were performed in 6 mouse duodenal samples. For the human experiments, 4 independent experiments were performed in 3 human samples.

Statistical Analysis

The appropriate sample size for each experiment was suggested by preliminary experiments evaluating variance and effects. Using significance level of 0.05 and power of 90%, a biological replicate sample number 8 was suggested for EEC CAMPARI analysis. For each experiment, wildtype or indicated transgenic zebrafish embryos were randomly allocated to test groups prior to treatment. Individual data points, mean and standard deviation are plotted in each figure. The raw data points in each figure are represented as solid dots. Data were analyzed using GraphPad Prism 7 software. For experiments comparing just two differentially treated populations, a Student's t-test with equal variance assumptions was used. For experiments measuring a single variable with multiple treatment groups, a single factor ANOVA with post hoc means testing (Tukey) was utilized. Statistical evaluation for each figure was marked *P<0.05, P<0.01, *P<0.001, ****P<0.0001 or ns (no significant difference, P>0.05).

REFERENCES

ABAYNEH, T., COLQUHOUN, D. J. & SORUM, H. 2013. *Edwardsiella piscicida* sp. nov., a novel species pathogenic to fish. *J Appl Microbiol,* 114, 644-54.

ALVERS, A. L., RYAN, S., SCHERZ, P. J., HUISKEN, J. & BAGNAT, M. 2014. Single continuous lumen formation in the zebrafish gut is mediated by smoothened-dependent tissue remodeling. *Development,* 141, 1110-9.

AVELAR RODRIGUEZ, D., RYAN, P. M., TORO MONJARAZ, E. M., RAMIREZ MAYANS, J. A. & QUIGLEY, E. M. 2019. Small Intestinal Bacterial Overgrowth in Children: A State-Of-The-Art Review. *Front Pediatr,* 7, 363.

BAUTISTA, D. M., JORDT, S. E., NIKAI, T., TSURUDA, P. R., READ, A. J., POBLETE, J., YAMOAH, E. N., BASBAUM, A. I. & JULIUS, D. 2006. TRPA1 mediates the inflammatory actions of environmental irritants and proalgesic agents. *Cell,* 124, 1269-82.

BELLONO, N. W., BAYRER, J. R., LEITCH, D. B., CASTRO, J., ZHANG, C., O'DONNELL, T. A., BRIERLEY, S. M., INGRAHAM, H. A. & JULIUS, D. 2017. Enterochromaffin Cells Are Gut Chemosensors that Couple to Sensory Neural Pathways. *Cell,* 170, 185-198 e16.

BERCIK, P., PARK, A. J., SINCLAIR, D., KHOSHDEL, A., LU, J., HUANG, X., DENG, Y., BLENNERHASSETT, P. A., FAHNESTOCK, M., MOINE, D., BERGER, B., HUIZINGA, J. D., KUNZE, W., MCLEAN, P. G., BERGONZELLI, G. E., COLLINS, S. M. & VERDU, E. F. 2011. The anxiolytic effect of *Bifidobacterium longum* NCC3001 involves vagal pathways for gut-brain communication. *Neurogastroenterol Motil,* 23, 1132-9.

BERTHOUD, H. R., SUTTON, G. M., TOWNSEND, R. L., PATTERSON, L. M. & ZHENG, H. 2006. Brainstem mechanisms integrating gut-derived satiety signals and descending forebrain information in the control of meal size. *Physiol Behav,* 89, 517-24.

BHATTARAI, Y., WILLIAMS, B. B., BATTAGLIOLI, E. J., WHITAKER, W. R., TILL, L., GROVER, M., LINDEN, D. R., AKIBA, Y., KANDIMALLA, K. K., ZACHOS, N. C., KAUNITZ, J. D., SONNENBURG, J. L., FISCHBACH, M. A., FARRUGIA, G. & KASHYAP, P. C. 2018. Gut Microbiota-Produced Tryptamine Activates an Epithelial G-Protein-Coupled Receptor to Increase Colonic Secretion. *Cell Host Microbe,* 23, 775-785 e5.

BOHORQUEZ, D. V., SHAHID, R. A., ERDMANN, A., KREGER, A. M., WANG, Y., CALAKOS, N., WANG, F. & LIDDLE, R. A. 2015. Neuroepithelial circuit formed by innervation of sensory enteroendocrine cells. *J Clin Invest,* 125, 782-6.

BONAZ, B., BAZIN, T. & PELLISSIER, S. 2018. The Vagus Nerve at the Interface of the Microbiota-Gut-Brain Axis. *Front Neurosci,* 12, 49.

BONDURAND, N. & SHAM, M. H. 2013. The role of SOX10 during enteric nervous system development. *Dev Biol,* 382, 330-43.

BORNSTEIN, J. C. 2006. Intrinsic sensory neurons of mouse gut—toward a detailed knowledge of enteric neural circuitry across species. Focus on "characterization of myenteric sensory neurons in the mouse small intestine". *J Neurophysiol,* 96, 973-4.

BRAVO, J. A., FORSYTHE, P., CHEW, M. V., ESCARAVAGE, E., SAVIGNAC, H. M., DINAN, T. G., BIENENSTOCK, J. & CRYAN, J. F. 2011. Ingestion of *Lactobacillus* strain regulates emotional behavior and central GABA receptor expression in a mouse via the vagus nerve. *Proc Natl Acad Sci USA,* 108, 16050-5.

BREIT, S., KUPFERBERG, A., ROGLER, G. & HASLER, G. 2018. Vagus Nerve as Modulator of the Brain-Gut Axis in Psychiatric and Inflammatory Disorders. *Front Psychiatry,* 9, 44.

BROOKES, S. J., SPENCER, N. J., COSTA, M. & ZAGORODNYUK, V. P. 2013. Extrinsic primary afferent signalling in the gut. *Nat Rev Gastroenterol Hepatol,* 10, 286-96.

BROWN, J. M. & HAZEN, S. L. 2015. The gut microbial endocrine organ: bacterially derived signals driving cardiometabolic diseases. *Annu Rev Med,* 66, 343-59.

BUJAN, N., MOHAMMED, H., BALBOA, S., ROMALDE, J. L., TORANZO, A. E., ARIAS, C. R. & MAGARINOS, B. 2018. Genetic studies to re-affiliate *Edwardsiella tarda* fish isolates to *Edwardsiella piscicida* and *Edwardsiella anguillarum* species. *Syst Appl Microbiol,* 41, 30-37.

CACERES, A. I., LIU, B., JABBA, S. V., ACHANTA, S., MORRIS, J. B. & JORDT, S. E. 2017. Transient Receptor Potential Cation Channel Subfamily M Member 8 channels mediate the anti-inflammatory effects of eucalyptol. *Br J Pharmacol,* 174, 867-879.

CHIMEREL, C., EMERY, E., SUMMERS, D. K., KEYSER, U., GRIBBLE, F. M. & REIMANN, F. 2014. Bacterial metabolite indole modulates incretin secretion from intestinal enteroendocrine L cells. *Cell Rep,* 9, 1202-8.

CHOI, E. Y., LEE, H., DINGLE, R. W., KIM, K. B. & SWANSON, H. I. 2012. Development of novel CH223191-based antagonists of the aryl hydrocarbon receptor. *Mol Pharmacol,* 81, 3-11.

COCCHIARO, J. L. & RAWLS, J. F. 2013. Microgavage of zebrafish larvae. *J Vis Exp,* e4434.

COLEMAN, O. I. & HALLER, D. 2017. Bacterial Signaling at the Intestinal Epithelial Interface in Inflammation and Cancer. *Front Immunol,* 8, 1927.

CORNELISSEN, W., DE LAET, A., KROESE, A. B., VAN BOGAERT, P. P., SCHEUERMANN, D. W. & TIMMERMANS, J. P. 2000. Electrophysiological features of morphological Dogiel type II neurons in the myenteric plexus of pig small intestine. *J Neurophysiol,* 84, 102-11.

CRONAN, M. R., BEERMAN, R. W., ROSENBERG, A. F., SAELENS, J. W., JOHNSON, M. G., OEHLERS, S. H., SISK, D. M., JURCIC SMITH, K. L., MEDVITZ, N. A., MILLER, S. E., TRINH, L. A., FRASER, S. E., MADDEN, J. F., TURNER, J., STOUT, J. E., LEE, S. & TOBIN, D. M. 2016. Macrophage Epithelial Reprogramming Underlies Mycobacterial Granuloma Formation and Promotes Infection. *Immunity,* 45, 861-876.

ESPENSCHIED, S. T., CRONAN, M. R., MATTY, M. A., MUELLER, O., REDINBO, M. R., TOBIN, D. M. & RAWLS, J. F. 2019. Epithelial delamination is protective during pharmaceutical-induced enteropathy. *Proc Natl Acad Sci USA,* 116, 16961-16970.

FLORES, E. M., NGUYEN, A. T., ODEM, M. A., EISENHOFFER, G. T. & KRACHLER, A. M. 2020. The zebrafish as a model for gastrointestinal tract-microbe interactions. *Cell Microbiol,* 22, e13152.

FOGLIA, M. J., CAO, J., TORNINI, V. A. & POSS, K. D. 2016. Multicolor mapping of the cardiomyocyte proliferation dynamics that construct the atrium. *Development,* 143, 1688-96.

FOSQUE, B. F., SUN, Y., DANA, H., YANG, C. T., OHYAMA, T., TADROSS, M. R., PATEL, R., ZLATIC, M., KIM, D. S., AHRENS, M. B., JAYARAMAN, V., LOOGER, L. L. & SCHREITER, E. R. 2015. Neural circuits. Labeling of active neural circuits in vivo with designed calcium integrators. *Science,* 347, 755-60.

FULLING, C., DINAN, T. G. & CRYAN, J. F. 2019. Gut Microbe to Brain Signaling: What Happens in Vagus. *Neuron,* 101, 998-1002.

FURNESS, J. B., CALLAGHAN, B. P., RIVERA, L. R. & CHO, H. J. 2014. The enteric nervous system and gastrointestinal innervation: integrated local and central control. *Adv Exp Med Biol,* 817, 39-71.

FURNESS, J. B., KUNZE, W. A. & CLERC, N. 1999. Nutrient tasting and signaling mechanisms in the gut. II. The intestine as a sensory organ: neural, endocrine, and immune responses. *Am J Physiol,* 277, G922-8.

FURNESS, J. B., RIVERA, L. R., CHO, H. J., BRAVO, D. M. & CALLAGHAN, B. 2013. The gut as a sensory organ. *Nat Rev Gastroenterol Hepatol,* 10, 729-40.

GANZ, J., BAKER, R. P., HAMILTON, M. K., MELANCON, E., DIBA, P., EISEN, J. S. & PARTHASARATHY, R. 2018. Image velocimetry and spectral analysis enable quantitative characterization of larval zebrafish gut motility. *Neurogastroenterol Motil,* 30, e13351.

GERSHON, M. D. 2004. Review article: serotonin receptors and transporters—roles in normal and abnormal gastrointestinal motility. *Aliment Pharmacol Ther,* 20 Suppl 7, 3-14.

GERSHON, M. D. 2013. 5-Hydroxytryptamine (serotonin) in the gastrointestinal tract. *Curr Opin Endocrinol Diabetes Obes,* 20, 14-21.

GHOSHAL, U. C., SHUKLA, R. & GHOSHAL, U. 2017. Small Intestinal Bacterial Overgrowth and Irritable Bowel Syndrome: A Bridge between Functional Organic Dichotomy. *Gut Liver,* 11, 196-208.

GHOSHAL, U. C., SRIVASTAVA, D., GHOSHAL, U. & MISRA, A. 2014. Breath tests in the diagnosis of small intestinal bacterial overgrowth in patients with irritable bowel syndrome in comparison with quantitative upper gut aspirate culture. *Eur J Gastroenterol Hepatol,* 26, 753-60.

GRILL, H. J. & HAYES, M. R. 2009. The nucleus tractus solitarius: a portal for visceral afferent signal processing, energy status assessment and integration of their combined effects on food intake. *Int J Obes* (Lond), 33 Suppl 1, S11-5.

GUO, X., YIN, C., YANG, F., ZHANG, Y., HUANG, H., WANG, J., DENG, B., CAI, T., RAO, Y. & XI, R. 2019. The Cellular Diversity and Transcription Factor Code of *Drosophila* Enteroendocrine Cells. *Cell Rep,* 29, 4172-4185 e5.

GUPTA, V. & POSS, K. D. 2012. Clonally dominant cardiomyocytes direct heart morphogenesis. *Nature,* 484, 479-84.

HABER, A. L., BITON, M., ROGEL, N., HERBST, R. H., SHEKHAR, K., SMILLIE, C., BURGIN, G., DELOREY, T. M., HOWITT, M. R., KATZ, Y., TIROSH, I., BEYAZ, S., DIONNE, D., ZHANG, M., RAYCHOWDHURY, R., GARRETT, W. S., ROZENBLATT-ROSEN, O., SHI, H. N., YILMAZ, O., XAVIER, R. J. & REGEV, A. 2017. A single-cell survey of the small intestinal epithelium. *Nature,* 551, 333-339.

HAN, W., TELLEZ, L. A., PERKINS, M. H., PEREZ, I. O., QU, T., FERREIRA, J., FERREIRA, T. L., QUINN, D., LIU, Z. W., GAO, X. B., KAELBERER, M. M., BOHORQUEZ, D. V., SHAMMAH-LAGNADO, S. J., DE LARTIGUE, G. & DE ARAUJO, I. E. 2018. A Neural Circuit for Gut-Induced Reward. *Cell,* 175, 665-678 e23.

HEATH-PAGLIUSO, S., ROGERS, W. J., TULLIS, K., SEIDEL, S. D., CENIJN, P. H., BROUWER, A. & DENISON, M. S. 1998. Activation of the Ah receptor by tryptophan and tryptophan metabolites. *Biochemistry,* 37, 11508-15.

HOLZER, P. 2011. TRP channels in the digestive system. *Curr Pharm Biotechnol,* 12, 24-34.

HUBBARD, T. D., MURRAY, I. A., BISSON, W. H., LAHOTI, T. S., GOWDA, K., AMIN, S. G., PATTERSON, A. D. & PERDEW, G. H. 2015. Adaptation of the human aryl hydrocarbon receptor to sense microbiota-derived indoles. *Sci Rep,* 5, 12689.

JAGLIN, M., RHIMI, M., PHILIPPE, C., PONS, N., BRUNEAU, A., GOUSTARD, B., DAUGE, V., MAGUIN, E., NAUDON, L. & RABOT, S. 2018. Indole, a Signaling Molecule Produced by the Gut Microbiota, Negatively Impacts Emotional Behaviors in Rats. *Front Neurosci,* 12, 216.

JIN, U. H., LEE, S. O., SRIDHARAN, G., LEE, K., DAVIDSON, L. A., JAYARAMAN, A., CHAPKIN, R. S., ALANIZ, R. & SAFE, S. 2014. Microbiome-derived tryptophan metabolites and their aryl hydrocarbon receptor-dependent agonist and antagonist activities. *Mol Pharmacol,* 85, 777-88.

JOHN HAYNES, W., ZHOU, X. L., SU, Z. W., LOUKIN, S. H., SAIMI, Y. & KUNG, C. 2008. Indole and other aromatic compounds activate the yeast TRPY1 channel. *FEBS Lett,* 582, 1514-8.

JOHNSON, C. D., BARLOW-ANACKER, A. J., PIERRE, J. F., TOUW, K., ERICKSON, C. S., FURNESS, J. B., EPSTEIN, M. L. & GOSAIN, A. 2018. Deletion of choline acetyltransferase in enteric neurons results in postnatal intestinal dysmotility and dysbiosis. *FASEB J,* 32, 4744-4752.

KAELBERER, M. M., BUCHANAN, K. L., KLEIN, M. E., BARTH, B. B., MONTOYA, M. M., SHEN, X. & BOHORQUEZ, D. V. 2018. A gut-brain neural circuit for nutrient sensory transduction. *Science,* 361.

KAIKO, G. E. & STAPPENBECK, T. S. 2014. Host-microbe interactions shaping the gastrointestinal environment. *Trends Immunol,* 35, 538-48.

KAWAKAMI, K. 2007. Tol2: a versatile gene transfer vector in vertebrates. *Genome Biol,* 8 Suppl 1, S7.

KIM, D. J., VENKATARAMAN, A., JAIN, P. C., WIESLER, E. P., DEBLASIO, M., KLEIN, J., TU, S. S., LEE, S., MEDZHITOV, R. & IWASAKI, A. 2020. Vitamin B12 and folic acid alleviate symptoms of nutritional deficiency by antagonizing aryl hydrocarbon receptor. *Proc Natl Acad Sci USA,* 117, 15837-15845.

KNIGHT, R. D., MEBUS, K., D'ANGELO, A., YOKOYA, K., HEANUE, T., TUBINGEN SCREEN, C. & ROEHL, H. 2011. Ret signalling integrates a craniofacial muscle module during development. *Development,* 138, 2015-24.

KOKEL, D., CHEUNG, C. Y., MILLS, R., COUTINHO-BUDD, J., HUANG, L., SETOLA, V., SPRAGUE, J., JIN, S., JIN, Y. N., HUANG, X. P., BRUNI, G., WOOLF, C. J., ROTH, B. L., HAMBLIN, M. R., ZYLKA, M. J., MILAN, D. J. & PETERSON, R. T. 2013. Photochemical activation of TRPA1 channels in neurons and animals. *Nat Chem Biol,* 9, 257-63.

KUNST, M., LAURELL, E., MOKAYES, N., KRAMER, A., KUBO, F., FERNANDES, A. M., FORSTER, D., DAL MASCHIO, M. & BAIER, H. 2019. A Cellular-Resolution Atlas of the Larval Zebrafish Brain. *Neuron,* 103, 21-38 e5.

KWAN, K. M., FUJIMOTO, E., GRABHER, C., MANGUM, B. D., HARDY, M. E., CAMPBELL, D. S., PARANT, J. M., YOST, H. J., KANKI, J. P. & CHIEN, C. B. 2007. The Tol2kit: a multisite gateway-based construction kit for Tol2 transposon transgenesis constructs. *Dev Dyn,* 236, 3088-99.

LAPOINTE, T. K. & ALTIER, C. 2011. The role of TRPA1 in visceral inflammation and pain. *Channels* (*Austin*), 5, 525-9.

LEITE, G., MORALES, W., WEITSMAN, S., CELLY, S., PARODI, G., MATHUR, R., BARLOW, G. M., SEDIGHI, R., MILLAN, M. J. V., REZAIE, A. & PIMENTEL, M. 2020. The duodenal microbiome is altered in small intestinal bacterial overgrowth. *PLoS One,* 15, e0234906.

LI, Z., CHALAZONITIS, A., HUANG, Y. Y., MANN, J. J., MARGOLIS, K. G., YANG, Q. M., KIM, D. O., COTE, F., MALLET, J. & GERSHON, M. D. 2011. Essential roles of enteric neuronal serotonin in gastrointestinal motility and the development/survival of enteric dopaminergic neurons. *J Neurosci,* 31, 8998-9009.

LIU, Y., HOU, Y., WANG, G., ZHENG, X. & HAO, H. 2020. Gut Microbial Metabolites of Aromatic Amino Acids as Signals in Host-Microbe Interplay. *Trends Endocrinol Metab,* 31, 818-834.

LOVE, M. I., HUBER, W. & ANDERS, S. 2014. Moderated estimation of fold change and dispersion for RNA-seq data with DESeq2. *Genome Biol,* 15, 550.

LU, V. B., GRIBBLE, F. M. & REIMANN, F. 2018. Free Fatty Acid Receptors in Enteroendocrine Cells. *Endocrinology,* 159, 2826-2835.

MACPHERSON, L. J., DUBIN, A. E., EVANS, M. J., MARR, F., SCHULTZ, P. G., CRAVATT, B. F. & PATAPOUTIAN, A. 2007. Noxious compounds activate TRPA1 ion channels through covalent modification of cysteines. *Nature,* 445, 541-5.

MATHIAS, J. R., ZHANG, Z., SAXENA, M. T. & MUMM, J. S. 2014. Enhanced cell-specific ablation in zebrafish using a triple mutant of *Escherichia coli* nitroreductase. *Zebrafish,* 11, 85-97.

MCGRAW, H. F., SNELSON, C. D., PRENDERGAST, A., SULI, A. & RAIBLE, D. W. 2012. Postembryonic neuronal addition in zebrafish dorsal root ganglia is regulated by Notch signaling. *Neural Dev,* 7, 23.

MEIJERING, E., DZYUBACHYK, O. & SMAL, I. 2012. Methods for cell and particle tracking. *Methods Enzymol,* 504, 183-200.

MESEGUER, V., ALPIZAR, Y. A., LUIS, E., TAJADA, S., DENLINGER, B., FAJARDO, O., MANENSCHIJN, J. A., FERNANDEZ-PENA, C., TALAVERA, A., KICHKO, T., NAVIA, B., SANCHEZ, A., SENARIS, R., REEH, P., PEREZ-GARCIA, M. T., LOPEZ-LOPEZ, J. R., VOETS, T., BELMONTE, C., TALAVERA, K. & VIANA, F. 2014. TRPA1 channels mediate acute neurogenic inflammation and pain produced by bacterial endotoxins. *Nat Commun,* 5, 3125.

MURDOCH, C. C., ESPENSCHIED, S. T., MATTY, M. A., MUELLER, O., TOBIN, D. M. & RAWLS, J. F. 2019. Intestinal Serum amyloid A suppresses systemic neutrophil activation and bactericidal activity in response to microbiota colonization. *PLoS Pathog,* 15, e1007381.

NAGEL, G., SZELLAS, T., HUHN, W., KATERIYA, S., ADEISHVILI, N., BERTHOLD, P., OLLIG, D., HEGEMANN, P. & BAMBERG, E. 2003. Channelrhodopsin-2, a directly light-gated cation-selective membrane channel. *Proc Natl Acad Sci USA,* 100, 13940-5.

NAKAMURA, Y., TAKANO, T., YASUIKE, M., SAKAI, T., MATSUYAMA, T. & SANO, M. 2013. Comparative genomics reveals that a fish pathogenic bacterium *Edwardsiella tarda* has acquired the locus of enterocyte effacement (LEE) through horizontal gene transfer. *BMC Genomics,* 14, 642.

NAUMANN, E. A., FITZGERALD, J. E., DUNN, T. W., RIHEL, J., SOMPOLINSKY, H. & ENGERT, F. 2016. From Whole-Brain Data to Functional Circuit Models: The Zebrafish Optomotor Response. *Cell,* 167, 947-960 e20.

NILIUS, B., PRENEN, J. & OWSIANIK, G. 2011. Irritating channels: the case of TRPA1. *J Physiol,* 589, 1543-9.

NOZAWA, K., KAWABATA-SHODA, E., DOIHARA, H., KOJIMA, R., OKADA, H., MOCHIZUKI, S., SANO, Y., INAMURA, K., MATSUSHIME, H., KOIZUMI, T., YOKOYAMA, T. & ITO, H. 2009. TRPA1 regulates gastrointestinal motility through serotonin release from enterochromaffin cells. *Proc Natl Acad Sci USA,* 106, 3408-13.

PAN, H. & GERSHON, M. D. 2000. Activation of intrinsic afferent pathways in submucosal ganglia of the guinea pig small intestine. *J Neurosci,* 20, 3295-309.

PARK, S. B., AOKI, T. & JUNG, T. S. 2012. Pathogenesis of and strategies for preventing *Edwardsiella tarda* infection in fish. *Vet Res,* 43, 67.

PHAM, L. N., KANTHER, M., SEMOVA, I. & RAWLS, J. F. 2008. Methods for generating and colonizing gnotobiotic zebrafish. *Nat Protoc,* 3, 1862-75.

PROBER, D. A., ZIMMERMAN, S., MYERS, B. R., MCDERMOTT, B. M., JR., KIM, S. H., CARON, S., RIHEL, J., SOLNICA-KREZEL, L., JULIUS, D., HUDSPETH, A. J. & SCHIER, A. F. 2008. Zebrafish TRPA1 channels are required for chemosensation but not for thermosensation or mechanosensory hair cell function. *J Neurosci,* 28, 10102-10.

PUYSKENS, A., STINN, A., VAN DER VAART, M., KREUCHWIG, A., PROTZE, J., PEI, G., KLEMM, M., GUHLICH-BORNHOF, U., HURWITZ, R., KRISHNAMOORTHY, G., SCHAAF, M., KRAUSE, G., MEIJER, A. H., KAUFMANN, S. H. E. & MOURA-ALVES, P. 2020. Aryl Hydrocarbon Receptor Modulation by Tuberculosis Drugs Impairs Host Defense and Treatment Outcomes. *Cell Host Microbe,* 27, 238-248 e7.

QU, Z. D., THACKER, M., CASTELUCCI, P., BAGYANSZKI, M., EPSTEIN, M. L. & FURNESS, J. B. 2008. Immunohistochemical analysis of neuron types in the mouse small intestine. *Cell Tissue Res,* 334, 147-61.

RANDLETT, O., WEE, C. L., NAUMANN, E. A., NNAEMEKA, O., SCHOPPIK, D., FITZGERALD, J. E., PORTUGUES, R., LACOSTE, A. M., RIEGLER, C., ENGERT, F. & SCHIER, A. F. 2015. Whole-brain activity mapping onto a zebrafish brain atlas. *Nat Methods,* 12, 1039-46.

RAWLS, J. F., MAHOWALD, M. A., LEY, R. E. & GORDON, J. I. 2006. Reciprocal gut microbiota transplants from zebrafish and mice to germ-free recipients reveal host habitat selection. *Cell,* 127, 423-33.

ROACH, G., HEATH WALLACE, R., CAMERON, A., EMRAH OZEL, R., HONGAY, C. F., BARAL, R., ANDREESCU, S. & WALLACE, K. N. 2013. Loss of ascl1a prevents secretory cell differentiation within the zebrafish intestinal epithelium resulting in a loss of distal intestinal motility. *Dev Biol,* 376, 171-86.

ROBERTS, G. P., LARRAUFIE, P., RICHARDS, P., KAY, R. G., GALVIN, S. G., MIEDZYBRODZKA, E. L., LEITER, A., LI, H. J., GLASS, L. L., MA, M. K. L., LAM, B., YEO, G. S. H., SCHARFMANN, R., CHIARUGI, D., HARDWICK, R. H., REIMANN, F. & GRIBBLE, F. M. 2019. Comparison of Human and Murine Enteroendocrine Cells by Transcriptomic and Peptidomic Profiling. *Diabetes,* 68, 1062-1072.

ROLIG, A. S., MITTGE, E. K., GANZ, J., TROLL, J. V., MELANCON, E., WILES, T. J., ALLIGOOD, K., STEPHENS, W. Z., EISEN, J. S. & GUILLEMIN, K. 2017. The enteric nervous system promotes intestinal health by constraining microbiota composition. *PLoS Biol,* 15, e2000689.

SCHINDELIN, J., ARGANDA-CARRERAS, I., FRISE, E., KAYNIG, V., LONGAIR, M., PIETZSCH, T., PREIBISCH, S., RUEDEN, C., SAALFELD, S., SCHMID, B., TINEVEZ, J. Y., WHITE, D. J., HARTENSTEIN, V., ELICEIRI, K., TOMANCAK, P. & CARDONA, A. 2012. Fiji: an open-source platform for biological-image analysis. *Nat Methods,* 9, 676-82.

SMITH, T. 1897. A Modification of the Method for Determining the Production of Indol by Bacteria. *J Exp Med,* 2, 543-7.

SRINIVASA RAO, P. S., LIM, T. M. & LEUNG, K. Y. 2003. Functional genomics approach to the identification of virulence genes involved in *Edwardsiella tarda* pathogenesis. *Infect Immun,* 71, 1343-51.

STEPHENS, W. Z., BURNS, A. R., STAGAMAN, K., WONG, S., RAWLS, J. F., GUILLEMIN, K. & BOHANNAN, B. J. 2016. The composition of the zebrafish intestinal microbial community varies across development. *ISME J,* 10, 644-54.

SUN, E. W., MARTIN, A. M., WATTCHOW, D. A., DE FONTGALLAND, D., RABBITT, P., HOLLINGTON, P., YOUNG, R. L. & KEATING, D. J. 2019a. Metformin Triggers PYY Secretion in Human Gut Mucosa. *J Clin Endocrinol Metab,* 104, 2668-2674.

SUN, Y., TANG, L., LIU, Y., HU, C., ZHOU, B., LAM, P. K. S., LAM, J. C. W. & CHEN, L. 2019b. Activation of aryl hydrocarbon receptor by dioxin directly shifts gut microbiota in zebrafish. *Environ Pollut,* 255, 113357.

SYMONDS, E. L., PEIRIS, M., PAGE, A. J., CHIA, B., DOGRA, H., MASDING, A., GALANAKIS, V., ATIBA, M., BULMER, D., YOUNG, R. L. & BLACKSHAW, L. A. 2015. Mechanisms of activation of mouse and human enteroendocrine cells by nutrients. *Gut,* 64, 618-26.

TARAVIRAS, S., MARCOS-GUTIERREZ, C. V., DURBEC, P., JANI, H., GRIGORIOU, M., SUKUMARAN, M., WANG, L. C., HYNES, M., RAISMAN, G. & PACHNIS, V. 1999. Signalling by the RET receptor tyrosine kinase and its role in the development of the mammalian enteric nervous system. *Development,* 126, 2785-97.

TORNINI, V. A., THOMPSON, J. D., ALLEN, R. L. & POSS, K. D. 2017. Live fate-mapping of joint-associated fibroblasts visualizes expansion of cell contributions during zebrafish fin regeneration. *Development,* 144, 2889-2895.

TRAVAGLI, R. A. & ANSELMI, L. 2016. Vagal neurocircuitry and its influence on gastric motility. *Nat Rev Gastroenterol Hepatol,* 13, 389-401.

TRAVAGLI, R. A., HERMANN, G. E., BROWNING, K. N. & ROGERS, R. C. 2006. Brainstem circuits regulating gastric function. *Annu Rev Physiol,* 68, 279-305.

TSENG, Q., DUCHEMIN-PELLETIER, E., DESHIERE, A., BALLAND, M., GUILLOU, H., FILHOL, O. & THERY, M. 2012. Spatial organization of the extracellular matrix regulates cell-cell junction positioning. *Proc Natl Acad Sci USA,* 109, 1506-11.

ULHAQ, Z. S. & KISHIDA, M. 2018. Brain Aromatase Modulates Serotonergic Neuron by Regulating Serotonin Levels in Zebrafish Embryos and Larvae. *Front Endocrinol* (*Lausanne*), 9, 230.

VENKATESH, M., MUKHERJEE, S., WANG, H., LI, H., SUN, K., BENECHET, A. P., QIU, Z., MAHER, L., REDINBO, M. R., PHILLIPS, R. S., FLEET, J. C., KORTAGERE, S., MUKHERJEE, P., FASANO, A., LE VEN, J., NICHOLSON, J. K., DUMAS, M. E., KHANNA, K. M. & MANI, S. 2014. Symbiotic bacterial metabolites regulate gastrointestinal barrier function via the xenobiotic sensor PXR and Toll-like receptor 4. *Immunity,* 41, 296-310.

YANG, M., LV, Y., XIAO, J., WU, H., ZHENG, H., LIU, Q., ZHANG, Y. & WANG, Q. 2012. *Edwardsiella* comparative phylogenomics reveal the new intra/inter-species taxonomic relationships, virulence evolution and niche adaptation mechanisms. *PLoS One,* 7, e36987.

YANG, Y., WANG, S., KOBAYASHI, K., HAO, Y., KANDA, H., KONDO, T., KOGURE, Y., YAMANAKA, H., YAMAMOTO, S., LI, J., MIWA, H., NOGUCHI, K. & DAI, Y. 2019. TRPA1-expressing lamina propria mesenchymal cells regulate colonic motility. *JCI Insight,* 4.

YANO, J. M., YU, K., DONALDSON, G. P., SHASTRI, G. G., ANN, P., MA, L., NAGLER, C. R., ISMAGILOV, R. F., MAZMANIAN, S. K. & HSIAO, E. Y. 2015. Indigenous bacteria from the gut microbiota regulate host serotonin biosynthesis. *Cell,* 161, 264-76.

YE, L., MUELLER, O., BAGWELL, J., BAGNAT, M., LIDDLE, R. A. & RAWLS, J. F. 2019. High fat diet induces microbiota-dependent silencing of enteroendocrine cells. *Elife,* 8.

YUE, C., JI, C., ZHANG, H., ZHANG, L. W., TONG, J., JIANG, Y. & CHEN, T. 2017. Protective effects of folic acid on PM2.5-induced cardiac developmental toxicity in zebrafish embryos by targeting AhR and Wnt/beta-catenin signal pathways. *Environ Toxicol,* 32, 2316-2322.

ZELANTE, T., IANNITTI, R. G., CUNHA, C., DE LUCA, A., GIOVANNINI, G., PIERACCINI, G., ZECCHI, R., D'ANGELO, C., MASSI-BENEDETTI, C., FALLARINO, F., CARVALHO, A., PUCCETTI, P. & ROMANI, L. 2013. Tryptophan catabolites from microbiota engage aryl hydrocarbon receptor and balance mucosal reactivity via interleukin-22. *Immunity,* 39, 372-85.

ZELKAS, L., RAGHUPATHI, R., LUMSDEN, A. L., MARTIN, A. M., SUN, E., SPENCER, N. J., YOUNG, R. L. & KEATING, D. J. 2015. Serotonin-secreting enteroendocrine cells respond via diverse mechanisms to acute and chronic changes in glucose availability. *Nutr Metab* (Lond), 12, 55.

What is claimed is:

1. A method of increasing intestinal motility in a subject, comprising administering indole-3-carboxaldehyde to the subject.

2. The method of claim 1, wherein the subject has a gastrointestinal motility disorder, wherein the gastrointestinal motility disorder is irritable bowel syndrome (IBS).

3. The method of claim 2, wherein the gastrointestinal motility disorder is constipation predominant IBS (IBS-C) or post-infectious IBS (PI-IBS).

4. The method of claim 1, wherein the subject is human.

* * * * *